(12) United States Patent
Zhao et al.

(10) Patent No.: US 8,580,515 B2
(45) Date of Patent: Nov. 12, 2013

(54) SURFACE-MODIFIED SINGLE-WALLED CARBON NANOTUBES AND METHODS OF DETECTING A CHEMICAL COMPOUND USING SAME

(75) Inventors: Wei Zhao, Little Rock, AR (US); Chulho Song, An-Yang (KR)

(73) Assignee: Board of Trustees of the University of Arkansas, Little Rock, AR (US)

( * ) Notice: Subject to any disclaimer, the term of this patent is extended or adjusted under 35 U.S.C. 154(b) by 1793 days.

(21) Appl. No.: 11/601,328

(22) Filed: Nov. 17, 2006

(65) Prior Publication Data

US 2010/0086910 A1 Apr. 8, 2010

Related U.S. Application Data

(62) Division of application No. 11/020,024, filed on Dec. 21, 2004, now abandoned.

(60) Provisional application No. 60/603,181, filed on Aug. 20, 2004.

(51) Int. Cl.
| | | |
|---|---|---|
| *C12Q 1/30* | (2006.01) | |
| *C12Q 1/68* | (2006.01) | |
| *C12Q 1/60* | (2006.01) | |
| *C12Q 1/54* | (2006.01) | |
| *C12Q 1/26* | (2006.01) | |
| *G01N 21/00* | (2006.01) | |
| *G01N 31/00* | (2006.01) | |
| *G01N 33/18* | (2006.01) | |
| *C12Q 1/62* | (2006.01) | |
| *C12Q 1/48* | (2006.01) | |
| *C12Q 1/28* | (2006.01) | |
| *C12Q 1/32* | (2006.01) | |
| *C12Q 1/34* | (2006.01) | |
| *G01N 1/10* | (2006.01) | |
| *G01N 33/50* | (2006.01) | |

(52) U.S. Cl.
USPC ............... 435/6.19; 435/11; 435/14; 435/25; 436/135; 436/163; 436/164; 977/745

(58) Field of Classification Search
USPC ............. 435/6.19, 11, 14, 25, 135, 163, 164; 977/745
See application file for complete search history.

(56) References Cited

U.S. PATENT DOCUMENTS

| | | | |
|---|---|---|---|
| 7,074,310 B2 * | 7/2006 | Smalley et al. ............... 204/450 |
| 2004/0038251 A1 | 2/2004 | Smalley et al. | |
| 2004/0040834 A1 * | 3/2004 | Smalley et al. ............... 204/164 |

OTHER PUBLICATIONS

Buck et al. 1999 . New electrochemical and optical sensing techniques for the liquid phase. Fresenius Journal of Analytical Chemistry, vol. 363, No. 7, pp. 607-611.*
Smith Jr. et al. 2003. Selective oxidation of single-walled carbon nanotubes using carbon dioxide. Carbon, vol. 41, pp. 1221-1230.*
Wikipedia. (http://en.wikipwdia.org/wiki/Hydrogen_peroxide , pp. 1-21, printed Sep. 30, 2010.*
Kong, J. et al., Nanotube Molecular Wires as Chemical Sensors, "Science 2000", 287, pp. 622-625.
Collins, et al., Extreme Oxygen Sensitivity of Electronic Properties of Carbon Nanotubes, "Science 2000", 287, pp. 1801-1804.
Chen, et al., Noncovalent Sidewall Functionalization of Single-Walled Carbon Nanotubes for Protein Immobilization, *J. Am. Chem. Soc.* (2001) 123, 3838-3839.
Shim et al., Functionalization of Carbon Nanotubes for Biocompatibility and Biomolecular Recognition, *Nano Letters* (2002) 2, 285-288.
Kong et al., Full and Modulated Chemical Gating of Individual Carbon Nanotubes by Organic Amine Compounds, *J. Phys. Chem.* B (2001) 105, 2890-2893.
Erlanger et al., Binding of an Anti-Fullerene IgG Monoclonal Antibody to Single Wall Carbon Nanotubes, *Nano Letters* (2001) 1,456-467.
O'Connell et al., Reversible water-solubilization of single-walled carbon nanotubes by polymer wrapping, *Chem. Phys. Letters* (2001) 342, 265-271.
Itkis et al., Spectroscopic Study of the Fermi Level Electronic Structure of Single-Walled Carbon Nanotubes, *Nano Letters* (2002) 2, 155-159.
Chen et al., Solution Properties of Single-Walled Carbon Nanotubes, *Science* (1998) 282, 95-98.
Yang et al., Toward the Chemistry of Carboxylic Single-Walled Carbon Nanotubes by Chemical Force Microscopy, *J. Phys. Chem. B.* (2002) 106, 4139-4144.

(Continued)

*Primary Examiner* — Jon P Weber
*Assistant Examiner* — Kailash C Srivastava
(74) *Attorney, Agent, or Firm* — Morris, Manning & Martin, LLP; Tim Tingkang Xia, Esq.

(57) ABSTRACT

A method for surface modification of single walled carbon nanotubes is described. In one embodiment, the method includes the steps of providing a detergent solution, adding a plurality of single walled carbon nanotubes into the detergent solution, performing a first sonication to disperse the single walled carbon nanotubes in the detergent solution, and performing a second sonication after the first sonication to make detergent encased single walled carbon nanotubes. At least one of the plurality of single walled carbon nanotubes is at least partially wrapped by one or more detergent molecules to make it a detergent encased single walled carbon nanotube. In one embodiment, the detergent comprises SDS, PSS or a combination of them. The surface modified carbon nanotubes can be used to detect a chemical compound by associating a solution of the surface modified nanotubes with the chemical compound and optically detecting a chemical property change of the solution.

18 Claims, 33 Drawing Sheets

(56) References Cited

OTHER PUBLICATIONS

Cui et al., Nanowire Nanosensors for Highly Sensitive and Selective Detection of Biological and Chemical Species, *Science* (2001) 293, 1289-1292.
Liu et al., Fullerne Pipes, *Science* (1998) 280, 1253-1256.
Rinzler et al., Large-scale purification of single-wall carbon nanotubes: process, product, and characterization, *Appl. Phys. A.* (1998) 67, 29-37.
Chen et al., Dissolution of Full-Length Single-Walled Carbon Nanotubes *J. Phys. Chem. B.* (2001) 105, 2525-2528.
Mickelson et al., Solvation of Fluorinated Single-Wall Carbon Nanotubes in Alcohol Solvents, *J. Phys. Chem, B.* (1999) 103, 4318-4322.
Georgakilas et al., Organic Functionalization of Carbon Nanotbues, *J. Am. Chem. Soc.* (2002) 124, 760-761.
Sun et al., High Dissolution and Strong Light Emission of Carbon Nanotubes in Aromatic Amine Solvents, *J. Am. Chem. Soc.* (2001) 123, 5348-5349.
Steuerman et al., Interactions between Conjugated Polymers and Single-Walled Carbon Nanotubes, *J. Phys. Chem. B.* (2002) 106, 3124-3130.
Star et al., Starched Carbon Nanotubes, *Agnew. Chem., Int. Ed.* (2002) 41, 2508-2512.
Bandyopadhyaya et al., Stabilization of Individual Carbon Nanotubes in Aqueous Solutions, *Nano Letters* (2002) 2, 25-28.
Pompeo et al., Water Solubilization of Single-Walled Carbon Nanotubes by Functionalization with Glucosamine, *Nano Letters* (2002) 2, 369-373.
Chaing et al., Purification and Characterization of Single-Wall Carbon Nanotubes (SWNTs) Obtained from the Gas-Phase Decomposition of CO (HiPoc Process), *J. phys. Chem. B.* (2002) 105, 8297-8301.
CRC Handbook of Chemistry and Physics, $82^{nd}$ ed.: Lide ed.-in-Chief: CRC Press: New York (2001-2002) pp. 8-43.
Shimoda et al., Lithium Intercalation into Opened Snigle-Wall Carbon Nanotubes: Storage Capacity and Electronic Properties, *Phys. Rev. Lett.* (2002) 88, 015502-1-015502-4.
Zhao et al., Water-Soluble and Optically pH-Sensitive Single-Walled Carbon Nanotubes from Surface Modification, *J. Am. Chem. Soc.* (2002) 124, 12418-12419.
Chen et al., Noncovalent functionalization of carbon nanotubes for highly specific electronic biosensors, *Proc. Natl. Acad. Sci. U.S.A.* (2003) 100, 4984-4989.
Qi et al., Toward Large Arrays of Multiplex Functionalized Carbon Nanotube Sensors for Highly Sensitive and Selective Molecular Detection, *Nano Letters* (2003) 3, 347-351.
Chen et al., An investigation of the Mechanisms of Electronic Sensing of Protein Adsorption on Carbon Nanotube Devices, *J. Am. Chem. Soc.* (2004) 126, 1563-1568.
Zheng et al., DNA-assisted dispersion and separation of carbon nanotubes, *Nature Mater.* (2003) 2, 338-342.
Zheng et al., Structure-Based Carbon Nanotubo Sorting by Sequence-Dependent DNA Assembly, *Science* (2003) 302, 1545-1548.
Krupke et al., Separation of Metallic from Semiconducting Single-Walled Carbon Nanotubes, *Science* (2003) 301, 344-347.
Strano et al., Electronic Structure Control of Single-Walled Carbon Nanotube Functionalization, *Science* (2003) 301, 1519-1522.
Guiseppi et al., Direct electron transfer of glucose oxidase on carbon nanotubes, *Nonotech* (2002) 13, 559-564.
O'Connell et al., Band Gap Fluorescence from Individual Single-Walled Carbon Nanotubes, *Science* (2002) 97, 593-596.
Strano et al., Reversible, Band-Gap-Selective Protonation of Single-Walled Carbon Nanotubes in Solution, *J. Phys. Chem. B.* (2003) 107, 6979-6985.
Ostojic et al., Interband Recombination Dynamics in Resonantly Excited Single-Walled Carbon Nanotubes, *Phys. Rev. Lett.* (2004) 92, 117402-1-117402-4.
Filho et al., Raman spectroscopy for probing chemically/physically induced phenomena in carbon nanotubes, *Nanotechnology* (2003) 14, 1130-1139.
Nakashima et al., DNA Dissolves Single-walled Carbon Nanotubes in Water, *Chem. Lett.* (2003) 32, 456-457.
Pehrsson et al., Thermal Fluorination and Annealing of Single-Wall Carbon Nanotubes, *J. Phys. Chem. B.* (2003) 107, 5690-5695.
Weisman et al., Dependence of Optical Transition Energies on Structure for Single-Walled Carbon Nanotubes in Aqueous Suspension: an Empirical Kataura Plot, *Nano Letters* (2003) 3, 1235-1238.
Besteman et al., Enzyme-Coated Carbon Nanotubes as Single-Molecule Biosensors, *Nano Letters* (2003) 3, 727-730.
Lin et al., Glucose Biosensors Based on Carbon Nanotube Nanoelectrode Ensembles, *Nano Letters* (2004) 4, 191-195.
Johnson et al., Single gallium nitride nanowire lasers, *Nature* (2002) 1, 106-110.
Schaller et al., Tunable Near-Infrared Optical Gain and Amplified Spontaneous Emission Using PbSe Nanocrystals, *J. Phys. Chem. B.* (2003) 107, 13765-13768.
Tong et al., Subwavelength-diameter silica wires for low-loss optical wave guiding, *Nature* (2003) 426, 816-819.
Goldoni et al. Single-Wall Carbon Nanotube Interaction With Gases: Sample Contaminants and Environmental Monitoring, *J. Am. Chem. Soc.* (2003) 125, 11329-11333.
Mark et al., Formation of Peroxynitrite by Sonication of Aerated Water, *J. Am. Chem. Soc.* (2000) 122, 3781-3782.
Misik et al, Nitric Oxide Formation by Ultrasound in Aqueous Solutions, *J. Phys, Chem.* (1996) 100, 17986-17994.
Hart et al., Isotopic Exchange in the Sonolysis of Aqueous Solutions Containing $^{14,14}N_2$ and $^{15,15}N_2$, *J. Phys. Chem..* (1986) 90, 5989-5991.
Virtanen et al., Nitrogen Fixation in an Ultrasonic Field, *J. Am. Chem. Soc.* (1950) 72, 1046-1047.
Mead et al., The effect of ultrasound on water in the presence of dissolved gases, *Can. J. Chem.* (1976) 54, 1114-1120.
Someya et al., Alcohol Vapor Sensors Based on Single-Walled Carbon Nanotube Field Effect Transitors, *Nano Letters.* (2003) 3, 877-881.
Bradley et al., Influence of Mobile Ions on Nanotube Based FET Devices, *Nano Letters.* (2003) 3, 639-641.
Li et al., Carbon Nanotube Sensors for Gas and Organic Vapor Detection, *Nano Letters* (2003) 3, 929-933.
Kamaras et al., Covalent Bond Formation to a Carbon Nanotube Metal, *Science* (2003) 301, 1501.
Dekkar et al., Carbon Nanotubes As Molecular Quantum Wires, *C. Phys. Today* (1999) 52, 22-28.
Hahm et al., Direct Ultrasensitive Electrical Detection of DNA and DNA Sequence Variations Using Nanowire Nenosensors, *Nano Letters* (2004) 4, 51-54.
Kelly et al., Optical pH Response of DNA Wrapped HiPco Carbon Nanotubes, J. Nanosci. Nanotech (2005) 5, 1041-1044.
Harris D.C., *Exploring Chemical Analysis $3^{rd}$ ed.*; Aw. H. Freeman and Company, New York (2004) pp. 187 and 224.
An et al., A Simple Chemical Route to Selectively Eliminate Metallic Carbon Nanotubes in Nanotube Network Devices, *J. Am. Chem. Soc.* (2004) 126, 10520-10521.
Star et al., Nanotube Optoelectronic Memory Devices, *Nano Letters* (2004) 4, 1587-1591.
Turner et al. (Eds.) *Biosensors; Fundamentals and Applications*: Oxford university Press: New York (1987).
Law et al., Nanoribbon Waveguides for Subwavelength Photonics Integration, *Science* (2004) 305, 1269-1273.
Zhao et al., Thermal Recovery Behavior of Fluorinated Single-Walled Carbon Nanotubes, *J. Phys. Chem. B.* (2002) 106, 293-296.
Azamian et al., Bioeletrochemical Single-Walled Carbon Nanotubes, *J. Am.Chem. Soc.* (2002) 124, 12664-12665.
Ponganis et al., Electron-Transfer Reactions of Copper Complexes. 1. A Kinetic Investigation of the Oxidation of Bis(1,10-phenanthroline)copper(I) by Hydrogen Peroxide in Aqueous and Sodium Dodecyl Sulfate Solution, *Inorg. Chem.* (1980) 19, 2704-2709.

(56) References Cited

OTHER PUBLICATIONS

Jankovic et al., Influence of sodium dodecyl sulfate on the reaction between Nile Blue A and hydrogen peroxide, *J. Serbian Chem. Soc.* (1999) 64, 359-364.

Yurekli et al., Small-Angle Neutron Scattering from Surfactant-Assisted Aqueous Dispersions of Carbon Nanotubes, *J. Am. Chem. Soc.* (2004) 126, 9902-9903.

Prasad N., *Introduction to Biophotonics*, John Wiley: New York (2003).

Mattu et al., Determination of Glucose in a Biological Matrix by Multivariate Analysis of Multiple Band-Pass-Filtered Fourier Transform Near-Infrared Interferograms, *Anal. Chem.* (1997) 69, 4695-4702.

Landfester, L. Polyreactions in Miniemulsions Macromolecular Rapid Communications, 2001, vol. 22, No. 12, pp. 896-936.

* cited by examiner

SURFACE-MODIFIED SINGLE-WALLED CARBON NANOTUBES AND METHODS OF DETECTING A CHEMICAL COMPOUND USING SAME

CROSS-REFERENCE TO RELATED PATENT APPLICATION

This application is a divisional of, and claims benefit of U.S. patent application Ser. No. 11/020,024, filed Dec. 21, 2004, entitled "Surface-Modified Single-Walled Carbon Nanotubes and Methods of Detecting a Chemical Compound Using Same," by Wei Zhao, et al., abandoned, the disclosure of which is incorporated herein by reference in its entirety. U.S. patent application Ser. No. 11/020,024 claims benefit pursuant to 35 U.S.C. §119(e), of provisional U.S. Patent Application Ser. No. 60/603,181, filed Aug. 20, 2004, entitled "Surface-Modified Single-walled Carbon Nanotube Optical Biosensors and Methods of Making and/or Using Same," by Wei Zhao and Chulho Song, which is incorporated herein by reference in its entirety.

This invention was made with certain Government support, and the Government has certain rights in this invention.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [14] represents the 14th reference cited in the reference list, namely, Zhao, W.; Song, C.; Pehrsson, P. *J. Am. Chem. Soc.* 2002, 124, 12418-12419.

FIELD OF THE INVENTION

The present invention relates to surface modified single walled carbon nanotubes and a method of detecting a chemical compound using same.

BACKGROUND OF THE INVENTION

There is great interest in using single-walled carbon nanotubes (SWNTs) as nanoscale probes and sensors in biological electronics and optical devices because the electronic and optical properties of SWNTs are extremely sensitive to the surrounding environmental changes [1-5, 14-18, 21-25, 30, 31, 35, 42-45, 50, 51]. To date, most research on SWNTs has focused on electronic devices, with relatively little work on optical biosensors. In order to use SWNTs as optic biosensors, some immediate questions needs to be solved such as how the sensors respond to chemical variables like pH [5c] and concentration of glucose, ethanol, various ions, or proteins.

SWNTs are a collection of semiconducting, metallic nanotubes and a mixture of them in different diameters that can be probed by various spectroscopic methods including Raman spectroscopy and UV/vis/NIR absorption spectroscopy. Raman spectroscopy can be used to determine many aspects of an SWNTs sample, including size distribution, disorder from defects or functionalization, and general electronic behaviors.

SWNTs possess unique optical properties as a result of their one-dimensional nature. Sharp peaks in the density of states, called van Hove singularities (VHS), arise from a quantization of the electronic wave vector in the 1-D system [26]. As a result of these singularities, SWNTs possess peaks in their optical spectra that correspond to interband transitions from the valence band to the conduction band. In addition, the transitions are found to be grouped in spectral space according to nanotube type (metallic vs. semiconducting) and band index, which are responsible for the observed sharp and pronounced optical absorption peaks in individual HiPco SWNTs [21, 23].

The side view of an SWNT 100 is illustrated in FIG. 1a. The SWNT has a first end 110, an opposite, second end 120 and a body portion defined therebetween the first end 110 and the second end 120. The body portion contains a carbon "wall" that is formed by a plurality of carbon atoms in certain arrangements as known to people skilled in the art. As illustrated in FIG. 1b, the SWNT 100 can be considered to have an exterior surface 130, an interior surface 140, and a cavity 150, respectively.

Because current techniques produce SWNTs in a mixture form with about one third of metallic nanotubes and two thirds of semiconducting nanotubes [46], separations of semiconducting SWNTs from metallic SWNTs are required for practical applications [6, 47]. The study of SWNT separations is a subject of intense exploration [18-20]. The discovery of surfactant-assisted dissolution of SWNTs in aqueous sodium dodecyl sulfate (SDS) solution [23] has greatly stimulated the progress in this exciting area [18-20].

Water-soluble SWNTs (ws-SWNTs) with undisrupted characteristic optical absorption features have been obtained by surface modifications such as functionalization with carboxylate groups [14] and surface coatings with surfactants [21, 23] or single stranded DNA [18, 19]. FIG. 1c illustrates an SWNT encased in polymeric material 170. It has been observed that the optical characteristics of surface modified SWNTs are pH sensitive [14, 18, 23-25], which suggests new opportunities for SWNTs based optical biosensor applications yet to be explored. Nanotubes may even be combined with recently developed nanolasers [33], nano waveguides [53] and nano optical fibers [34], to make optical nanosensors in the near future.

Therefore, a heretofore unaddressed need exists in the art to address the aforementioned deficiencies and inadequacies.

SUMMARY OF THE INVENTION

The present invention, in one aspect, relates to a method for surface modification of single walled carbon nanotubes. The method includes the steps of providing a detergent solution, adding a plurality of single walled carbon nanotubes into the detergent solution, performing a first sonication to disperse the single walled carbon nanotubes in the detergent solution, and performing a second sonication after the first sonication to make detergent encased single walled carbon nanotubes. At least one of the plurality of single walled carbon nanotubes is at least partially wrapped by one or more detergent molecules to make it a detergent encased single walled carbon nanotube. In one embodiment, the detergent comprises SDS, PSS or a combination of them. The first sonication process is performed at a frequency in the range of from 0 to 20 kHz for a time period of from 0 to 5 minutes. The second sonication process is performed at a frequency in the range of from 20 to 200 kHz for a time period of from 0 to 15 minutes. Each of the first and second sonication processes is performed at a frequency for a time period such that no significant amount of defects that may affect the optical properties of the single walled carbon nanotubes is introduced.

In one embodiment, at least one optical property of the detergent encased single walled carbon nanotubes responds to a chemical property change in the solution of the detergent encased single walled carbon nanotubes. The single walled carbon nanotubes comprise semiconducting nanotubes, metallic nanotubes or a combination of them. The response of the at least one optical property of the detergent encased single walled carbon nanotubes to the chemical property change of the solution of the detergent encased single walled carbon nanotubes is more sensitively related to the semiconducting nanotubes than the metallic nanotubes in the solution of the detergent encased single walled carbon nanotubes. The response of the at least one optical property of the detergent encased single walled carbon nanotubes to the chemical property change of the solution of the detergent encased single walled carbon nanotubes is reversible.

In another aspect, the present invention relates to a biosensor responsive to a chemical property in an environment. The biosensor has a plurality of single walled carbon nanotubes forming an array and showing a dependence of the chemical property. The biosensor also has a processor coupled to the array of the plurality of single walled carbon nanotubes for processing the response of the plurality of single walled carbon nanotubes to the chemical property. At least one of the plurality of single walled carbon nanotubes is at least partially wrapped by one or more detergent molecules to make it a detergent encased single walled carbon nanotube. In one embodiment, the detergent comprises SDS, PSS or a combination of them.

In one embodiment, the chemical property is a hydrogen peroxide concentration in an environment, and the detergent encased single walled carbon nanotube is optically responsive to the hydrogen peroxide concentration in the environment.

In another embodiment, the at least one detergent encased single walled carbon nanotubes is further wrapped by one or more enzyme molecules to form a solution of detergent encased single walled carbon nanotubes with the enzyme. The hydrogen peroxide may be produced by an enzyme as one of the turnover products from a corresponding substrate.

In yet another embodiment, the chemical property is glucose concentration in an environment, the detergent encased single walled carbon nanotube is further wrapped by one or more glucose oxidase that may covert the glucose to hydrogen peroxide and gluconic acid, and the at least one detergent encased single walled carbon nanotube with glucose oxidase is optically responsive to hydrogen peroxide that is produced from the glucose by glucose oxidase in the environment.

In yet another aspect, the present invention relates to a surface modified single walled carbon nanotube that has a layer of carbon atoms forming a wall defining a cavity therein. The wall as formed has an outer surface and an inner surface, and a first end and an opposite, second end and at least one molecule non-covalently attached at least to one of the inner surface and the outer surface of the single walled carbon nanotube. The single walled carbon nanotube is at least partially surface modified with the at least one molecule to show an optical dependence of a chemical property of an environment. The at least one molecule comprises one of SDS, glucose oxidase, single stranded DNA, double-stranded DNA and PSS. The chemical property is one of pH value, hydrogen peroxide concentration, glucose concentration and ethanol concentration of the environment.

In a further aspect, the present invention relates to a method of detecting a chemical compound. The method includes the steps of providing a solution of surface modified single walled carbon nanotubes, associating the solution of surface modified single walled carbon nanotubes with the chemical compound, and detecting optically a chemical property change of the solution of surface modified single walled carbon nanotubes corresponding to the chemical compound so as to detect the chemical compound. In one embodiment, the detergent comprises SDS, PSS or a combination of them. The associating step comprises a step of forming a solution of the surface modified single walled carbon nanotubes and the chemical compound.

In one embodiment, the chemical compound comprises at least one of a base and acid, and the corresponding chemical property is pH of the solution of the surface modified single walled carbon nanotubes.

In another embodiment, the chemical compound is hydrogen peroxide, and the corresponding chemical property is hydrogen peroxide concentration in the solution of the surface modified single walled carbon nanotubes.

In yet another embodiment, the method further comprises the step of adding an amount of glucose oxidase to the solution of the surface modified single walled carbon nanotubes before the associating step so that at least one of the plurality of surface modified single walled carbon nanotubes is further wrapped by one or more glucose oxidase molecules. The chemical compound is glucose, and the corresponding chemical property is glucose concentration in the solution of the surface modified single walled carbon nanotubes with glucose oxidase. The glucose oxidase may convert glucose to hydrogen peroxide and gluconic acid, and the optically detecting step comprises a step of measuring the optical properties of the solution of the surface modified single walled carbon nanotubes with glucose oxidase responsive to the concentration of the hydrogen peroxide that is produced from glucose by glucose oxidase in the solution of the surface modified single walled carbon nanotubes with glucose oxidase.

In one embodiment, the method further comprises the step of adding an amount of enzyme to the solution of the surface modified single walled carbon nanotubes before the associating step so that at least one of the plurality of surface modified single walled carbon nanotubes is further wrapped by one or more of the enzyme molecules. The chemical compound is a substrate of the enzyme that is convertable to hydrogen peroxide as one of its turnover products by the enzyme, and the corresponding chemical property is the substrate concentration in the solution of the surface modified single walled carbon nanotubes with the enzyme.

In another embodiment, the chemical compound is iodine, and the corresponding chemical property is the iodine concentration in the solution of the surface modified single walled carbon nanotubes. In yet another embodiment, the chemical compound is oxidant, and the corresponding chemical property is the oxidant concentration in the solution of the surface modified single walled carbon nanotubes. In one embodiment, before the associating step, the method further comprises the steps of adding an amount of glucose oxidase to the solution of the surface modified single walled carbon nanotubes so that at least one of the surface modified single walled carbon nanotubes is further wrapped by one or more glucose oxidase molecules and adding an amount of iodide to the solution of the surface modified single walled carbon nanotubes with glucose oxidase. In one embodiment, the chemical compound is iodine that is produced in situ from the reaction of iodide with hydrogen peroxide, which is produced from glucose by the glucose oxidase, and the chemical property is the iodine concentration in the solution of the surface modified single walled carbon nanotubes.

In one aspect, the present invention relates to a method of optically detecting a chemical property change in a solution of surface modified single walled carbon nanotubes induced by sonication. The method includes the steps of providing a solution of surface modified single walled carbon nanotubes, performing a sonication on the solution of surface modified single walled carbon nanotubes, and detecting optically the response of the solution of surface modified single walled carbon nanotubes to a chemical property change of the solution of the solution of surface modified single walled carbon nanotubes induced by the sonication. In one embodiment, the detergent comprises SDS, PSS or a combination of them. The sonication is performed at a frequency in the range of from 20 to 200 kHz for a time period of from 0 to 200 minutes at a temperature in the range of from 0 to 100° C. The chemical property is pH in the solution of surface modified single walled carbon nanotubes. The chemical property change is corresponding to nitrous acid and nitric acid concentrations induced by sonication in the solution of surface modified single walled carbon nanotubes.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIG. 3. shows the pH dependence of SDS encased SWNTs wherein FIG. 3a shows the results for SDS encased pristine Tube@Rice SWNTs and FIG. 3b shows the results for SDS encased pristine HiPco SWNTs.

FIG. 4. shows the pH dependence of pristine SWNTs with coating of Triton X-100 and PVP wherein FIG. 4a shows the results for pristine Tube@Rice SWNTs with Triton X-100, FIG. 4b shows the results for pristine HiPco SWNTs with Triton X-100, FIG. 4c shows the results for pristine TubeRice SWNTs with PVP and FIG. 4d shows the results for pristine HiPco SWNTs with PVP.

DETAILED DESCRIPTION OF THE INVENTION

Figure 1:
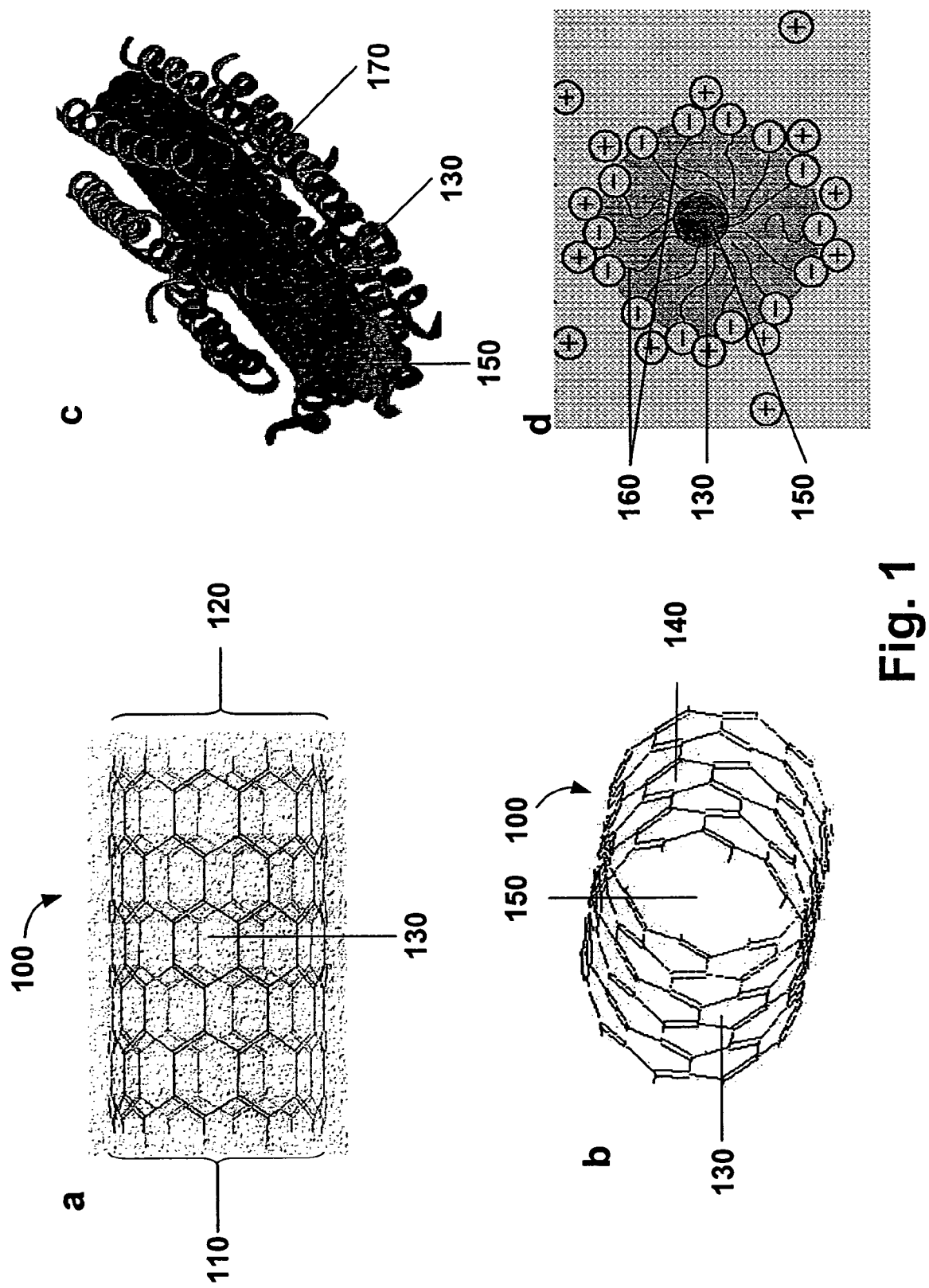
FIG. 1. shows (a) a side view of a single walled carbon nanotube; (b) a perspective view of a single walled carbon nanotube; (c) SWNT encased in polymeric material; and (d) SWNT encased in SDS.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "SDS" refers to sodium dodecyl sulfate.

As used herein, the term "PSS" refers to poly(sodium 4-styrenesulfonate).

As used herein, the term "PVP" refers to poly(vinylpyrrolidone).

As used herein, the term "GOx" refers to glucose oxidase.

As used herein, the term "SWNTs" refers to single walled carbon nanotubes.

As used herein, the term "ws-SWNTs" refers to water soluble single walled carbon nanotubes.

As used herein, the term "SDS-SWNTs" refers to SDS encased single walled carbon nanotubes.

As used herein, the term "GOx-SDS-SWNTs" refers to SDS encased single walled carbon nanotubes with glucose oxidase.

As used herein, the term "GOx-SDS-HiPco" refers to SDS encased HiPco single walled carbon nanotubes with glucose oxidase.

As used herein, the term "DNA-SWNT" refers to double stranded DNA encased single walled carbon nanotubes.

As used herein, the term "UV/vis/NIR" refers to ultra violate-visible-near infra red.

Overview of the Invention

Among other things, applicants have invented a method of detecting hydrogen peroxide with SDS encased single walled carbon nanotubes and corresponding biosensor(s). In one aspect, the present invention relates to near IR optical absorption (or reflection) methods for any forms of SWNTs, which can be isolated nanotubes, aggregated nanotubes or bundles. The SWNTs can be any SWNTs made by various techniques including HiPco and SWNTs made by a laser oven technique and by an arc discharge technique. Charge groups of modification species on the sidewall of SWNTs are required for pH sensing in aqueous solution. Without the charge groups' presence, SWNTs will not work for sensing pH changes.

In one embodiment, the present invention utilizes near IR optical absorption (or reflection) methods that use the intensity ratio $S_{11}/S_{22}$ of the first and second optical interband transitions of semiconducting SWNTs for sensing [14]. The $S_{22}$ band is less sensitive to environment changes so it can be used to serve as an internal reference. In applications, two wavelengths near the peak absorption of $S_{11}$ and $S_{22}$ coming from two near IR laser beams or from filtered light generated from a white light source can be adopted. No visible light is requested for excitation, which could be harmful for biological applications. From this discovery, a wide range of sensors can be designed by using a wide range of materials with charge groups such as amines, proteins and DNA. The negatively charged sulfonate groups of PSS and phosphate groups of DNA serve as sensing groups for pH. A device can be built by combining individual or bundled SWNTs with nanolasers [32, 33] or nano optical fibers [34] so the whole device can be a nanodevice.

Methods and Implementations

Without intent to limit the scope of the invention, additional exemplary methods and their related results according to the embodiments of the present invention are given below. Note that titles or subtitles may be used in the examples for convenience of a reader, which in no way should limit the scope of the invention. Moreover, certain theories maybe proposed and disclosed herein; however, in no way they, whether they are right or wrong, should limit the scope of the invention so long as the present invention is practiced without regard for any particular theory or scheme of action.

EXAMPLES

Example 1

SDS Encased SWNTs and their Properties
Preparation of SDS Encased SWNTs

In one embodiment, about 2.4 mg pristine SWNTs (such as HiPco or Tube@Rice) were weighed on a TGA microgram balance and placed in a 10 mL test tube with 5 mL 1 wt % SDS aqueous solution. In an ultrasonic bath (Branson Model 1510, 42 kHz), a mild (first) sonication was applied for 1-3 minutes to disperse HiPco nanotubes and then the mixture was vigorously sonicated (a second sonication) for about 1 minute. Short sonication time was applied because the optical properties of HiPco SWNTs are very sensitive to sonication. The resulting mixture was centrifuged (Sargent-Welch Scientific Co.) for about 1 hour. 0.8 mL of the top portion of the centrifuged sample was decanted and diluted with the SDS solution to make a solution of SDS encased SWNTs (SDS-SWNTs) for subsequent analysis. FIG. 1$d$ illustrates the outer surface 130 of an SDS-SWNT iwrapped with SDS molecules 160.

Figure 2:
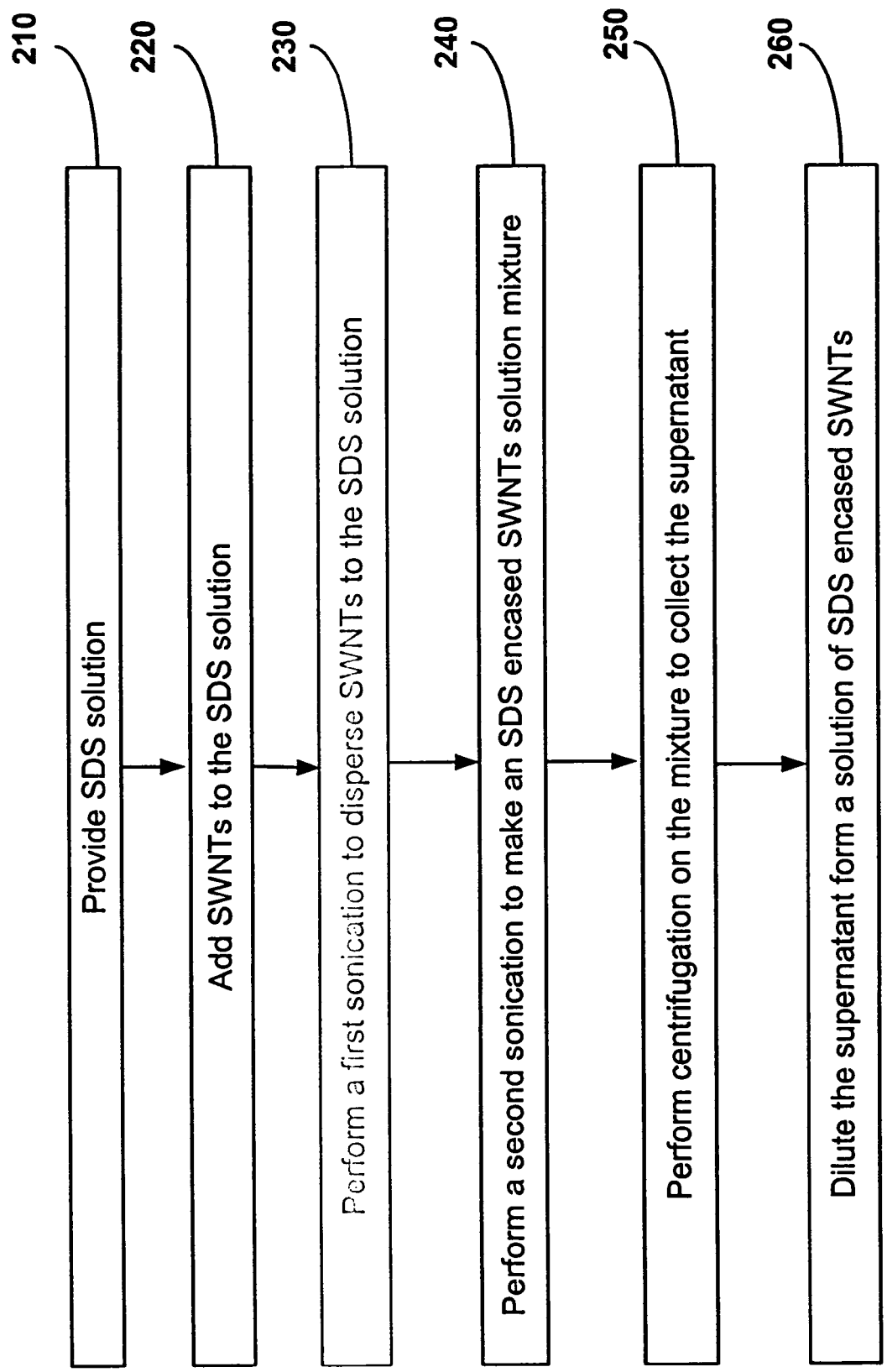
FIG. 2. illustrates schematically a process to synthesize SDS encased SWNTs.

A process to synthesize SDS-SWNTs is schematically illustrated in FIG. 2. At step 210, an SDS solution is provided. At step 220, SWNTs are added into the SDS solution. At step 230, a first sonication is performed to disperse SWNTs to the SDS solution at a frequency in the range from 0 to 20 kHz for a time period from 0 to 5 minutes. At step 240, a second sonication is performed to make an SDS encased SWNTs solution mixture at a frequency in the range from 20 to 200 kHz for a time period from 0 to 15 minutes. At step 250, the solution mixture is centrifuged and only the supernatant that contains SDS-SWNTs is collected. At step 260, the supernatant is diluted to make a solution of SDS-SWNTs suitable for subsequent optical measurements.

SDS Encased SWNTs Response to pH Change

Figure 3:
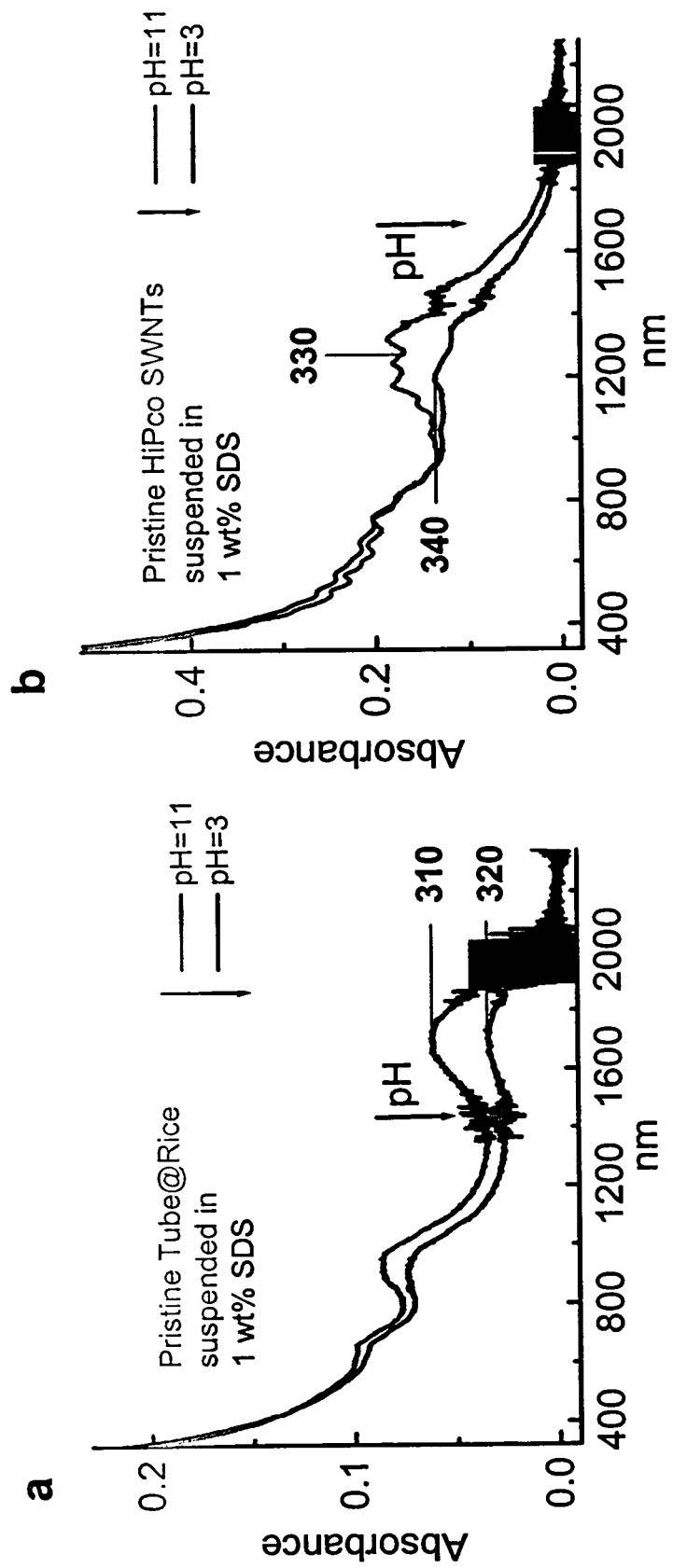

According to one embodiment of the present invention, the optical properties of SDS encased SWNTs are responsive to pH change in their environment. As illustrated in FIG. 3$a$, at pH 11, the UV/vis/NIR absorption of SDS encased pristine Tube@Rice SWNTs has a prominent peak 310 with wavelength range from 1400 nm to 2000 nm. The intensity of the peak 320 corresponding to the pH in the solution at 3 is significantly lower than the intensity of the peak 310 at pH 11. Similar results were observed for SDS encased pristine HiPco SWNTs as illustrated in FIG. 3$b$. The UV/vis/NIR absorption of SDS encased pristine HiPco SWNTs has a prominent peak 330 with wavelength range from 1000 nm to 1600 nm. The intensity of the peak 340 corresponding to the pH in the solution at 3 is significantly lower than the intensity of the peak 330 at pH 11.

SWNTs Encased with Other Detergents

Figure 4:
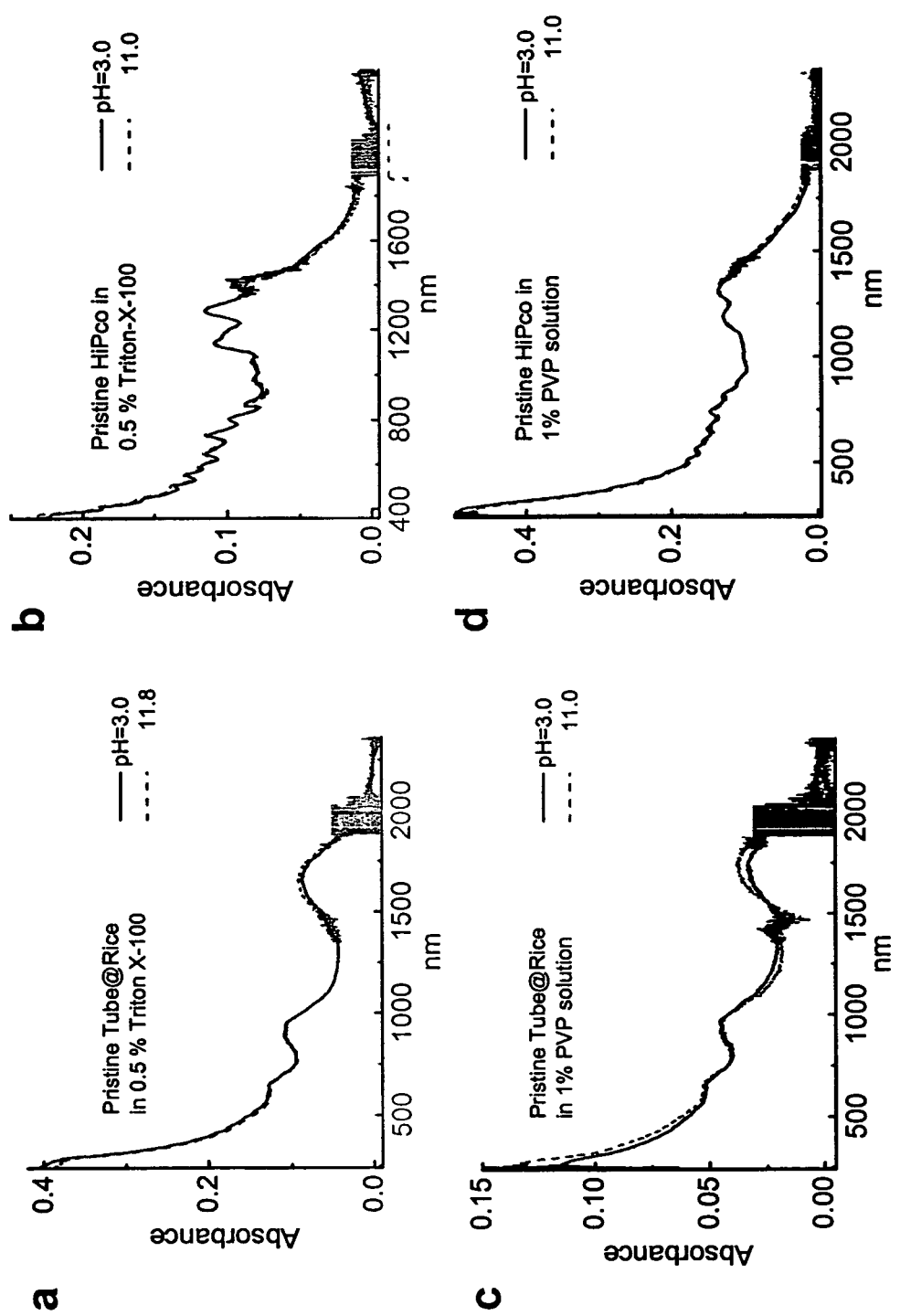
Figure 5:
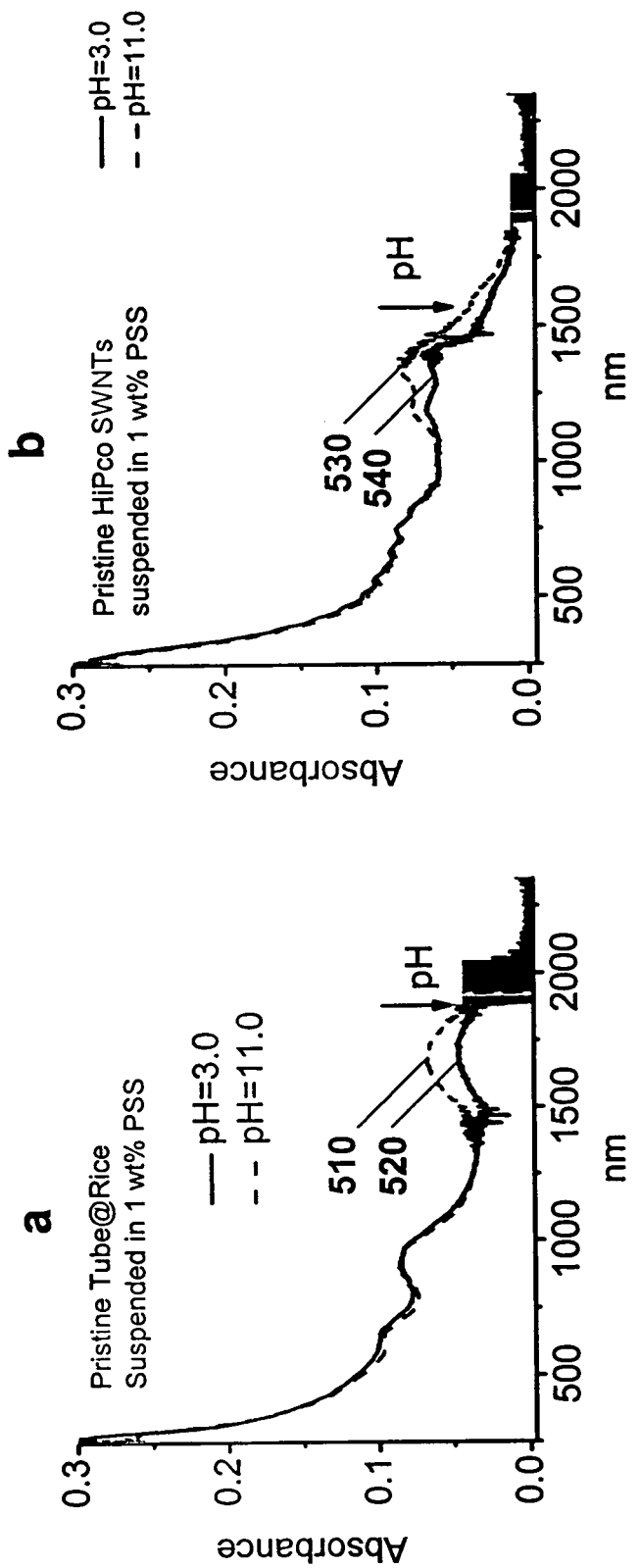
FIG. 5. shows the pH dependence of pristine SWNTs with coating of poly(sodium 4-styrenesulfonate (PSS) wherein FIG. 5a shows the results for pristine Tube@Rice SWNTs with PSS and FIG. 5b shows the results for pristine HiPco SWNTs with PSS.

Charge groups are crucial for pH sensing of SWNTs. Three different kinds of detergents, sodium dodecyl sulfate (SDS) with charge groups, Triton X-100 and poly(vinylpyrrolidone) (PVP) without charge groups are chosen as coating materials for SWNTs. As illustrated in FIG. 4$a$-$d$, respectively, the pristine Tube@Rice and HiPco SWNTs are insensitive to pH changes under the coating of Triton X-100 and PVP polymer because the spectra obtained at pH 3 or 11 are nearly super imposable to each other. However, as shown in FIGS. 3$a$ and 3$b$, respectively, the pristine Tube@Rice and HiPco SWNTs show pH-dependence after encased with SDS. The importance of charge group in SWNTs pH sensing has been confirmed by using other materials with charge groups such as poly(sodium 4-styrenesulfonate (PSS, MW ~70,000). As illustrated in FIG. 5$a$, at pH 11, the UV/vis/NIR absorption of SDS encased pristine Tube@Rice SWNTs has a prominent peak 510 with wavelength range from 1400 nm to 2000 nm. The intensity of the peak 520 corresponding to the pH in the solution at 3 is significantly lower than the intensity of the peak 510 at pH 11. Similar results were observed for SDS encased pristine HiPco SWNTs as illustrated in FIG. 5$b$. The UV/vis/NIR absorption of SDS encased pristine HiPco SWNTs has a prominent peak 530 with wavelength range from 1000 nm to 1600 nm. The intensity of the peak 540 corresponding to the pH in the solution at 3 is significantly lower than the intensity of the peak 530 at pH 11.

Figure 6:
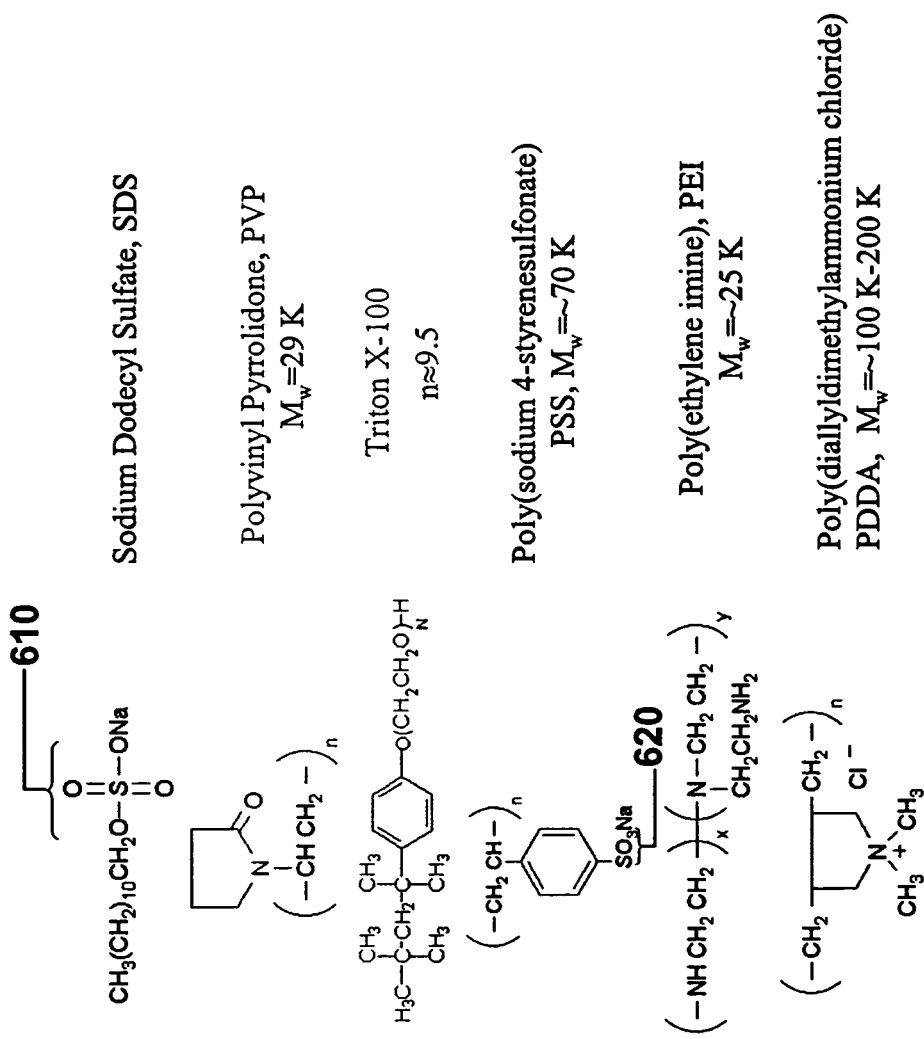
FIG. 6. illustrates the chemical structure of the polymers used as models for pH sensing according to one embodiment of the present invention.

FIG. 6 listed the chemical structure of some polymers used as models for pH sensing according to the present invention. SDS and PSS have negatively charged sulfate 610 and sulfonate 620 group, respectively.

The results indicate that the negatively charged groups on the coating materials are necessary for SWNT-based pH sensing [14, 30, 48]. The pH range for observation of the optical changes of SWNTs may differ depending on the encasing material used and its isoelectric point or equilibrium constants, which changes the pH range for protonation and deprotonation. To achieve the optimal pH sensing range, other detergents that are analogs of or structurally similar to SDS or PSS can be used. Detergents with negative charge may also be used together as a mixture.

Pristine SWNTs do not respond to pH changes when they are dispersed in water by using a neutral polymer surfactant Triton X-100 wrapping. The observation of no changes in the electronic band structure $S_{11}$ of pristine SWNTs when they are exposed in neutral polymer surfactant environments suggests an important application for using those polymers as protecting regents when no perturbation for pristine SWNTs is required in aqueous solution.

SDS Encased SWNTs Response to Sonication in Aerated Water

Figure 7:
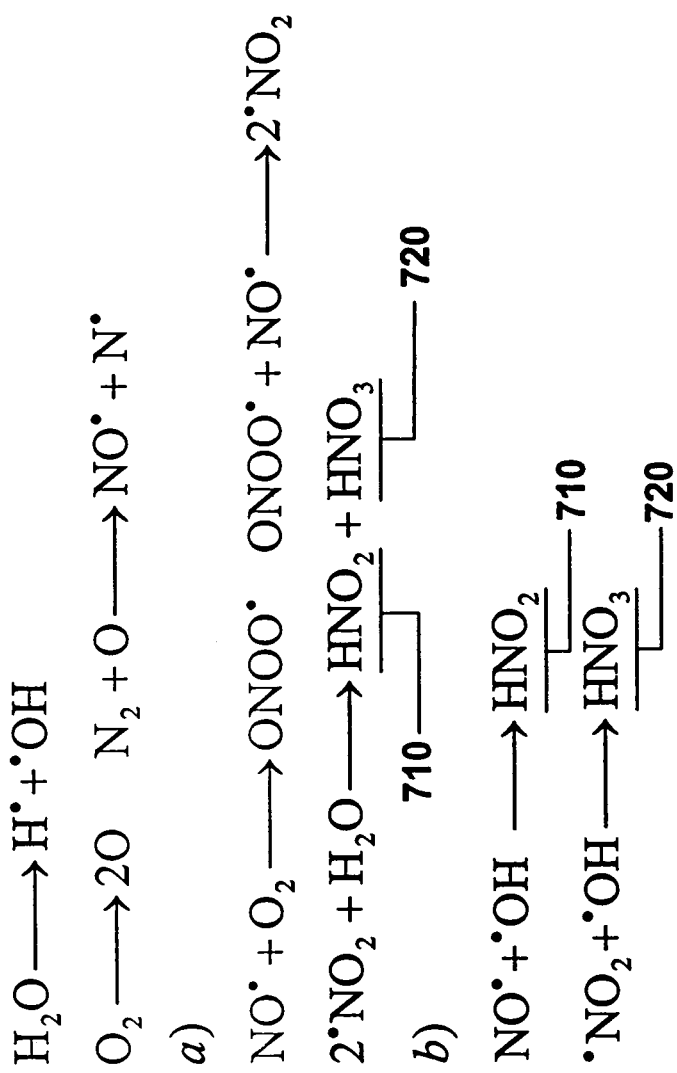
FIG. 7. shows a possible mechanism of the formation of nitrous acid and nitric acid in aerated water under sonication.

Vigorous ultrasonication is often employed to enhance the dissolution of SWNTs in SDS aqueous solution, by encasing individual nanotubes in SDS. Such isolated nanotubes are crucial for separating metallic and semiconducting nanotube [20]. However, the sonication of aerated water is a quite complex process that generates various reactive intermediates [36-41]. As illustrated in FIG. 7, nitrous acid 710 ($HNO_2$) and nitric acid 720 ($HNO_3$) are formed in aerated water under sonication. The effects of sonication on the optical properties of SWNTs are further studied.

Experimental Examples

Pristine HiPco SWNTs, with tube diameters between 0.7 and 1.1 nm and a length distribution from several hundred nanometers to a few micrometers, were purchased from Carbon Nanotechnology, Inc [23]. SDS was purchased from Sigma-Aldrich with purity >99%. HiPco solutions in 1 wt % SDS in $H_2O$ were prepared using methods known to people skilled in the art [23]. Briefly, about 2.4 mg pristine HiPco SWNTs were weighed on a microgram-scaled balance in a TGA and placed in a 10 mL test tube with 5 mL 1 wt % SDS aqueous solution. An ultrasonic bath (Branson Model 1510R-

MT, 42 kHz with rated power output of 70 W) was used to disperse HiPco SWNTs in SDS solutions. The starting ultrasonic bath temperature was room temperature and it may increase up to 40° C. under prolonged sonication. The mixture in the test tube was sonicated for about 4 minutes and then was centrifuged (Sargent-Welch Scientific Co.) for 15 minutes. About 2 mL of the top portion of the centrifuged sample was decanted and diluted with 6 mL SDS solution. Two SWNT solution samples with volumes of 0.5 and 5 mL were transferred into two 10 mL test tubes for further sonication studies. 0.5 mL is the minimum volume that could be used for optical absorption measurements and 5 mL is suitable for pH measurements. It was observed that the effects of sonication on SWNT solutions were related to the solution volume. The 0.5 mL solution required much longer sonication time (up to 65.5 minutes) to exhibit optical property changes similar to those in the 5 mL solution (0-5 minutes). For the sake of clarity, the results reported here are mainly for the 5 mL SWNT solution, only some results of 0.5 mL SWNT solutions were included. UV/vis/NIR absorption spectra were measured by using a Perkin-Elmer UV/Vis/NIR spectrometer. A quartz cell of 1 mm path length was used for holding solutions. The absorption spectra of the samples after different sonication times were recorded and the SDS solution was used as a reference for background subtraction. An Orion Model 420 pH meter with a Ag/AgCl referenced Orion pH glass electrode was used to measure the pH of 5 mL samples of SDS solution after sonication for various times. All measurements were conducted at room temperature.

Figure 8:
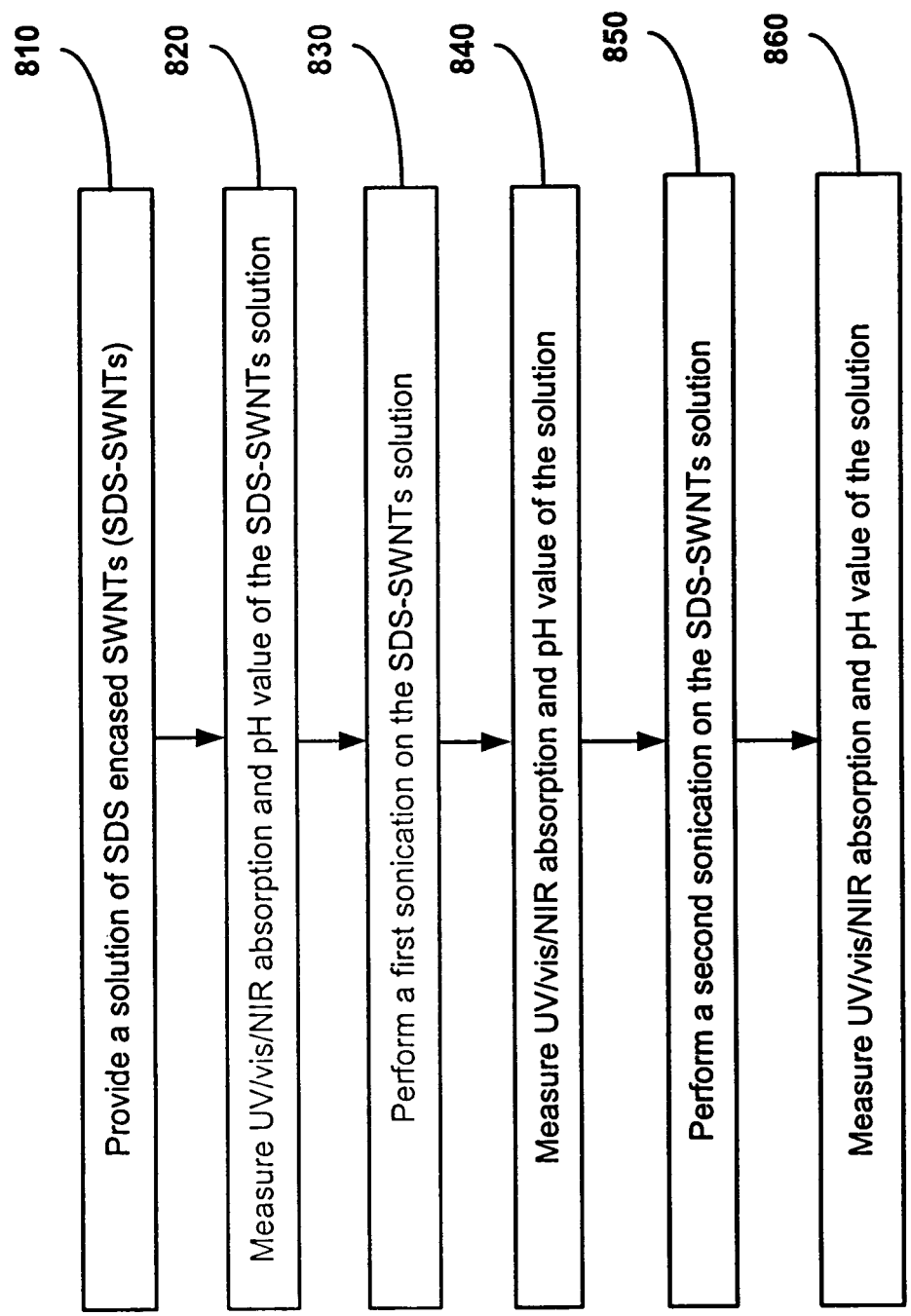
FIG. 8. is a flowchart for a process to measure the optical response of SDS-SWNTs to pH change induced by sonication according to one embodiment of the present invention.

The processes to measure the optical response of SDS-SWNTs to pH change induced by ultrasonication is schematically illustrated in FIG. 8. At step 810, a solution of SDS-SWNTs is provided. At step 820, the UV/vis/NIR absorption and pH value of the solution are measured as base values. A first sonication is performed at step 830 on the SDS-SWNTs solution at a frequency in the range of from 20 to 200 kHz for a time period of from 0 to 200 minutes at a temperature in the range of from 0 to 100° C. The UV/vis/NIR absorption and pH value of the solution is measured at step 840 to find out the changes in absorption of SDS-SWNTs and in pH induced by the first sonication. A second sonication is performed at step 850 on the SDS-SWNTs solution at a frequency in the range of from 20 to 200 kHz for a time period of from 0 to 200 minutes at a temperature in the range of from 0 to 100° C. The UV/vis/NIR absorption and pH value of the solution is measured at step 860 to find out the changes in absorption of SDS-SWNTs and in pH induced by the second sonication. The sonication and measurement steps may be repeated until all desired data is collected.

Results and Discussion

Figure 9:
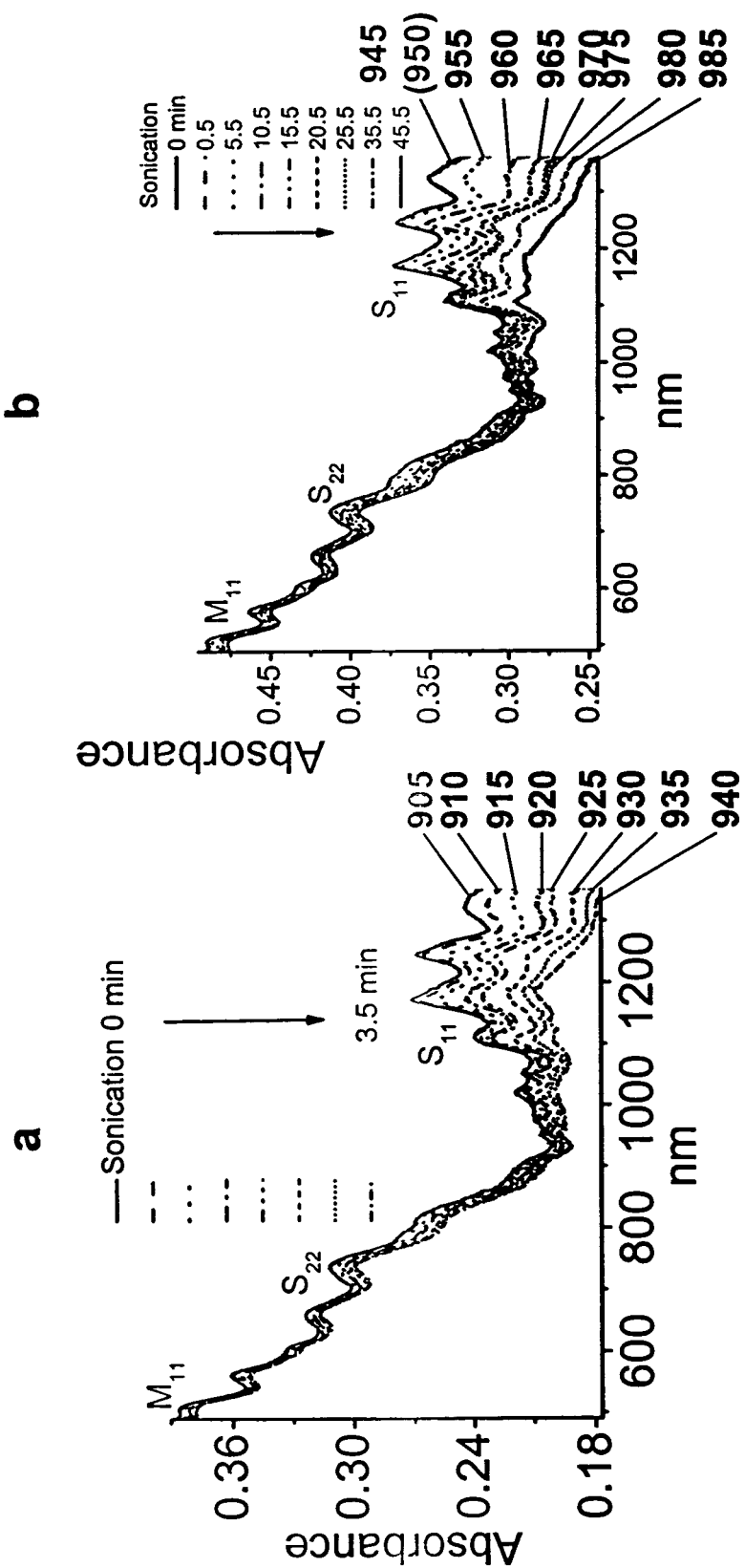
FIG. 9. shows the absorption spectra of (a) a 5 mL HiPco SWNT solution; and (b) a 0.5 mL HiPco SWNT solution after different sonication times according to one embodiment of the present invention.

FIG. 9a shows the absorption spectra of the 5 mL SWNT solution after sonication for times ranging from 0 to 3.5 minutes, with 0.5 minutes increments. Spectra 905, 910, 915, 920, 925, 930, 935, and 940 correspond to sonication time points 0, 0.5, 1.0, 1.5, 2.0, 2.5, 3.0, and 3.5 minutes, respectively. The absorption bands at >830 nm come from the $S_{11}$ transitions of semiconducting SWNTs with different diameters while the bands at <830 nm belong to the interband transitions of the first pair ($M_{11}$) of metallic nanotubes and the second pair ($S_{22}$) of semiconducting nanotubes [5a, 14, 21, 23-25, 29, 45]. The intensity of the $S_{11}$ bands decreases with sonication time while sonication has less impact on the $M_{11}$ and $S_{22}$ bands. Similar results were observed with 0.5 mL SWNT solution as illustrated in FIG. 9b. Spectra 945, 950, 955, 960, 965, 970, 975, 980, and 985 correspond to sonication time points 0, 0.5, 5.5, 10.5, 15.5, 20.5, 25.5, 35.5, and 45.5 minutes, respectively. Hardly any change in the spectra was observed after 0.5 minutes sonication as it is shown that spectrum 945 from 0 minute measurement, i.e., no sonication, superimposed with spectrum 950 from 0.5 minutes measurement. The 0.5 mL solution required much longer sonication time (up to 65.5 minutes) to exhibit optical property changes similar to those in the 5 mL solution (0-5 minutes). The observed changes in the spectra after the sonication are very similar to pH induced spectral changes observed in Refs. 14, 18, and 24, an indication that the pH of the SWNT solution may drift into a more acidic range with sonication due to the formation of nitric and nitrous acids by sonication [36-41].

Figure 10:
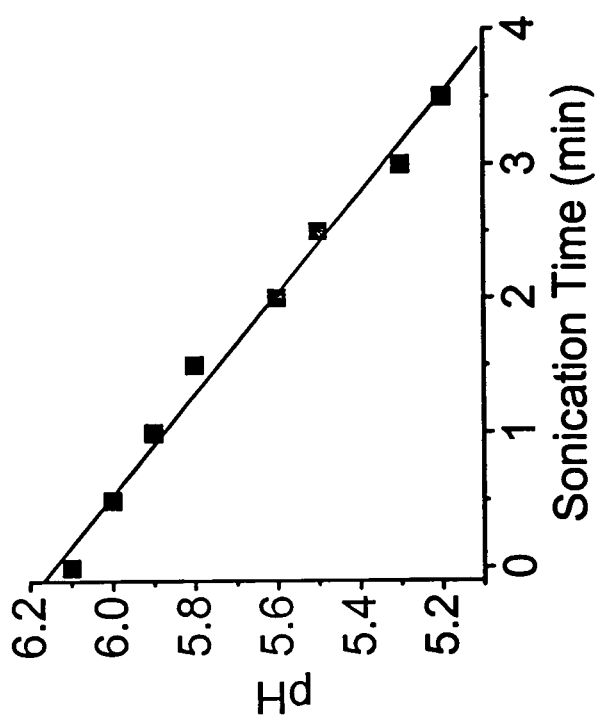
FIG. 10. shows the changes in pH of an SDS solution as a function of sonication time according to one embodiment of the present invention.
Figure 11:
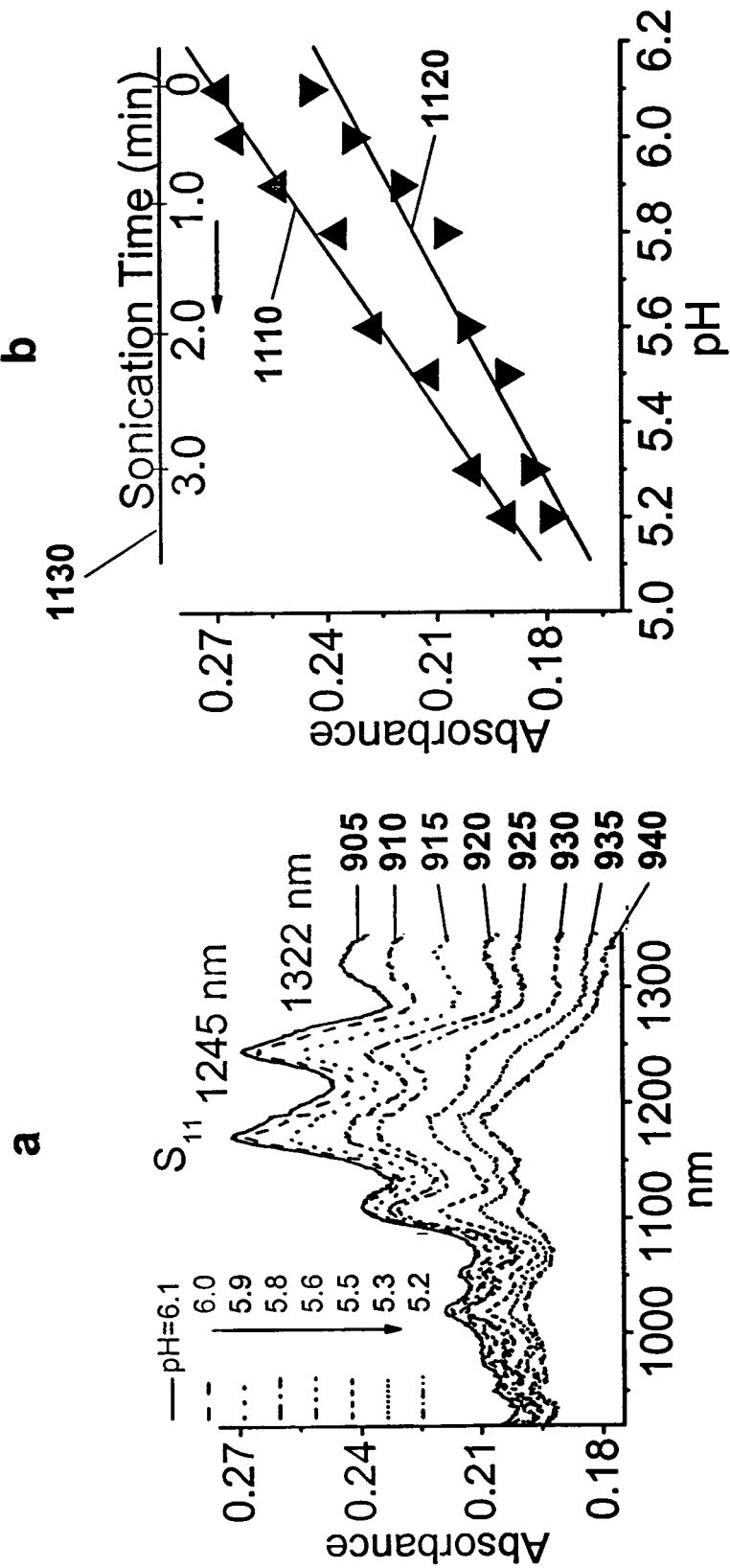
FIG. 11. shows (a) an enlarged absorption spectra showing the details in the $S_{11}$ region with corresponding pH changes induced by sonication of FIG. 9a and (b) absorbance dependence of two $S_{11}$ peaks of the HiPco SWNT solution on different pHs induced by sonication.

To confirm that sonication induces changes in pH of the SWNT solution, a control experiment was conducted for direct pH measurements under the same sonication conditions used for the SWNT solution in FIG. 9a. The measured pH values are shown in FIG. 10, where a substantially linear relationship is observed between sonication-induced pH and sonication time. Based on the result in FIG. 10, the $S_{11}$ region in FIG. 9a is enlarged as shown in FIG. 11a, with corresponding sonication-induced pH changes. Spectra 905 (0 minute sonication), 910 (0.5 minute sonication), 915 (1.0 minute sonication), 920 (1.5 minute sonication), 925 (2.0 minute sonication), 930 (2.5 minute sonication), 935 (3.0 minute sonication), and 940 (3.5 minute sonication) correspond to pH values of 6.1, 6.0, 5.9, 5.8, 5.6, 5.5, 5.3, and 5.2, respectively. The sonication reduces the pH by only about 1 unit while significant spectral changes in the $S_{11}$ bands simultaneously occur, suggesting that SDS-encased SWNTs may be used as a sensor for detection of sonolysis-induced pH changes with high sensitivity [30, 14]. To further check the sonication-induced pH decrease, pure water and SDS solutions in 1, 3, 5, 7, and 9 wt % were also examined with 5 min sonication. A pH decrease in all solution samples was observed, indicating that it is a general phenomenon for aerated water [36-41]. In addition, after mixing an SWNT solution (the top portion of the centrifuged SWNT sample with well-reserved $S_{11}$ band intensities) with a 1 wt % SDS solution whose pH decreased to 5.0 after sonication, a decrease in $S_{11}$ band intensities was also observed. This result further indicates that the sonication-induced pH changes in the solution may cause the spectral changes.

To further elucidate the relationship between the sonication-induced pH changes and the interband intensity of $S_{11}$ bands, two representative $S_{11}$ bands at 1245 nm and 1322 nm corresponding to semiconducting nanotubes (8, 7) and (9, 7) with diameters 1.03 and 1.1 nm, respectively were selected [29]. The 1245 nm band may also overlap with bands from (9, 5), (10, 3) and (10, 5) nanotubes, and the 1322 nm band overlaps with bands from (12, 4) and (13, 2) nanotubes [25, 48]. The intensity of the two bands is plotted as a function of sonication-induced pH changes as illustrated in FIG. 11b. There are nearly linear relationships between the $S_{11}$ band 1245 NM (1110) and 1322 nm (1120) intensities and sonication-induced pH changes. The top axis 1130 shows the corresponding sonication time increasing from right to left.

Figure 12:
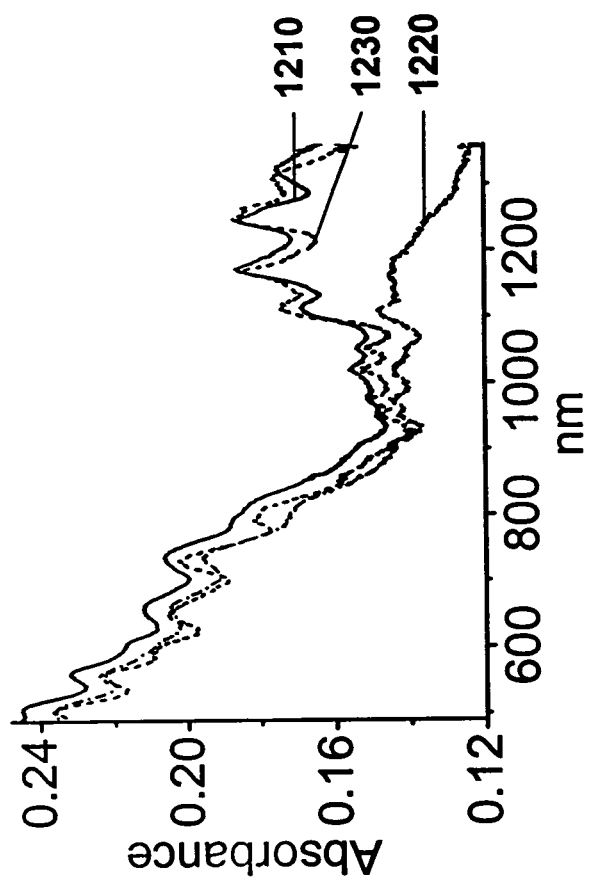
FIG. 12. shows the absorption spectra of a 0.5 mL HiPco SWNT solution sonicated for 0.5 minutes, 65.5 minutes, and the recovery of the $S_{11}$ peaks after the pH is adjusted to 10.

It has been observed that the $S_{11}$ bands reversibly respond to pH changes [14, 18, 24, 25, 48]. It was therefore unsurprising that increasing the pH recovered $S_{11}$ bands that were suppressed by sonication. FIG. 12 shows absorption spectra of a 0.5 mL HiPco SWNT solution sonicated for 0.5 minutes (1210) and 65.5 minutes (1220). After addition of 0.1 M NaOH to adjust the pH of the solution to 10, absorption of the $S_{11}$ bands were fully restored (1230). Lowering the solution pH to 5.0 by adding 0.1 M HCl suppresses the $S_{11}$ bands again, similar to other observations of SDS-encased SWNTs [24].

The sonication of aerated water is a complex process involving various reactive intermediates [36-41]. The above results suggest that the acids generated by sonication may be responsible for the observed spectral changes. There is also a consideration that degassing $CO_2$ during sonication and redissolution of $CO_2$ after sonication may cause the observed pH changes. A pH calculation was performed on water in equilibrium with $CO_2$ (assuming a maximum $CO_2$ concentration of 400 ppm) and it was found that the lowest pH attributable to atmospheric $CO_2$ was about 5.65 [49]. Therefore atmospheric $CO_2$ cannot bring the pH down to 5.2 as shown in FIG. 10. The observed decrease in pH by sonication is mainly due to nitric acid and nitrous acid produced from the sonolysis of $O_2$, $N_2$ and $H_2O$ as illustrated in FIG. 7 [36-41]. The protonation of SDS-encased SWNTs induced by these acids depletes the valence band electrons of semiconducting SWNTs and so decreases the $S_{11}$ band intensity [5a, 14]. However, the observed full restoration of the $S_{11}$ bands by addition of NaOH also indicates that the actual lattice structure of the SWNTs is undisrupted after sonication.

Figure 13:
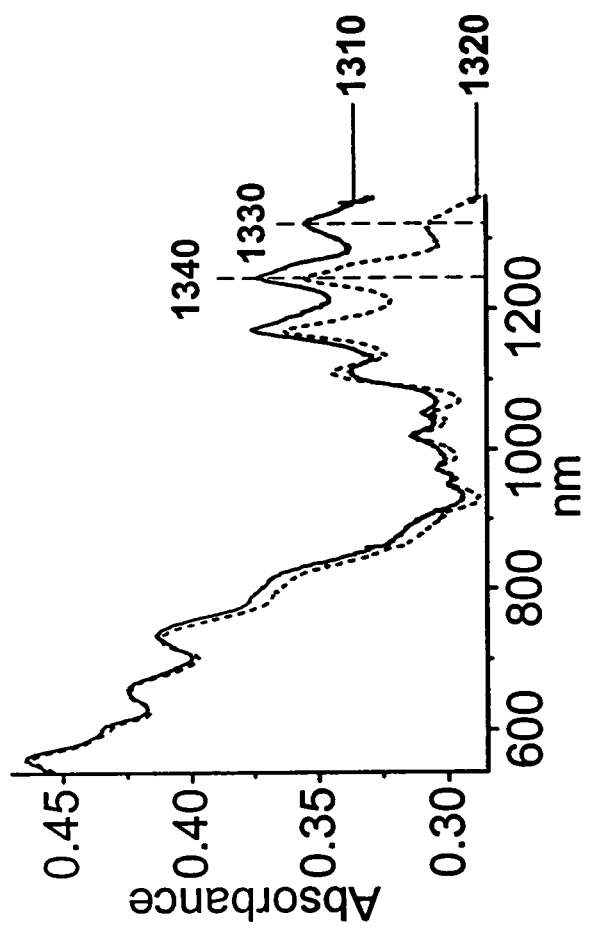
FIG. 13. shows the absorption spectra of a 0.5 mL SDS-encased HiPco SWNT solution in a pH 6.0 phosphate buffer (0.05M) before and after an extensive sonication.

To further examine whether the pH changes are the dominant factor in the optical changes of SWNTs, an SDS-encased SWNTs in a 50 mM phosphate buffer of pH 6.0 was also sonicated. The pH changes in a buffer should be small and only subtle changes in optical absorption of sonicated SWNTs are expected under these conditions. The results are shown in FIG. 13. Spectra before (1310) and after (1320) 35.5 minutes sonication show that prolonged sonication causes no significant spectral changes for most absorption bands except the 1322 nm band (1330), respectively. The intensity of the 1245 nm band (1340) also decreases slightly. The result is significantly different from non-buffered solutions as shown in FIGS. 9a and 9b, suggesting that the spectral changes of SWNTs under sonication may be mainly caused by a pH-related process. Other possible intermediates such as oxidizing species NO and $H_2O_2$ [36-41] may contribute to the spectral suppression through electron withdrawal from SWNTs. However, as shown in FIG. 13, their contribution is more distinct for the larger-diameter nanotubes such as the (9, 7) nanotubes at 1322 nm and is less significant for the smaller-diameter nanotubes with bands <1170 nm without the involvement of the sonication-induced pH decease.

Conclusions

Ultrasonication is a necessary process to make single-walled carbon nanotubes (SWNTs) soluble in aqueous solution with surfactants such as sodium dodecyl sulfate (SDS). It is observed that sonication induced pH changes suppress the optical transitions of the first interband transition pair ($S_{11}$) in the density of states of semiconducting SWNTs while other possible intermediates induced by sonication contribute less significantly to the observed spectral changes without the involvement of sonication-induced pH decrease. The suppressed $S_{11}$ peaks can be restored by adding basic solution, suggesting that the lattice structure of SWNTs is undisrupted by the sonication used here. The absorbance of $S_{11}$ peaks shows a nearly linear relationship with sonication induced pH changes in the narrow pH range of 5.2 and 6.1. The results indicate that SDS-encased SWNTs may be used as an indicator for sonolysis-related applications.

Additionally, the results obtained suggest that to avoid sonication-induced optical changes of SWNTs, sonication can be done in a buffer with pH >6.0 or by making the SDS solution to more basic such as pH 10 as is usually done in sonication-related HiPco research. Example 2 SDS encased SWNTs for Hydrogen Peroxide Sensing SDS Encased SWNTs Respond to Hydrogen Peroxide Concentration Many enzyme-catalyzed reactions yield hydrogen peroxide ($H_2O_2$) as a product [52]. Although $H_2O_2$ has been used in purification of SWNTs [7a], it is understood that no research is known to address its interaction with SWNTs for optical sensing. In view of recent great progress in the development of nanolasers [33], nanowaveguides [53] and optical nanofibers [34], there are urgent needs to develop new nanostructural materials that can utilize these nano light sources for optical nanosensors. Here, a representative ws-SWNT system, namely HiPco SWNTs encased in the surfactant sodium dodecyl sulfate (SDS) is used to study the SWNT solution reaction with $H_2O_2$.

Experimental Examples

Raw HiPco SWNTs (purity ~95 atm %) were purchased from Carbon Nanotechnologies, Inc [23]. The nanotube diameters range from 0.7 to 1.1 nm and are from several hundred nanometers to a few micrometers long [23]. The reagents SDS (>99% pure), $H_2O_2$ (30 wt %) and catalase (EC 1.11.1.6, 1870 units/mg) were from Sigma-Aldrich. Nanotube solutions in 1 wt % SDS in $H_2O$ were prepared using a procedure known to people skilled in the art [23]. Briefly, in a typical experiment, about 2.4 mg pristine HiPco SWNTs were weighed on a microgram-scaled balance in a TGA and placed in a 10 mL test tube with 5 mL 1 wt % SDS aqueous solution. Mild sonication was applied in an ultrasonic bath (Branson Model 1510, 42 kHz) for 1-3 minutes to disperse HiPco nanotubes, and then the mixture was vigorously sonicated for about 1 minute. Longer sonication time was avoided since the optical features of SWNTs may be suppressed by prolonged sonication. The resulting mixture was centrifuged (Sargent-Welch Scientific Co.) for 1 hour, and then 0.8 mL of the supernatant was decanted and diluted with the SDS solution. About 0.13 mL of the diluted HiPco solution was mixed with an equal amount of pH 6.0 phosphate buffer (50 mM) and transferred into a 1 mm quartz cell. The resulting solution had an optical absorbance of about 0.3 at 1245 nm at a HiPco concentration of about 0.1 mg/ml. A series of such solutions were prepared with $H_2O_2$ concentrations ranging from 0 to 200 ppm. The time-dependent optical absorption of the solutions was measured at room temperature in 1 mm quartz cells using a Perkin-Elmer Lamda 19 UV/Vis/NIR spectrometer [54]. All samples were prepared in pH 6.0 buffer solutions to eliminate possible pH induced spectral changes. SDS solutions in pH 6.0 buffers without HiPco nanotubes were used for absorption background subtraction. For reversibility experiments with pH tuning, 0.1 M NaOH and 0.1 M HCl solutions were used for pH titrations. An Orion Model 420 pH meter with a Thermo Electron Orion micro pH glass electrode was used to measure the pH of the HiPco nanotube solution samples.

Figure 14:
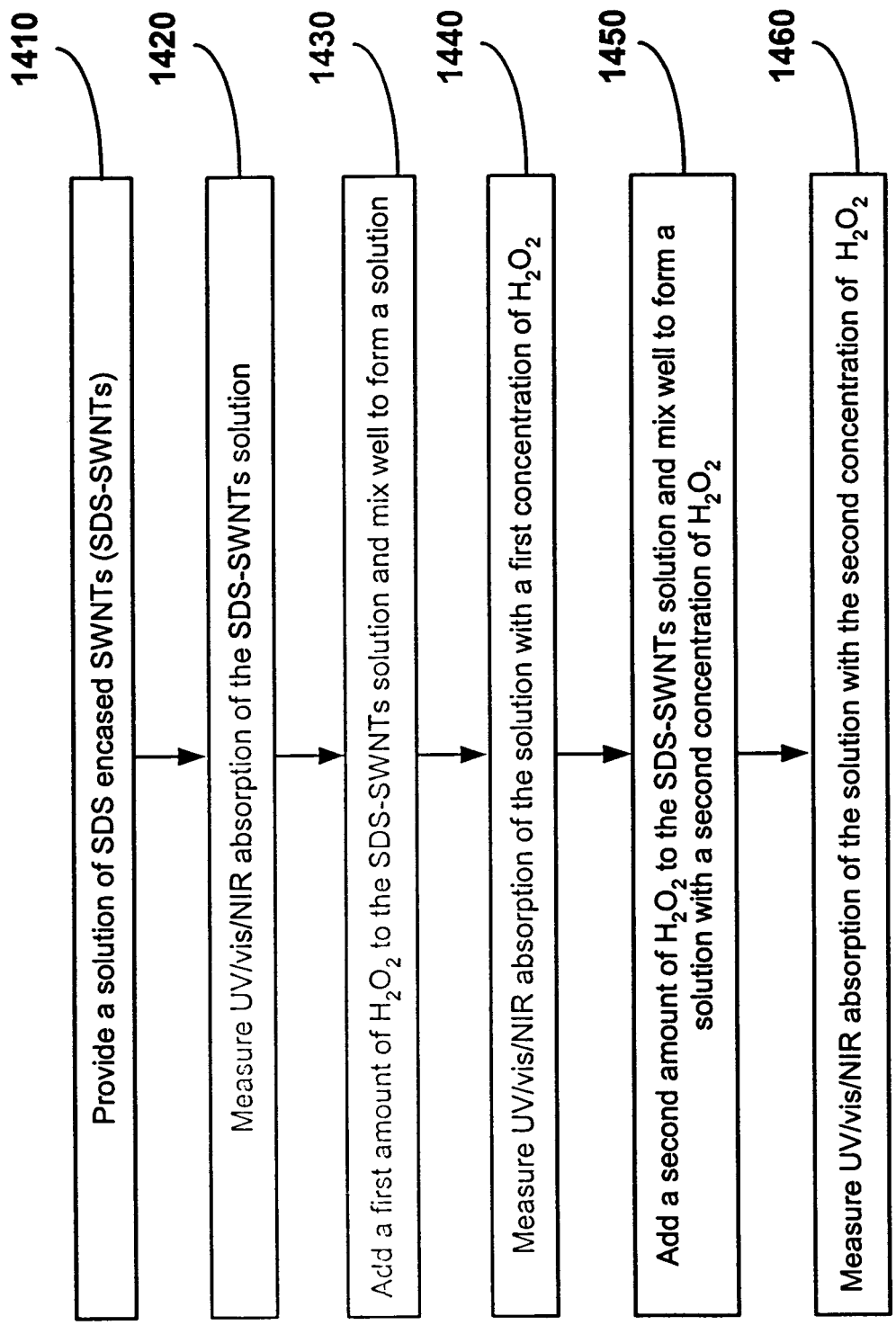
FIG. 14. is a flowchart for a process to measure the optical response of SDS-SWNTs to $H_2O_2$ at different concentrations according to one embodiment of the present invention.

The process to measure the optical response of SDS-SWNTs to $H_2O_2$ at different concentrations is schematically illustrated in FIG. 14. At step 1410, a solution of SDS-SWNTs is made or provided. At step 1420, the UN/vis/NIR absorption of the SDS-SWNTs solution is measured as a baseline. At step 1430, a first amount of $H_2O_2$ is added to the SDS-SWNTs solution and mix well to form a solution with a first concentration of $H_2O_2$. UV/vis/NIR absorption of the solution is then measured at 1440 to find out the change in absorption of SDS-SWNTs induced by the addition of the first amount of $H_2O_2$. At step 1450, a second amount of $H_2O_2$ is added to the SDS-SWNTs solution and mix well to form a solution with a second concentration of $H_2O_2$. UV/vis/NIR absorption of the solution is measured at 1460 to find out the change in absorption of SDS-SWNTs induced by the addition of the second amount of $H_2O_2$. The process of $H_2O_2$ addition and subsequent measurement may be repeated until all the desired data are obtained.

Figure 15:
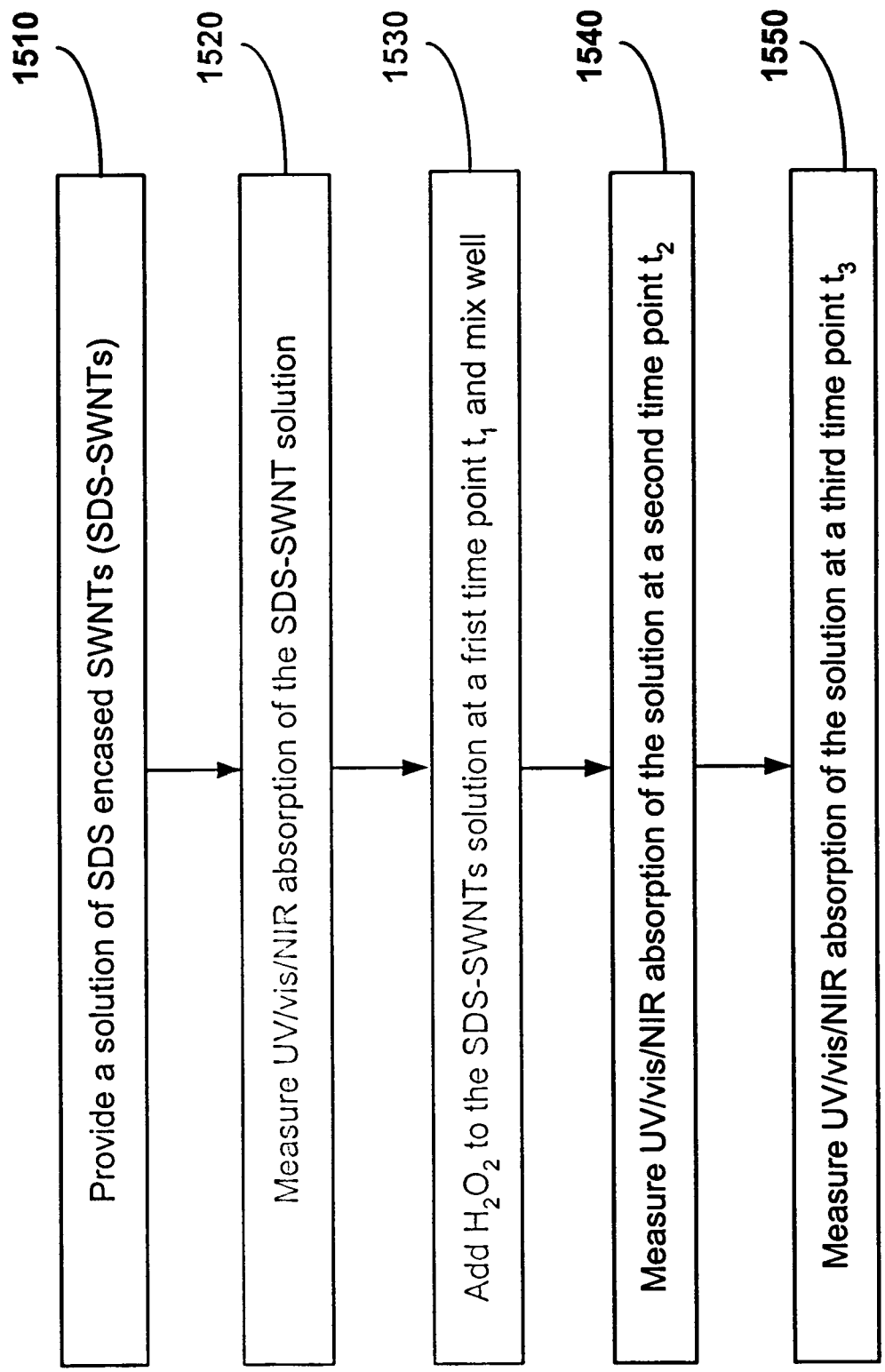
FIG. 15. is a flowchart for a process to measure the optical response of SDS-SWNTs to $H_2O_2$ at different time points.

Similarly the process to measure the optical response of SDS-SWNTs to $H_2O_2$ at different time points is schematically illustrated in FIG. 15. At step 1510, a solution of SDS-SWNTs is made or provided. At step 1520, the UN/vis/NIR absorption of the SDS-SWNTs solution is measured as a baseline. At step 1530, an amount of $H_2O_2$ is added to the SDS-SWNTs solution at time point $t_1$ and mix well to form a solution with a fixed concentration of $H_2O_2$. UV/vis/NIR absorption of the solution is measured at time point $t_2$ (1540) to find out the change in absorption of SDS-SWNTs induced by the addition of the $H_2O_2$. UV/vis/NIR absorption of the solution is measured at time point $t_3$ (1550) to find out further change in absorption of SDS-SWNTs induced by the addition of the $H_2O_2$. The process of time point measurement is repeated until all desired data are obtained.

Results and Discussion

Figure 16:
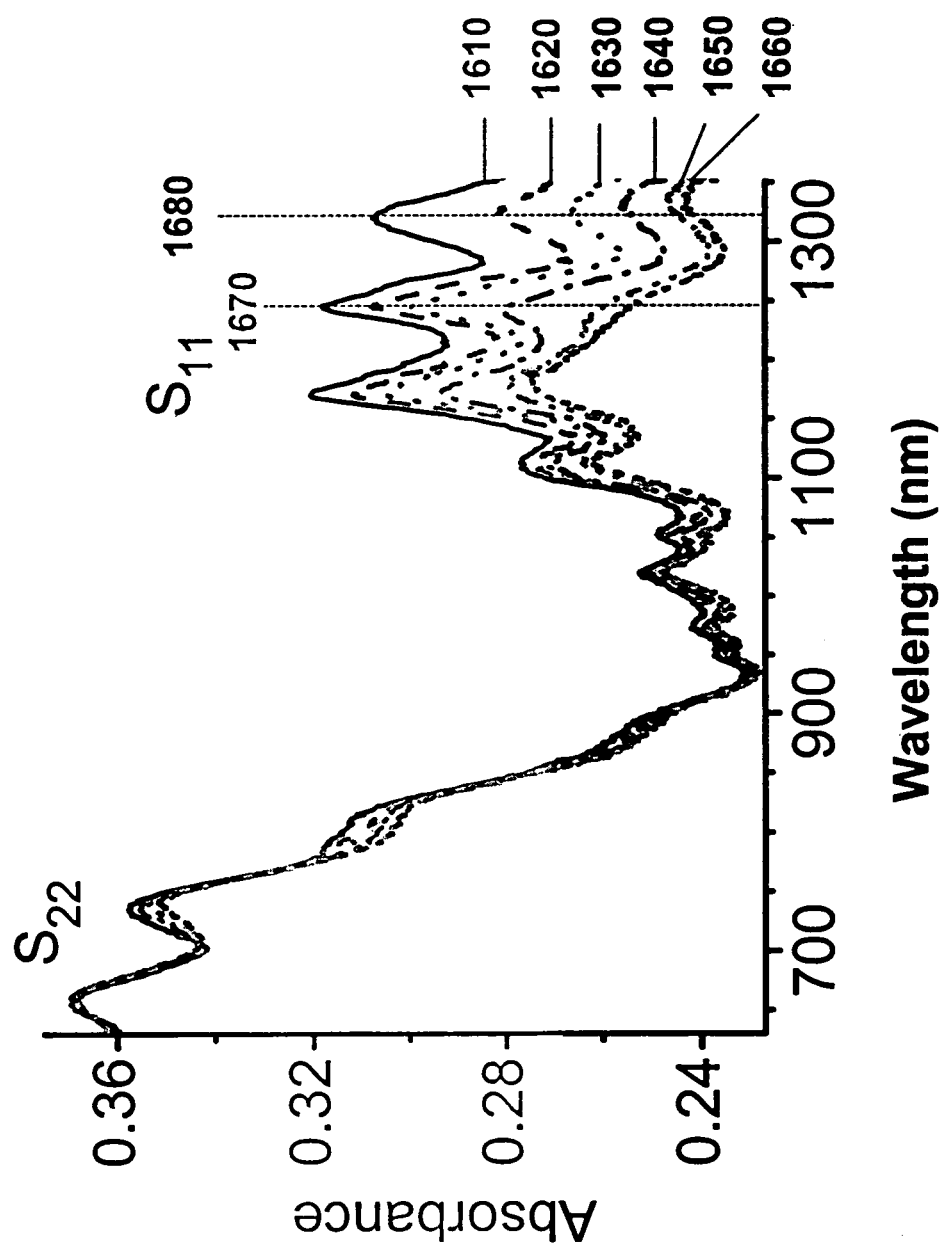
FIG. 16. shows time-dependent vis/NIR absorption spectra of SDS-SWNTs in pH 6.0 buffer solution after addition of 30 ppm $H_2O_2$.

FIG. 16 shows a typical set of time-dependent absorption spectra of SDS-encased HiPco SWNTs after addition of 30 ppm $H_2O_2$. The first interband transition of semiconducting SWNTs ($S_{11}$) occurs in the range from 830 to 1360 nm, and the second interband transition of semiconducting SWNTs ($S_{22}$) occurs from 600 to 800 nm [21]. The peak intensity at wavelengths <700 nm or between 930 and 1040 nm is insensitive to the presence of hydrogen peroxide. However, the spectral intensity decreases with time slightly between 700 and 930 nm and dramatically from 1040 to 1360 nm. Two most sensitive $S_{11}$ bands with longer wavelengths, 1245 and 1322 nm, which correspond to larger diameter nanotubes are the focus of the studies [29]. The spectral intensities are normalized to the intensity of a $S_{22}$ band at 659 nm. The band at 1245 nm (1670) could come from (8, 7) nanotubes of 1.03 nm in diameter overlapping with bands of (9, 5), (10, 3) and (10, 5) nanotubes. The band at 1322 nm (1680) could be assigned to (9, 7) nanotubes with a diameter of 1.1 nm overlapping with bands of (12, 4) and (13, 2) nanotubes [25, 29]. Note that the intensity of the $S_{11}$ bands of larger diameter nanotubes at 1245 and 1322 nm decreases with the increasing reaction time at 0, 15, 30, 60, 120, and 180 minutes, corresponding to spectra 1610, 1620, 1630, 1640, 1650, and 1660, respectively. The observed spectral changes suggest that there are strong interactions between HiPco SWNTs and $H_2O_2$, probably as a result of electron withdrawal from the valence band of the nanotubes by $H_2O_2$ oxidation. The rate of the spectral changes increases with the $H_2O_2$ concentration, indicating that the reaction is a diffusion-related process.

Figure 17:
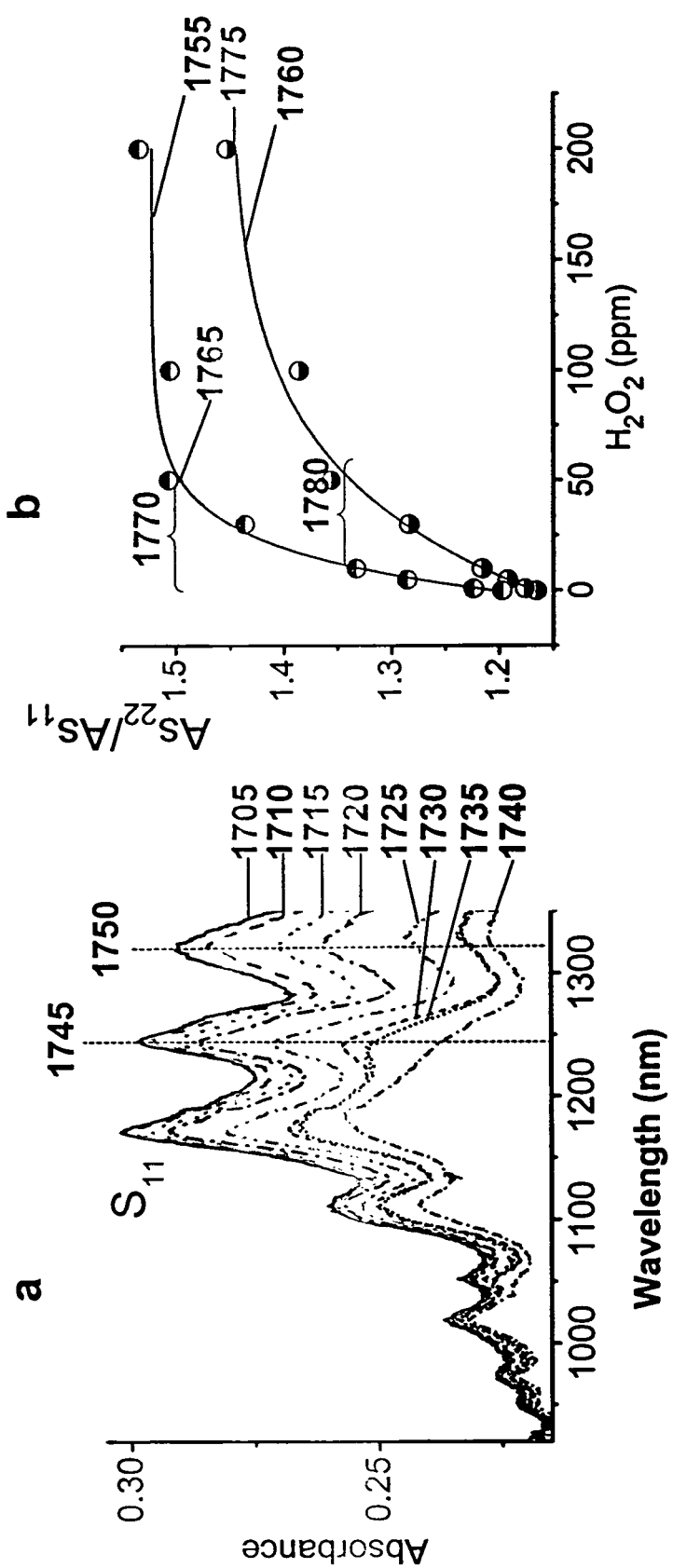
FIG. 17. shows (a) concentration-dependent vis/NIR absorption spectra of SDS-SWNTs in pH 6.0 buffer solutions under different $H_2O_2$ concentrations from 1 ppm to 200 ppm; (b) the absorbance of the $S_{11}$ band of a SDS-SWNTs sample at peaks 1245 nm and 1322 nm normalized by the absorbance of the $S_{22}$ band of the same sample at peak 659 nm, $A_{s_{22}}/A_{s_{11}}$, responding to $H_2O_2$ concentration changes exponentially.

The $H_2O_2$ concentration dependence has been measured to determine the sensitivity. FIG. 17a shows the absorption spectra of SDS-encased HiPco SWNTs in pH 6.0 buffer solutions under $H_2O_2$ concentrations ranging from 0 to 200 ppm. The spectra were taken 1 hour after mixing and the spectral intensities are normalized to the intensity of the $S_{22}$ band at 659 nm, which is not sensitive to the presence of $H_2O_2$. The intensity of the $S_{11}$ bands decreases with the increase of $H_2O_2$ concentration. The spectra 1705, 1710, 1715, 1720, 1725, 1730, 1735, and 1740 of SDS-SWNTs show concentration dependence for different $H_2O_2$ concentrations 0, 1, 5, 10, 30, 50, 100, and 200 ppm, respectively. The spectra are taken at the reaction time of 1 hour and the spectral intensities are normalized to the intensity of the $S_{22}$ band at 659 nm. There is apparent intensities erosion at 1245 nm and 1322 nm bands, as indicated by dashed lines 1745 and 1750, respectively.

FIG. 17b shows the $H_2O_2$ concentration-dependent absorbance of the two $S_{11}$ bands of 1245 nm (1760) and 1322 nm (1755), plotted as the ratio of $As_{22}/As_{11}$. Both bands grow exponentially with $H_2O_2$ concentration. The 1322 nm (1755) band change is saturated at 50 ppm (1765) with a linear relationship from 1 ppm to 50 ppm (1770). The 1245 nm (1760) band change is saturated at about 200 ppm (1775) and there is also a linear relationship from 1 ppm to 50 ppm (1780). These concentration-absorbance relationships may permit determination of the $H_2O_2$ concentration of unknown solutions.

Figure 18:
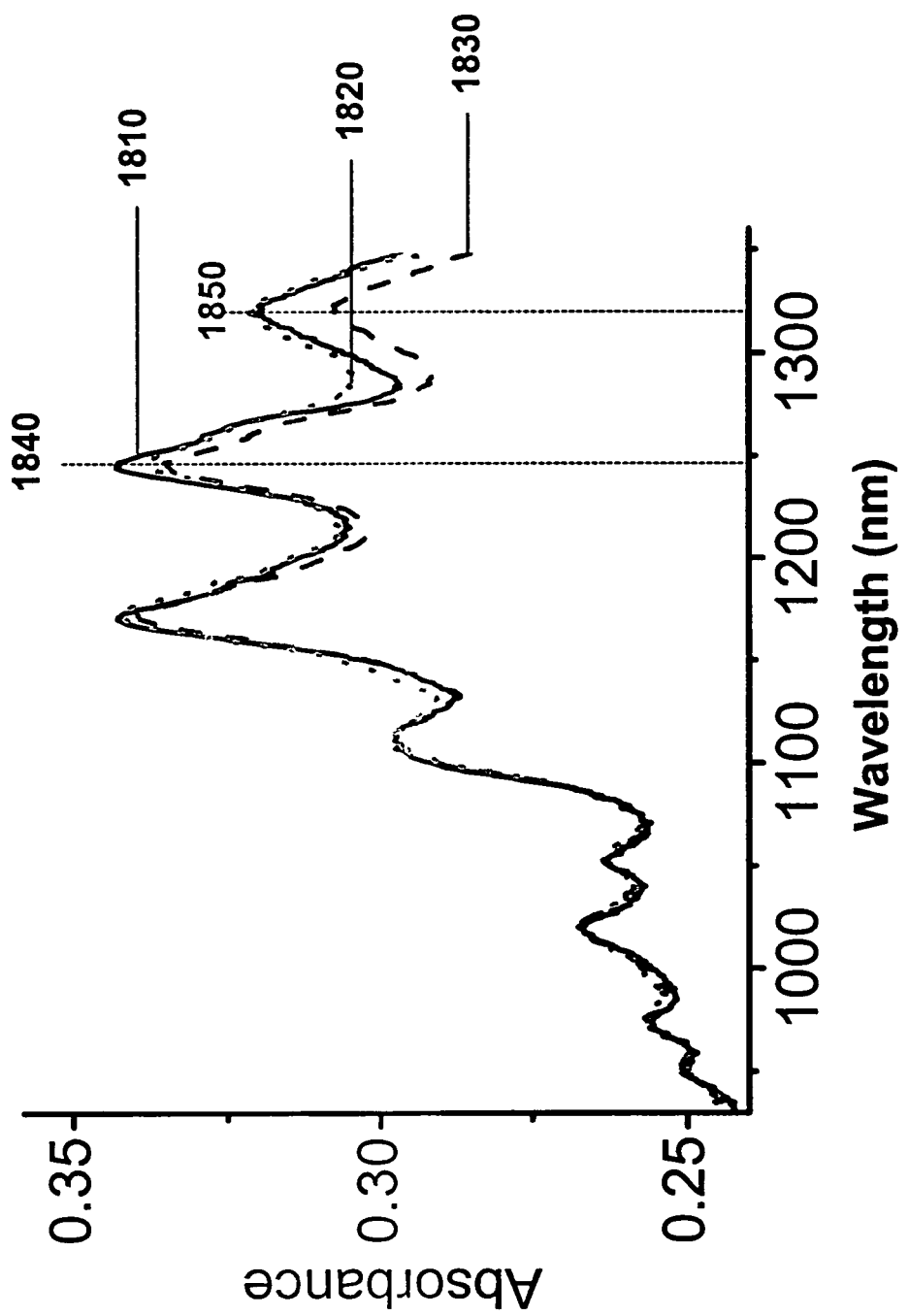
FIG. 18. shows the reversible optical response of a $H_2O_2$ interacted SDS-SWNTs sample after removal of $H_2O_2$ by $MnO_2$ catalyzed decomposition.

FIG. 18 shows the reversible optical response of a $H_2O_2$ interacted with SDS-SWNTs after removal of $H_2O_2$ by decomposing $H_2O_2$ into $H_2O$ and $O_2$ using $MnO_2$ catalyst. Data curve 1810 is the spectrum of SDS-SWNTs when there is no hydrogen peroxide present. Data curve 1830 is the spectrum of the same SDS-SWNTs when hydrogen peroxide concentration in the solution is 1 ppm. Intensity suppressions are observed at bands 1245 nm and 1322 nm as indicated by dashed lines 1840 and 1850, respectively. When $MnO_2$, a known hydrogen peroxide decomposition agent, was added, however, the spectrum returned to the level before hydrogen peroxide was added as indicated by the grey dotted line 1820.

Figure 19:
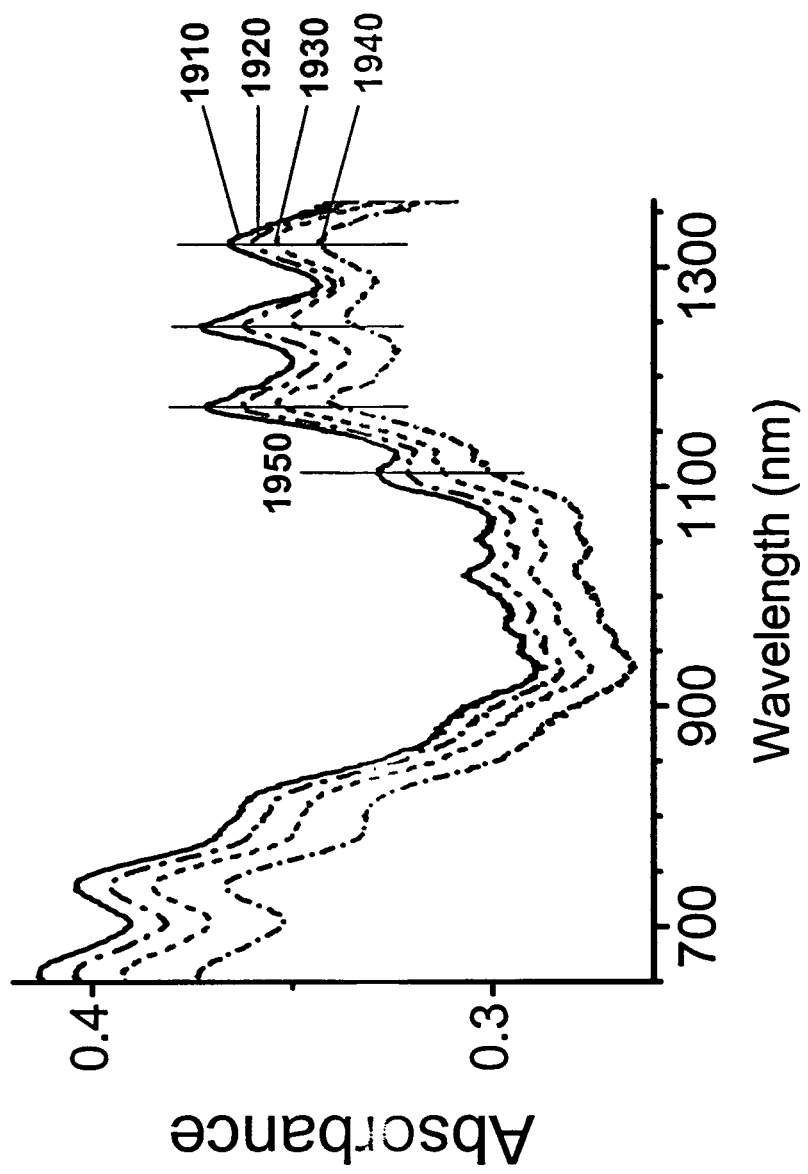
FIG. 19. shows the spectral changes of an SDS-encased HiPco SWNT solution at different catalase concentrations.

It has been shown that proteins can be immobilized on both oxidized SWNTs and vacuum-annealed SWNTs [3d, 55]. Preliminary test indicates that HiPco nanotubes can be solubilized in aqueous enzyme solutions with the assistance of mild sonication. To examine whether $H_2O_2$ is chemically reacting with SWNTs forming covalent bonds, an enzyme catalyst catalase is chosen, because catalase is capable of decomposing $H_2O_2$ into $H_2O$ and $O_2$. As shown in FIG. 19, as the catalase concentration increases from 0 (data curve 1910) to 47 (data curve 1920), 94 (data curve 1930), and 140 (data curve 1940), respectively, the $S_{11}$ bands shift to the red and the 1114 nm band (1950) disappears, suggesting that the catalase coats the SWNTs by replacing some SDS molecules. Catalase therefore can effectively decompose the $H_2O_2$. The spectral intensity reduction is due to dilution by the added catalase.

Figure 20:
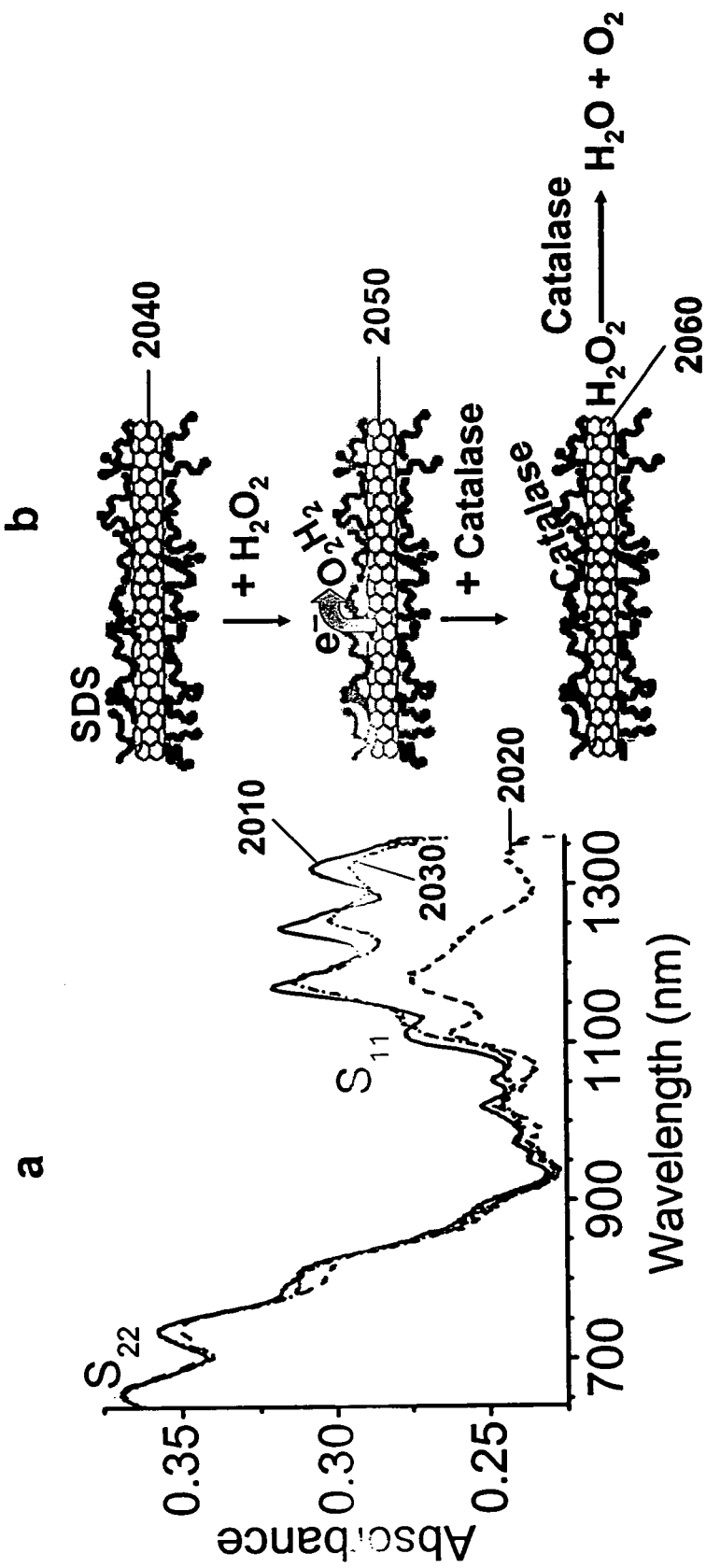
FIG. 20a. shows the recoverable optical absorption of an $H_2O_2$-interacted SDS-HiPco SWNT solution in pH 6.0 buffer after decomposing the $H_2O_2$ into $H_2O$ and $O_2$ with catalase (140 units/ml)
FIG. 20b is a schematic illustrating the interaction of $H_2O_2$ with an SDS-HiPco SWNT and the decomposition of $H_2O_2$ with catalase.

As illustrated in FIG. 20, reversible optical response was observed when catalase was used. Data curve 2010 is the spectrum of SDS-SWNTs when there is no hydrogen peroxide present. Data curve 2020 is the spectrum of the same SDS-SWNTs SWNTs when hydrogen peroxide concentration in the solution is 30 ppm. Significant intensity suppressions are observed at bands 1245 nm and 1322 nm. When catalase, a known hydrogen peroxide decomposition agent, was added, however, the spectrum returned to the level before hydrogen peroxide was added as shown in spectrum 2030. The corresponding mechanistic stages are illustrated also. Configuration 2040 illustrates an SWNT encased with SDS molecules. Configuration 2050 illustrates SDS-SWNT interacts with hydrogen peroxide. And configuration 2060 illustrates catalase interacts with SDS-SWNT in the present of hydrogen peroxide, and converts hydrogen peroxide into water and oxygen.

The recoverable behavior indicates that there are no direct chemical reactions (i.e. covalent bond formation) between the SWNT sidewalls and $H_2O_2$ under the conditions used here. Instead, the $H_2O_2$ may form charge transfer complexes with SDS-encased HiPco nanotubes and thus cause the observed spectral changes by altering the charge density on the SWNTs. $H_2O_2$ decreases the charge density of the SWNTs and so decreases the intensity of the $S_{11}$ bands [5a, 5b, 14]. Importantly, the observed recoverability of HiPco nanotubes suggests the reusability of nanotubes, which is a highly desirable feature for nanotubes-based practical sensor applications.

It is important to understand the mechanisms behind the SWNT spectral changes induced by $H_2O_2$. There are at least four possible factors that might contribute to the changes: 1) the high reduction potential of $H_2O_2$ [49]; 2) the possible reaction of $H_2O_2$ with SDS [56]; 3) electrostatic interactions between negative charged SDS micelles and $HO_2^-$ at high pHs [57]; and 4) the polar nature of $H_2O_2$ that may hinder this molecule's approach to SDS micelle-encased nanotubes. It is intuitive that the SWNT electron withdrawal by $H_2O_2$ is related to its high reduction potential (standard reduction potential $E_0$=1.763 V) [49]. Since the potential of $H_2O_2$ is tunable by changing pH, one might use pH changes to control its electron withdrawing ability and thus the optical properties of the SWNTs. The reduction potential calculations using the Nernst equation show that the reduction potential (E) of $H_2O_2$ is 1.33 V at pH 6.0 and a concentration of 100 ppm ($3.0\times10^{-3}$ M). When the pH is increased to 10.0, E=1.09 V, so there is no significant decrease in the reduction potential at higher pH. The potential E=1.09 V at pH 10.0 is still high enough to induce charge transfer from the nanotubes to hydrogen peroxide. Therefore at even higher pH the $H_2O_2$ should still induce charge transfer from nanotubes and suppress spectral features similar to those observed at pH 6.0. Surprisingly, an increase in the solution pH restores the suppressed spectral features as shown in FIG. 21a. The absorption of an SDS-SWNT solution containing 100 ppm $H_2O_2$ increases with increasing pH values of 6.3, 6.8, 7.1, 7.4, 7.8, 8.6 and 10.6, as illustrated by spectra 2110, 2120, 2130, 2140, 2150, 2160, and 2170, respectively. Spectrum 2180 is the control spectrum of SDS-SWNT alone, without hydrogen peroxide. At pH 10.6 with corresponding spectrum 2170, the absorption of the SDS-SWNT solution restores back to the absorption level observed without the addition of 100 ppm $H_2O_2$ (2780).

Furthermore, the suppression and restoration is a reversible process as one tunes the pH up (2185) and down (2190) as shown in FIG. 21b. The ratio $As_{11}/As_{22}$ of the absorbances of the $S_{11}$ (1322 nm) and the $S_{22}$ (659 nm) peaks reversibly responds to the pH changes. This unique pH-dependent optical property of the $H_2O_2$-SDS-HiPco complex suggests some important attributes for optical pH sensing applications because the pH range (6-10) that the SDS-SWNT with $H_2O_2$ system is sensitive to is complementary to other pH sensing methods using SWNTs. In addition, the above result also indicates that the high reduction potential of $H_2O_2$ may not play a significant role in the observed spectral changes. The other factors listed above may also contribute to the spectral changes.

Figure 22:
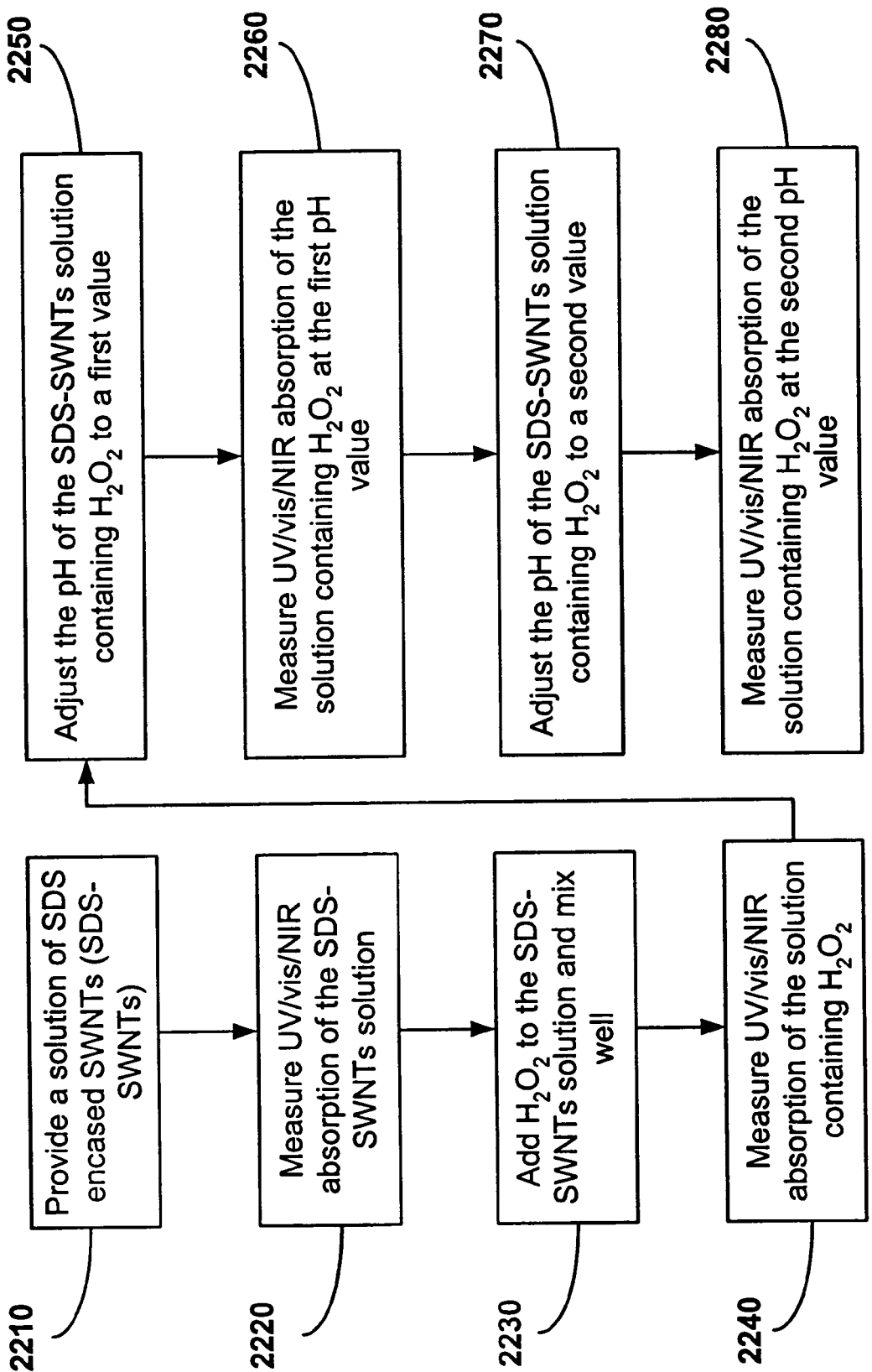
FIG. 22. is a flowchart for a process to measure the optical response of SDS-SWNTs to pH in the presence of a fixed amount of $H_2O_2$.

The process to measure the optical response of SDS-SWNTs to pH changes in the presence of fixed amount of $H_2O_2$ is schematically illustrated in FIG. 22. At step 2210, a solution of SDS-SWNTs is made or provided. In At step 2220, the UV/vis/NIR absorption of the SDS-SWNTs solution is measured as a baseline value. An amount of hydrogen peroxide is added to the solution of SDS-SWNTs and mixed well at step 2230. UV/vis/NIR absorption of the solution is measured at step 2240 to find out the change in absorption of SDS-SWNTs induced by the addition of $H_2O_2$. The pH of the SDS-SWNTs solution containing $H_2O_2$ is adjusted to a first value at step 2250. UV/vis/NIR absorption of the solution is measured to find out the change in absorption of SDS-SWNTs solution containing $H_2O_2$ at the first pH value at step 2260. The pH of the SDS-SWNTs solution containing $H_2O_2$ is adjusted to a second value at step 2270. UV/vis/NIR absorption of the solution is measured to find out the change in absorption of SDS-SWNTs solution containing $H_2O_2$ at the second pH value at step 2280. The pH adjustment and subsequent measurement are repeated until the spectrum returned to its original level.

Mechanistic Studies of the Response of SDS Encased SWNTs to Hydrogen Peroxide

To elucidate SWNT interaction mechanisms with $H_2O_2$, control experiments were carried out by choosing a mild oxidant, iodine. Iodine has a relatively low standard reduction potential of 0.620 V in the aqueous $I_2$ form and 0.536 V in the $I_3^-$ form [49]. In addition, because of the non-polar characteristic of iodine, iodine molecules may more easily approach the SDS-encased nanotubes than $H_2O_2$. Two iodine aqueous solutions were prepared to test the iodine reactions with SDS-HiPco solutions; a 30 ppm aqueous iodine $I_2$ solution without $I^-$ ions, and a 45 ppm solution containing $I_3^-$ ($1.2\times10^{-4}$ M) and $I^-$ ($2.4\times10^{-2}$ M) ions. The iodine concentration is calculated as it is presented in the HiPco solutions. The reduction potential of the later solution containing $I_3^-$ is calculated as 0.56 V, or about half of the $H_2O_2$ reduction potentials indicated above. Addition of the iodine (in both forms of aqueous $I_2$ and $I_3^-$) into the SDS-HiPco solutions at pH 6.0 suppressed the nanotube spectral features within 10 minutes. Both $I_2$ and $I_3^-$ produced the same spectral changes.

Figure 21:
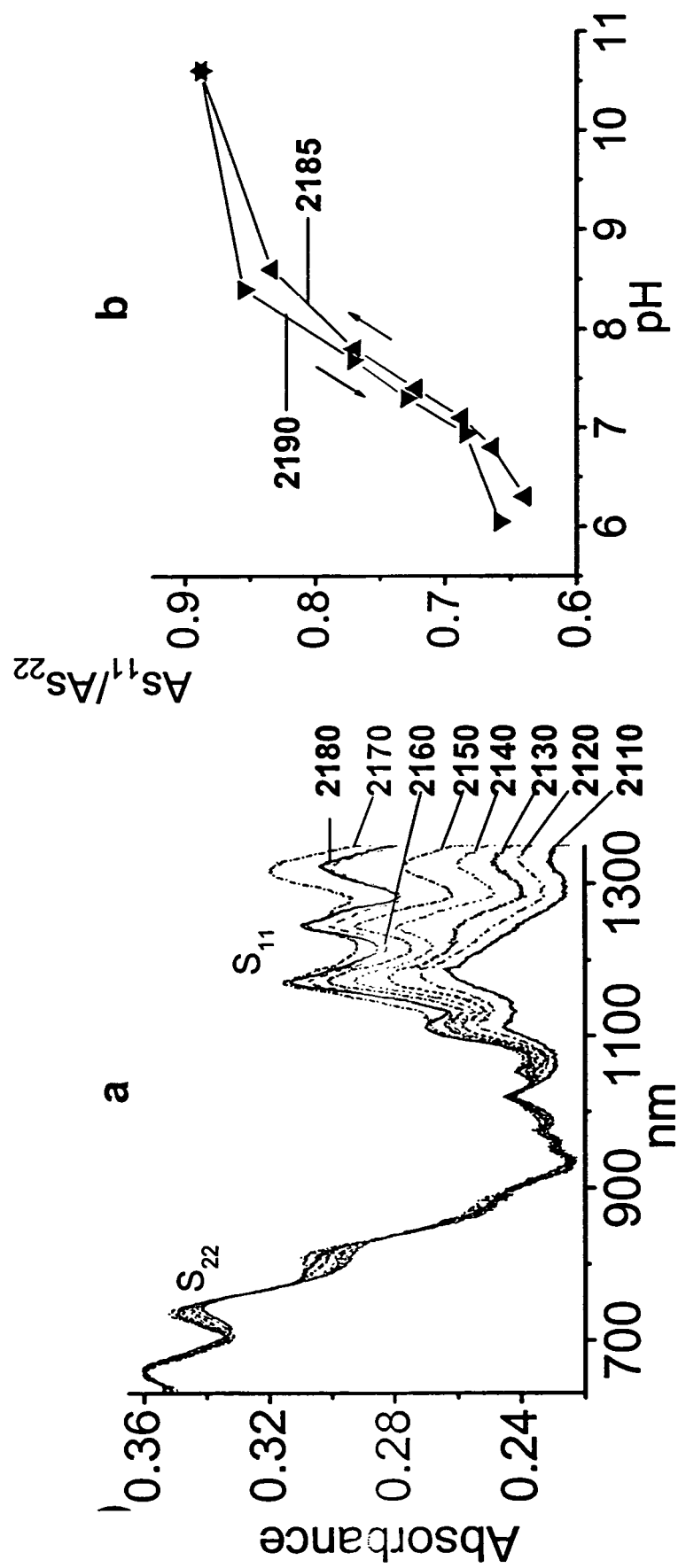
FIG. 21. shows (a) absorption spectra of an SDS-encased HiPco SWNT solution containing 100 ppm $H_2O_2$ at various pHs; (b) the ratio $As_{11}/As_{22}$ of the absorbances of the $S_{11}$ (1322 nm) and the $S_{22}$ (659 nm) peaks reversibly responds to the pH changes.
Figure 23:
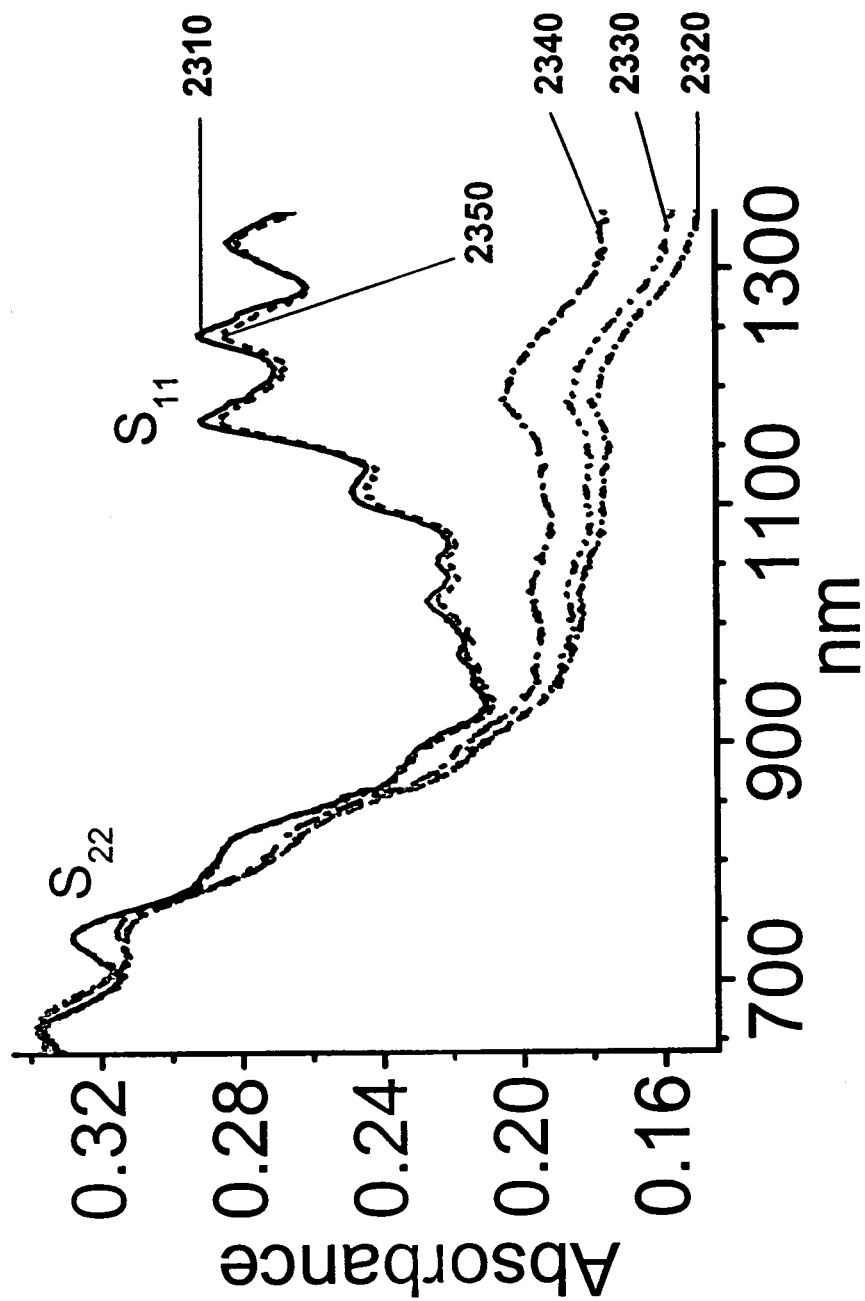
FIG. 23. shows the absorption spectra of a SDS-encased HiPco SWNT solution in a pH 6.0 buffer in response to $I_2$. The suppressed spectral features are restored by titrating the solution to pH 10.6.

FIG. 23 shows the spectral changes of an SDS-HiPco solution caused by 30 ppm $I_2$. After the addition of 30 ppm iodine the spectrum changed significantly from curve 2310 to curve 2320. The suppressed spectral features are gradually restored by titrating the solution pH with 0.1 M NaOH to 7.1 (spectrum 2330), 7.8 (spectrum 2340), and 10.6 (spectrum 2350). In contrast to $H_2O_2$, iodine also suppressed the spectral features between 930 and 1040 nm that are insensitive to $H_2O_2$. The suppressed features were restored by increasing the pH to 10.6, just as occurred with $H_2O_2$ as shown in FIG. 21.

The iodine results suggest that a high reduction potential may be not critical for the observed SWNT spectral changes. There is also a possibility that $H_2O_2$ reacts with SDS to induce the nanotube spectral changes [56]. However, the iodine results indicate that this is unlikely because iodine induces similar SWNT spectral changes even though it does not react with SDS under current conditions. Furthermore, the reversibility of the nanotube spectral changes upon removal of the $H_2O_2$ with catalase or pH tuning suggests that the $H_2O_2$-SDS-nanotube system is quite stable. It is therefore likely that both $H_2O_2$ and iodine form charge transfer complexes with HiPco nanotubes. The nonpolar nature of iodine may permit this molecule to approach SDS-encased nanotubes more readily than $H_2O_2$ and thus accelerate the spectral changes. Because of the random, structureless adsorption of SDS molecules on the sidewall of nanotubes [58], the $H_2O_2$ molecules can access the nanotube surfaces by diffusion through the micelles, causing relatively slow spectral changes induced by charge transfer, as compared to those of iodine.

Recovery of the SWNT spectral features with pH increase may reflect SDS deprotonation in more basic solutions, which changes the charge density on the SDS-encased nanotubes by refilling the valence band [5a, 5b, 6, 14] and strengthens the optical transitions. In addition, the increase in pH may increase the electrostatic interactions because the $H_2O_2$ converts to negatively charged $HO_2^-$, which is repelled from negatively charged SDS micelles [57]. The repulsion of hydrogen peroxide then eliminates electron withdrawal from the nanotubes and restores their spectral features. These two pH-related effects may work simultaneously so the suppressed spectral intensity is restored or even strengthened as shown in spectrum 2170 of FIG. 21a.

Conclusions

The near IR optical transitions of semiconducting SWNTs show that $H_2O_2$ interacts with HiPco SWNTs through valence electron withdrawal, which suppresses the nanotube spectral intensity. The SWNTs respond optically to $H_2O_2$ at concentrations as low as 1 ppm. More intriguingly, the suppressed nanotube band intensity recovers when the $H_2O_2$ is decomposed into $H_2O$ and $O_2$ with the enzyme catalyst catalase, or by increasing the solution pH. The recoverability indicates that there are no direct chemical reactions on the SWNT sidewall under these conditions. Preliminary studies on the mechanisms suggest that $H_2O_2$ may withdraw electrons from the SWNT valence band by charge transfer, which suppresses the nanotube spectral intensity. These findings set a solid foundation for $H_2O_2$ related optical sensing applications using surface-modified SWNTs.

SDS-encased, water-soluble SWNTs are optically sensitive to $H_2O_2$ and thus have potentially important applications for sensing of biological species. With recent inventions of nanolasers [33] nanowaveguides [53] and optical nanofibers [34], the nanotubes might be combined with these nano light sources for development of nanotube-based optical nanosensors in miniature devices. The optical properties of nanotubes thus hold out great promise for the accelerated realization of optical nanosensors. The findings also suggest enzyme-assisted molecular recognition applications by selective optical detection of biological species whose enzyme-catalyzed products include hydrogen peroxide.

SDS Encased SWNTs Respond to Oxidants

Similar to $H_2O_2$, the optical response of SDS-SWNTs to iodine can also be used for sensing applications. Water soluble oxidants such as $FeCl_3$, $AgNO_3$, $CuCl_2$, $(NH_4)_2(Ce(NO_3)_6)$, and $(IrCl_6)^{2-}$ can also be exploited.

Example 3

SDS Encased SWNTs for Glucose Sensing

SDS Encased SWNTs with Glucose Oxidase Response to Glucose Concentration

It has been found that nanotubes encased in the surfactant sodium dodecyl sulfate (SDS) optically respond to hydrogen peroxide at concentrations as low as 1 ppm. This finding suggests an optical sensing method for important biological molecules such as glucose, since numerous enzyme-catalyzed reactions produce hydrogen peroxide ($H_2O_2$) [52]. For example, glucose reacts catalytically with water and oxygen in the presence of the enzyme glucose oxidase ($GO_x$) to produce

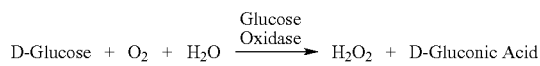

$$\text{D-Glucose} + O_2 + H_2O \xrightarrow{\text{Glucose Oxidase}} H_2O_2 + \text{D-Gluconic Acid}$$

hydrogen peroxide and gluconic acid [52]. Therefore $GO_x$-modified SWNTs should respond optically to glucose. In the present invention, it is demonstrate that water-soluble SDS-encased SWNTs treated with $GO_x$ can be used to optically detect glucose at concentrations as low as 0.25 mM.

The optical measurements were conducted under two sets of experimental conditions: (1) in pH 6.0 buffer solutions where only the product $H_2O_2$ causes SWNT spectral changes and (2) non-buffer solutions where both products $H_2O_2$ and gluconic acid are involved in the changes.

Experimental Example

Raw HiPco SWNTs (purity ~95 atm %) were purchased from Carbon Nanotechnologies, Inc [23]. Anhydrous α-D(+)-glucose (99+% pure) was purchased from Fisher Scientific. SDS (>99% pure), $GO_x$ (EC 1.1.3.4, 200 units/mg) and catalase (EC 1.11.1.6, 1870 units/mg) were from Sigma-Aldrich. A method known to people skilled in the art [23] was employed to prepare HiPco solutions in 1 wt % SDS in $H_2O$.

About 2.4 mg pristine HiPco SWNTs were weighed on a TGA microgram balance and placed in a 10 mL test tube with 5 mL 1 wt % SDS aqueous solution. In an ultrasonic bath (Branson Model 1510, 42 kHz), mild sonication was applied for 1-3 minutes to disperse HiPco nanotubes and then the mixture was vigorously sonicated for about 1 minute. Short sonication time was applied because the optical properties of HiPco SWNTs are very sensitive to sonication. The resulting mixture was centrifuged (Sargent-Welch Scientific Co.) for 1 hour. 0.8 mL of the top portion of the centrifuged sample was decanted and diluted with the SDS solution.

For the buffer conditions, about 0.13 mL of the HiPco solution was mixed with an equal amount of a pH 6.0 phosphate buffer (50 mM) in a 1 mm quartz cell. The resulting diluted solution has an optical absorbance of about 0.3 at 1245 nm with a HiPco concentration of about 0.1 mg/ml. $GO_x$ in a pH 6.0 buffer was added into the solution with a concentration of 40-80 units/mL. For the non-buffer conditions, the solution preparation procedure was the same except that the 1 wt % SDS solution was used for dilution instead of the pH 6.0 buffer. A series of such solutions were prepared with glucose concentrations from 0 to 2 mM. The time-dependent optical absorption of the solutions in 1 mm quartz cells was measured with a Perkin-Elmer Lambda 19 UV/Vis/NIR spectrometer at room temperature. SDS solutions in water or in pH 6.0 buffers without HiPco nanotubes were used as a reference for absorption background subtraction. An Orion Model 420 pH meter with a Thermo Electron Orion micro pH glass electrode was used to measure the pH of the solutions.

Figure 24:
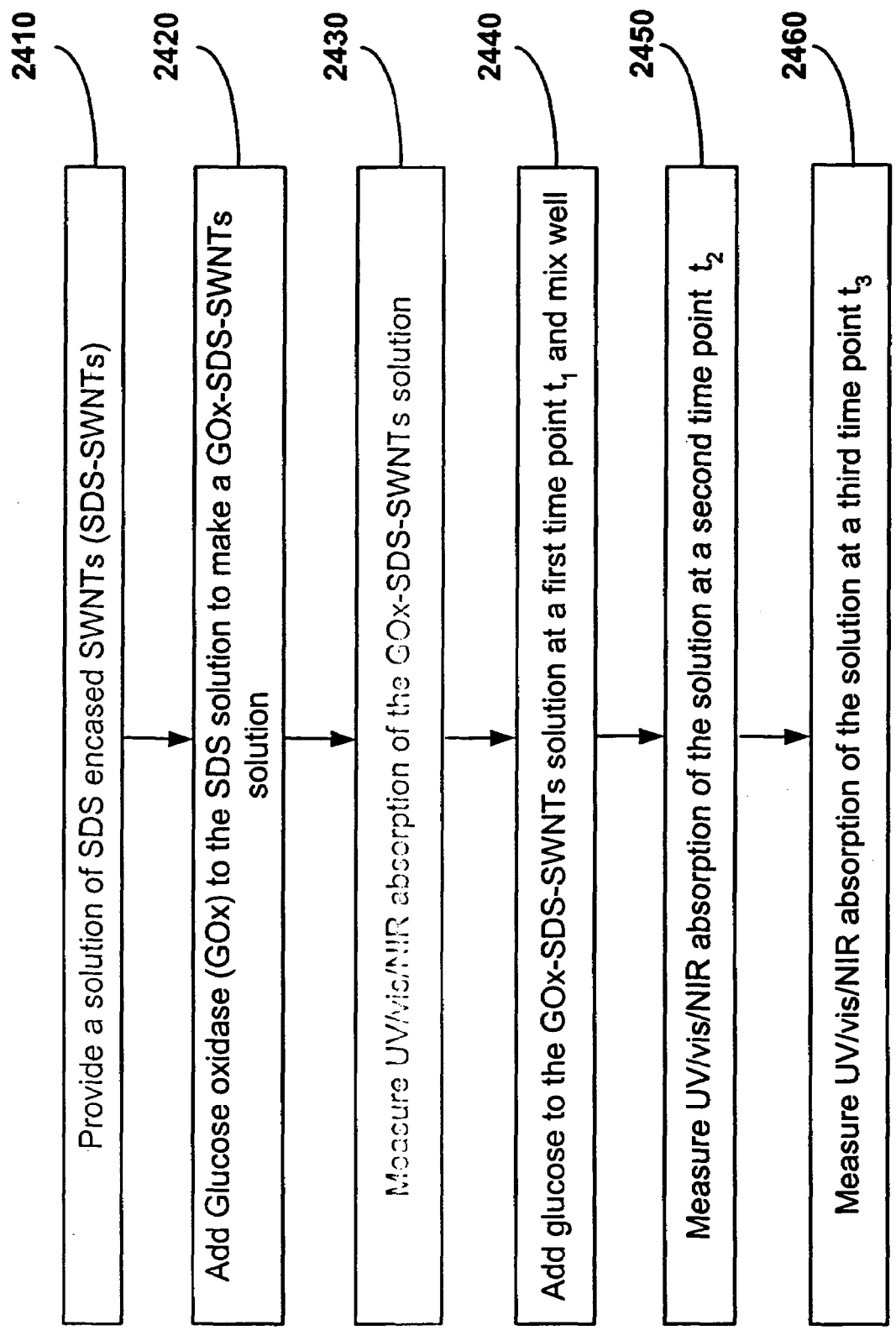
FIG. 24. is a flowchart for a process to measure the optical response of GOx-SDS-SWNTs to glucose at different time points.

A process to measure the optical response of GOx-SDS-SWNTs to glucose at different time points is schematically illustrated in FIG. 24. At step 2410, a solution of SDS-SWNTs is made or provided. At step 2420, an amount of glucose oxidase is added to the SDS-SWNT solution to make a GOx-SDS-SWNTs solution. The UN/vis/NIR absorption of the GOx-SDS-SWNTs solution is measured as a baseline at step 2430. At step 2440, an amount of glucose is added to the GOx-SDS-SWNTs solution at time point $t_1$ and mix well to form a solution with a fixed concentration of glucose. UV/vis/NIR absorption of the solution is measured at time point $t_2$ at step 2450 to find out the change in absorption of GOx-SDS-SWNTs induced by the addition of the glucose. UV/vis/NIR absorption of the solution is measured at time point $t_3$ at step 2460 to find out further change in absorption of GOx-SDS-SWNTs induced by the addition of the glucose. The process of time point measurement is repeated until all desired data is obtained.

Figure 25:
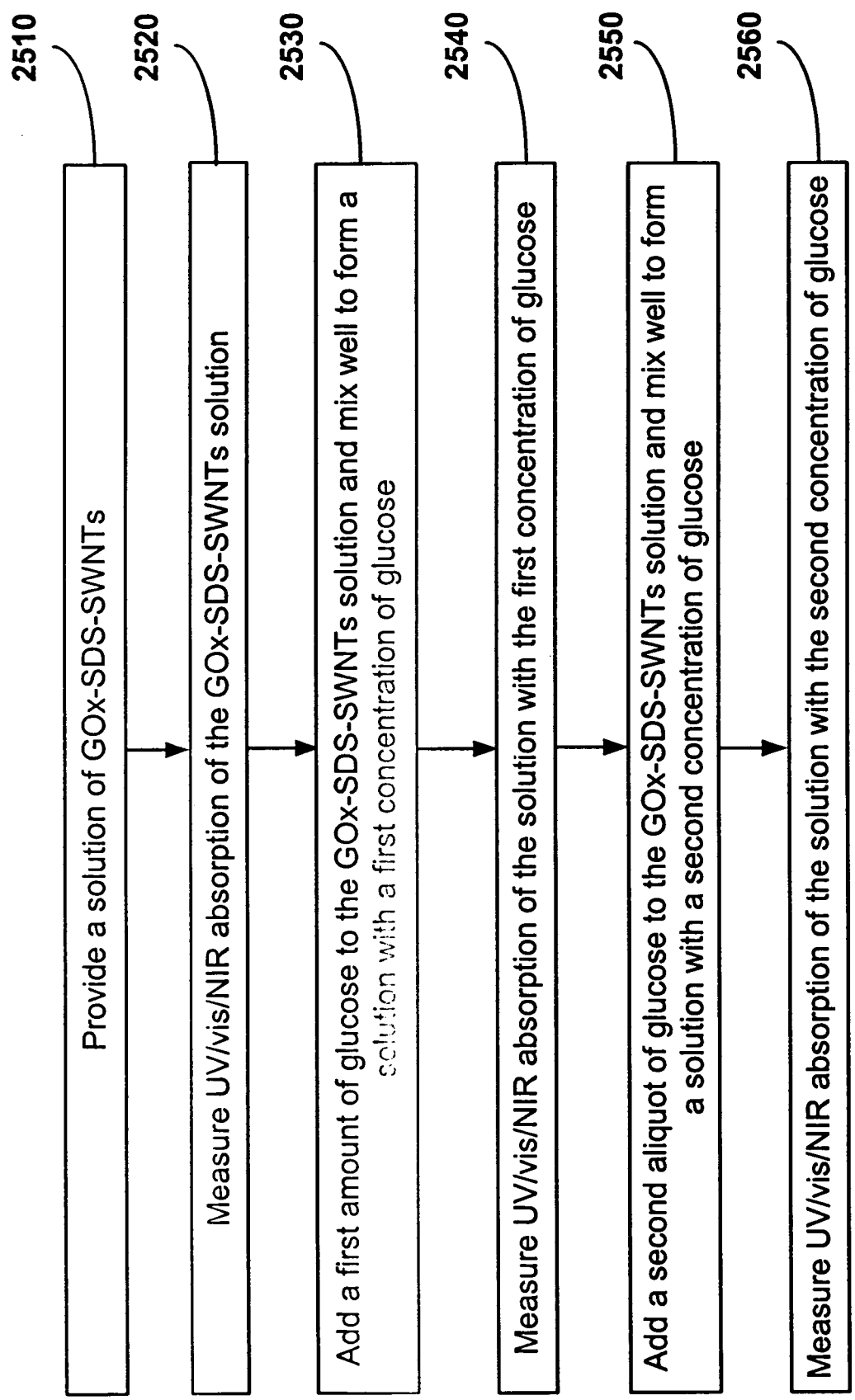
FIG. 25. is a flowchart for a process to measure the optical response of GOx-SDS-SWNTs to glucose at different glucose concentrations.

A process to measure the optical response of GOx-SDS-SWNTs to glucose at different concentrations is schematically illustrated in FIG. 25. At step 2510, a solution of GOx-SDS-SWNTs is made. At step 2520, the UN/vis/NIR absorption of the GOx-SDS-SWNTs solution is measured as a baseline. At step 2530, a first amount of glucose is added to the GOx-SDS-SWNTs solution and mix well to form a solution with a first concentration of glucose. UV/vis/NIR absorption of the solution is measured at step 2540 to find out the change in absorption of SDS-SWNTs induced by the addition of the first amount of glucose. At step 2550, a second amount of glucose is added to the GOx-SDS-SWNTs solution and mix well to form a solution with a second concentration of glucose. UV/vis/NIR absorption of the solution is measured at step 2560 to find out the change in absorption of GOx-SDS-SWNTs induced by the addition of the second amount of glucose. The process of glucose addition and subsequent measurement is repeated until data for all desired glucose concentrations are obtained.

Figure 26:
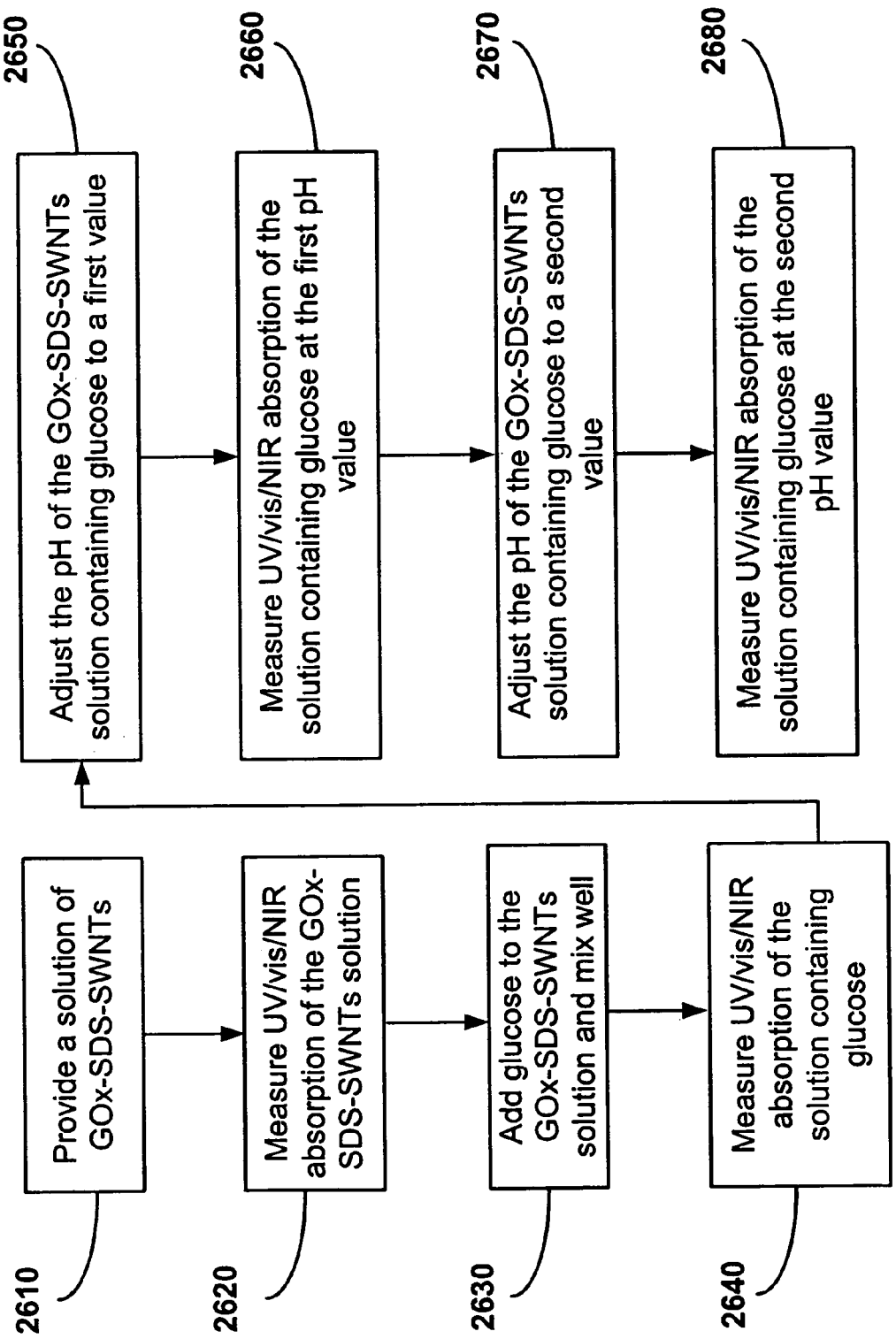
FIG. 26. is a flowchart for a process to measure the optical response of GOx-SDS-SWNTs with a fixed amount of glucose to pH changes.

The process to measure the optical response of GOx-SDS-SWNTs to pH changes in the presence of fixed amount of glucose is more specifically illustrated in FIG. 26. At step 2610, a solution of GOx-SDS-SWNTs is made. At step 2620, the UV/vis/NIR absorption of the GOx-SDS-SWNTs solution is measured as a baseline value. An amount of glucose is added to the solution of GOx-SDS-SWNTs and mixed well at step 2630. UV/vis/NIR absorption of the solution is measured to find out the change in absorption of GOx-SDS-SWNTs induced by the addition of glucose at step 2640. The pH of the GOx-SDS-SWNTs solution containing glucose is adjusted to a first value at step 2650. UV/vis/NIR absorption of the solution is measured to find out the change in absorption of GOx-SDS-SWNTs solution containing glucose at the first pH value at step 2660. The pH of the GOx-SDS-SWNTs solution containing glucose is adjusted to a second value at step 2670. UV/vis/NIR absorption of the solution is measured to find out the change in absorption of GOx-SDS-SWNTs solution containing glucose at the second pH value) 2680. The pH adjustment and subsequent measurement are repeated until the spectrum returned to its original level.

Results and Discussion

It has been demonstrated that proteins can be immobilized on the surface of SWNTs [3d, 55]. FIG. 27a shows the spectrum of the SDS-nanotube solution before (curve 2710) and after (curve 2715) the addition of $GO_x$. Spectra 2710 and 2715 look almost the same except that the three near IR peaks at 1170 nm (peak 2720), 1245 nm (peak 2730) and 1322 nm (peak 2740) shift to the red by about 3-8 nm to 1178 nm (peak 2725), 1252 nm (peak 2735) and 1324 nm (peak 2745), respectively, after addition of $GO_x$. In addition, the band 2750 at 1114 nm becomes a shoulder 2755. These observed spectral changes suggest that $GO_x$ coats the SWNTs.

Figure 27:
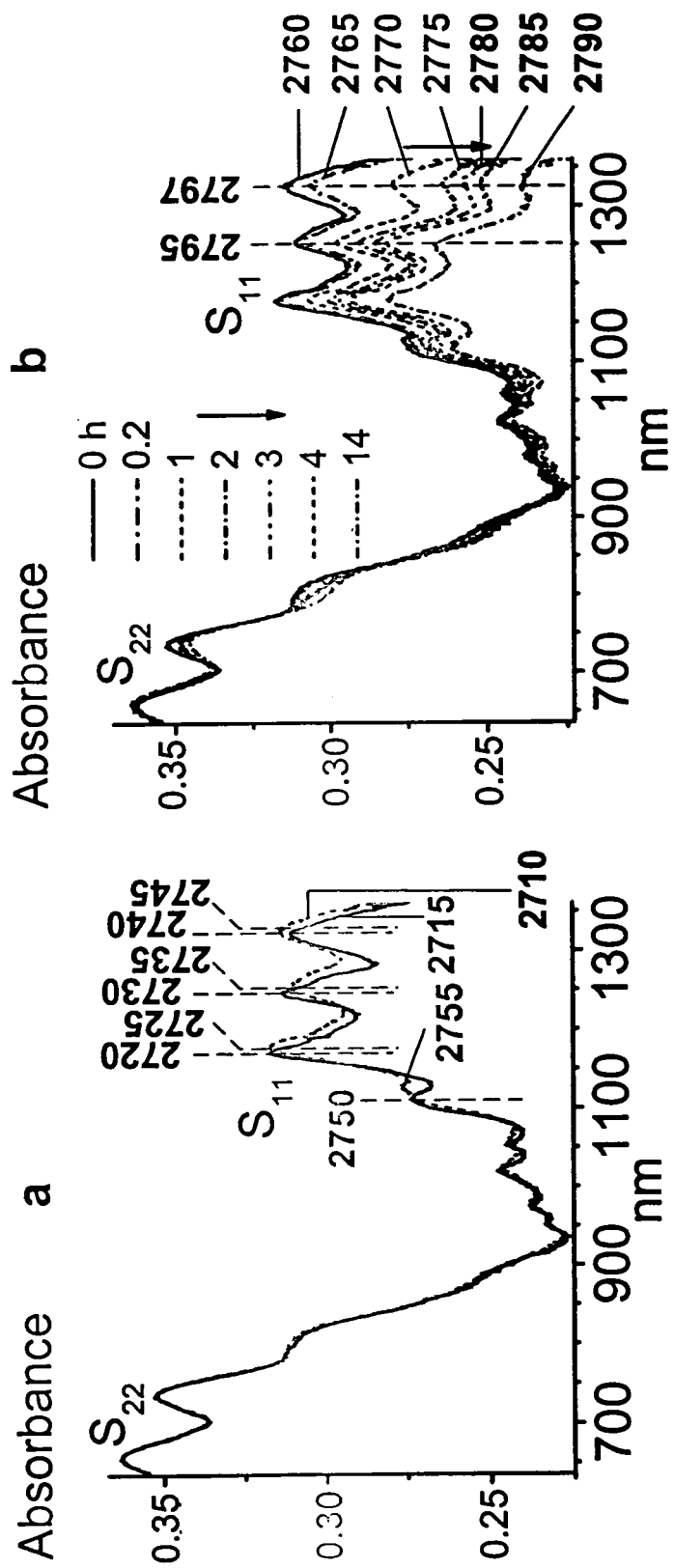
FIG. 27. shows (a) absorption spectra of SDS-encased HiPco nanotubes in a pH 6.0 buffer solution before and after addition of 40 units/mL $GO_x$; (b) absorption spectra of $GO_x$-SDS-SWNTs (HiPco) in a pH 6.0 buffer solution change with time after addition of 0.5 mM glucose.

Addition of 0.5 mM glucose changes the spectral intensity with time as shown in FIG. 27b. Spectra 2760, 2765, 2770, 2775, 2780, 2785, and 2790 correspond to time points 0, 0.2, 1, 2, 3, 4, and 14 hours, respectively. The first interband transition of semiconducting SWNTs ($S_{11}$) is in the near IR range from 830 to 1360 nm and the second interband transition of semiconducting SWNTs ($S_{22}$) ranging from 600 to 830 nm [18, 23, 24, 29]. The $S_{11}$ bands originate from individual nanotubes with different diameters and chiralities [29]. To correct the dilution effect on the spectral intensity, the spectra in FIG. 27 are normalized to the $S_{22}$ band at 659 nm, selected because it is insensitive to $H_2O_2$ or pH changes. The most sensitive $S_{11}$ bands 2795, 2797 at 1245 nm and 1322 nm correspond to (8, 7) and (9, 7) nanotubes, with 1.03 nm and 1.1 nm diameters, respectively [29]. The 1245 nm band may overlap with bands of (9, 5), (10, 3) and (10, 5) nanotubes, and the 1322 nm band overlaps with bands of (12, 4) and (13, 2) nanotubes [29]. The intensity of these $S_{11}$ bands significantly decreases with the reaction time, as was observed in the SDS-HiPco solutions reacted with $H_2O_2$. Since the pH changes are minimal in a pH buffer, the observed spectral changes are probably caused by the hydrogen peroxide produced from the glucose oxidase catalyzed glucose reaction.

Figure 28:
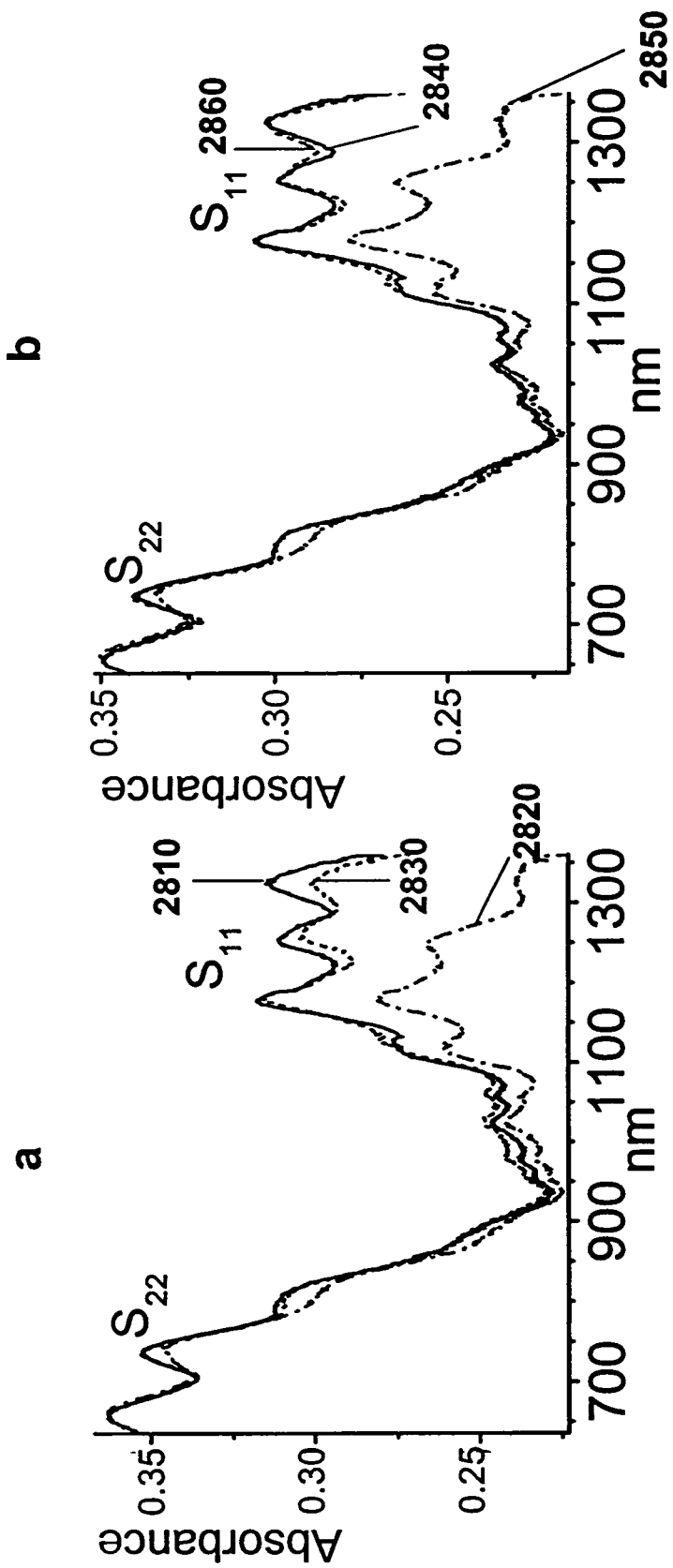
FIG. 28. shows the recovery of the optical absorption of glucose-interacted $GO_x$-SDS-SWNTs (HiPco) samples in pH 6.0 buffers with 40 units/mL $GO_x$ by the addition of (a) catalase; (b) adjusting the pH to 10.0.

It was observed that the $H_2O_2$-suppressed spectral features can be restored by decomposing $H_2O_2$ into $H_2O$ and $O_2$ with enzyme catalase or by increasing pH to more basic. Two additional experiments were conducted to verify that $H_2O_2$ induced the observed spectral changes in FIG. 27b. FIG. 28a shows that catalase restores the spectral features of the glucose-reacting nanotube solution. Curve 2810 is the spectra of SDS-SWNT in pH 6.0 buffers with 40 units/mL GOx. Curve 2820 is the spectra of SDS-SWNT in pH 6.0 buffers with 40 units/mL GOx after the addition of 0.5 mM glucose. Curve 2830 is the spectra of SDS-SWNT in pH 6.0 buffers with 40 units/mL GOx after the addition of 0.5 mM glucose with 140 units/mL catalase. Similarly, adjusting the pH of the glucose-interacted nanotube solution from 6.0 to 10.0 restores the suppressed features to what they were before glucose was added as shown in FIG. 28b. Curve 2840 is the spectra of SDS-SWNT in pH 6.0 buffers with 40 units/mL GOx. Curve 2850 is the spectra of SDS-SWNT in pH 6.0 buffers with 40 units/mL GOx after the addition of 0.5 mM glucose. Curve 2860 is the spectra of SDS-SWNT in pH 6.0 buffers with 40 units/mL GOx after the addition of 0.5 mM glucose with pH adjusted to 10 by addition of 0.1 M NaOH. These results are similar to those caused by $H_2O_2$ and suggest that the product $H_2O_2$ is responsible for the observed spectral changes in the $GO_x$-SDS-HiPco nanotubes in pH 6.0 buffers.

Figure 29:
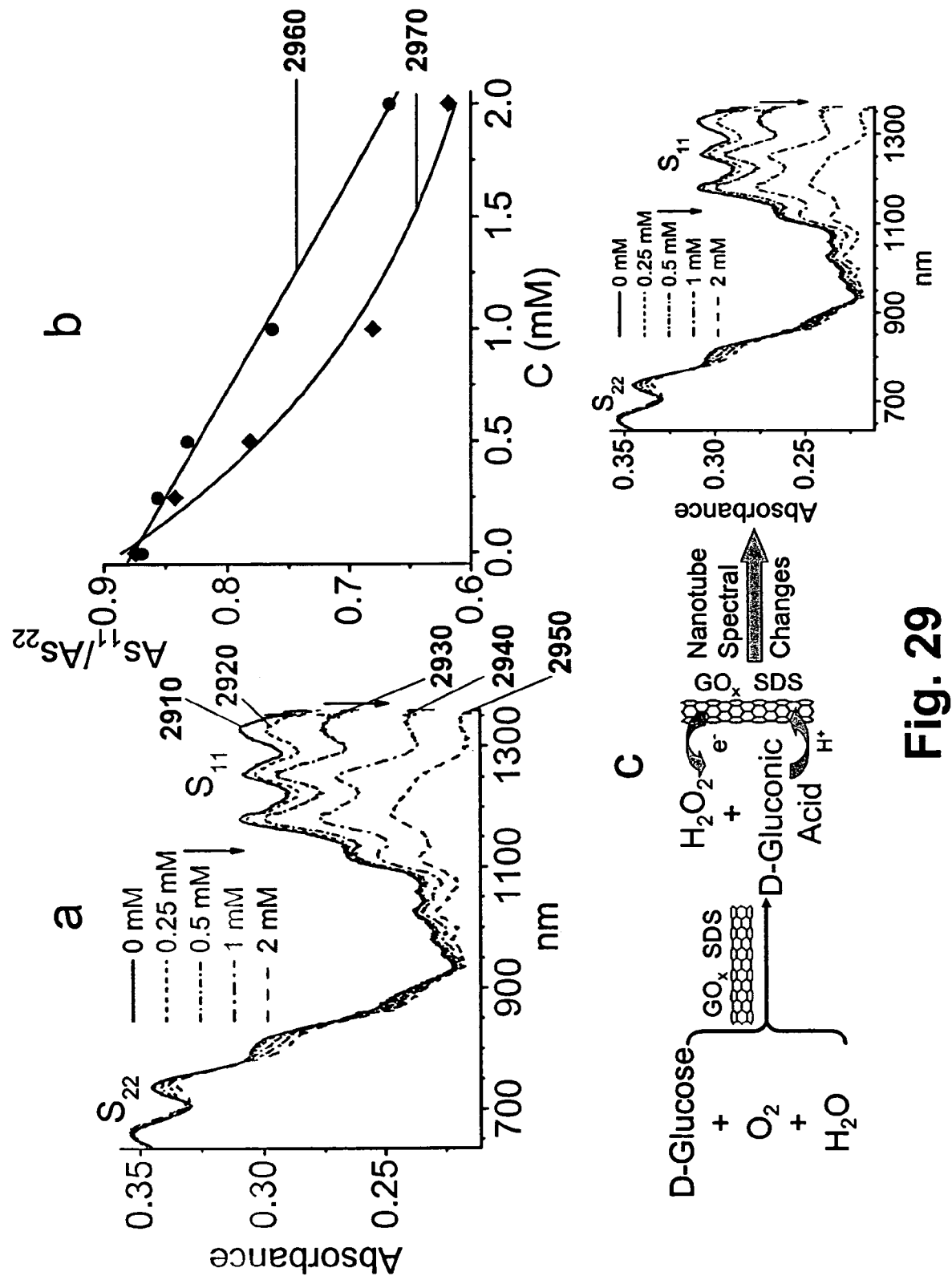
FIG. 29. shows (a) changes in the absorption spectra of $GO_x$-SDS-SWNTs (HiPco) suspended in 1 wt % SDS solution versus glucose concentration; (b) glucose concentration-dependent absorbances; (c) mechanistic illustration of the process of detecting glucose with GOx-SDS-SWNTs.

Gluconic acid is another product of the reaction. The'acid lowers the pH of an unbuffered solution. SDS-encased HiPco nanotubes are optically sensitive to pH changes [24], so both $H_2O_2$ and the acid-induced pH changes may contribute to the SWNT spectral suppression in unbuffered solutions. This dual effect enhances the sensitivity of $GO_x$-SDS-HiPco nanotubes to glucose. FIG. 29a shows the concentration-dependent absorption spectra of $GO_x$ immobilized HiPco nanotubes in 1 wt % SDS solutions (pH ~6.5) in non-buffer conditions. The positions of the two $S_{11}$ bands of (8, 7) and (9, 7) nanotubes shift from 1245 and 1322 nm to 1254 and 1328 nm, respectively with addition of 80 units/mL $GO_x$. The spectra are taken 30 min after glucose is added. Spectra 2910, 2920, 2930, 2940, and 2950 correspond to glucose concentrations 0, 0.25, 0.5, 1, and 2 mM, respectively. The intensity of the $S_{11}$ bands decreases with the increase of glucose concentration. FIG. 29b shows the normalized absorbance 2960, 2970 corresponding to the two bands at 1254 nm and 1328 nm versus glucose concentrations, respectively. The intensity of the 1254 nm band 2960 has a linear relationship with the concentrations. The intensity of the 1328 nm band 2970 decays exponentially with glucose concentration. The observed concentration dependence may permit determination of unknown glucose concentrations.

Figure 30:
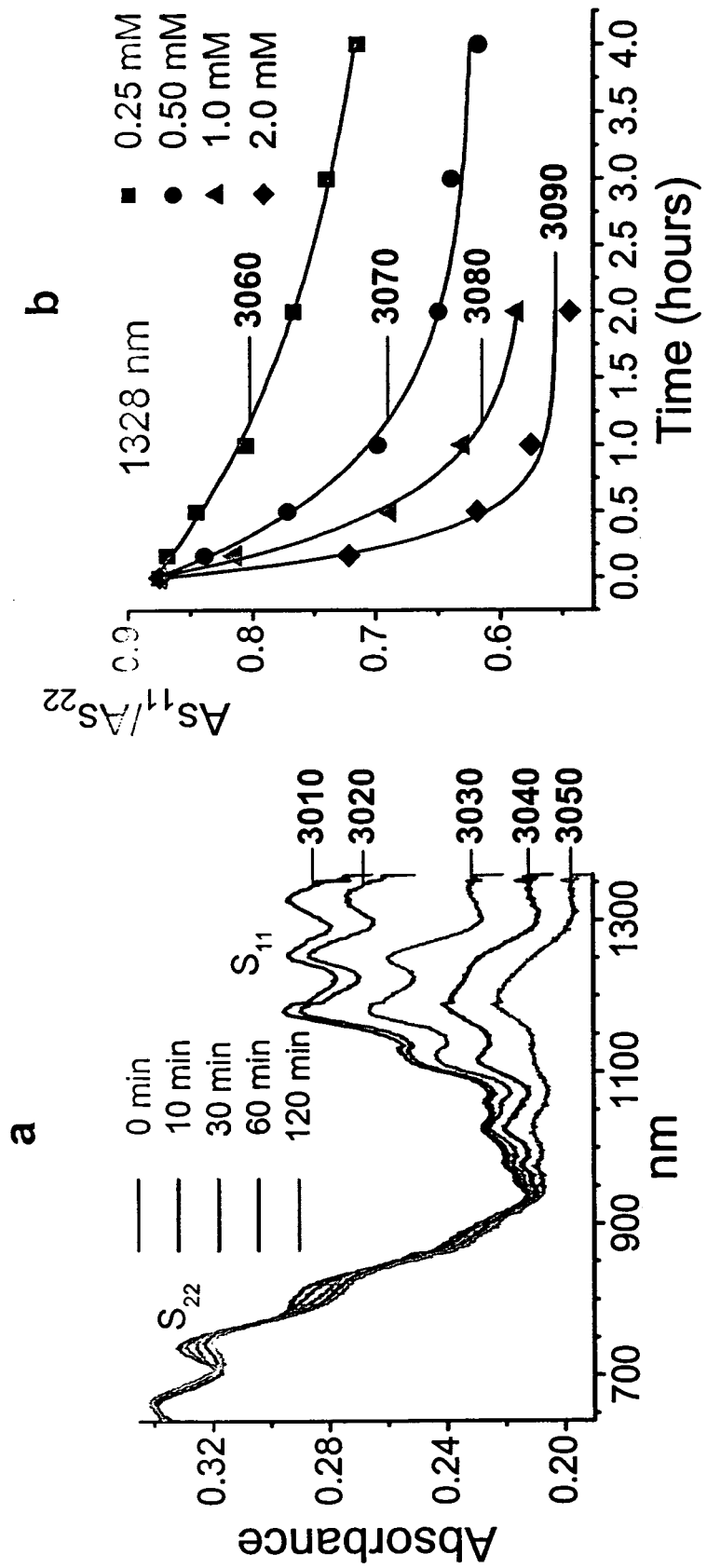
FIG. 30. shows (a) changes in the absorption spectra of $GO_x$-SDS-SWNTs in a 1 wt % SDS solution as a function of time after addition of 1.0 mM glucose; (b) as a function of time at various glucose concentrations.

The observed sensitivity of the surface-modified nanotubes to glucose may be sufficient for designing devices such as near IR optical fiber sensors [59, 60] for detecting glucose under physiologically relevant conditions, e.g. in blood where the glucose concentration is in the range of 1-20 mM [60]. The spectral changes occur more rapidly at higher glucose concentrations as shown in FIG. 30, so glucose detection will be quicker in the physiological concentration range. In FIG. 30a, changes in the absorption spectra of $GO_x$-SDS-nanotubes in a 1 wt % SDS solution as a function of time after addition of 1.0 mM glucose is shown. Spectra 3010, 3020, 3030, 3040, and 3050 correspond to time points 0, 10, 30, 60, and 120 minutes, respectively. The $GO_x$ concentration is 80 units/mL. The spectral intensities are normalized to the intensity of the $S_{22}$ band at 659 nm. FIG. 30b shows normalized absorbance of the $S_{11}$ band at 1328 nm, plotted as the ratio $As_{11}/As_{22}$ of the peaks $S_{11}$ (at 1328 nm) and $S_{22}$ (at 659 nm) of $GO_x$-SDS-HiPco nanotubes in 1 wt % SDS solution, changes as a function of time after addition of various glucose concentrations. The solid lines are fitting curves that follow exponential decays. Curves 3060, 3070, 3080, and 3090 correspond to glucose concentrations 0.25, 0.50, 1.0, and 2.0 mM, respectively. The absorbance decreases more quickly at higher glucose concentrations. The results further suggest that molecular recognition-based nanotube optical sensors could be combined with nano light sources [33, 34, 53] to create new device designs for nanoscale medical and clinical applications.

Conclusion

Water-Soluble single-walled carbon nanotubes (SWNTs) coated with glucose oxidase ($GO_x$) and sodium dodecyl sulfate (SDS) exhibit an optical response to glucose at different concentrations. The $GO_x$ catalyzed glucose reaction produces $H_2O_2$ and gluconic acid. Both products deplete electrons from the valence band of SWNTs through charge transfer with $H_2O_2$ or protonation of the encasing SDS molecules, resulting in the suppression of the SWNT spectral intensity. The peaks $S_{11}$ and $S_{22}$ correspond to the first and second interband transitions, respectively, in the density of states of semiconducting SWNTs with different diameters.

It is demonstrated for the first time that SDS-encased SWNTs immobilized with $GO_x$ can be used to optically detect glucose at concentrations as low as 0.25 mM. This sensitivity to glucose is sufficient for practical glucose sensing under physiological conditions. Nanotube-based optical sensors for molecular recognition can be integrated with recently developed nano light sources to create new approaches for nanoscale medical and clinical applications.

SDS Encased SWNTs with Glucose Oxidase and Iodide Response to Glucose

In the GOx-SDS-HiPco solutions, an amount of iodide ($I^-$) can also be added. The GOx catalyzed reaction produces $H_2O_2$, which will react with $I^-$

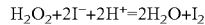

to produce iodine. It is know that $I_2$ reacts with nanotubes very effectively, so the sensitivity and response time of glucose sensing may be improved greatly.

SDS Encased SWNTs with Other Enzymes

Because SDS-SWNTs are sensitive to hydrogen peroxide, they can be used to sense a broad range of enzyme substrates whose corresponding enzymatic turnover produce hydrogen peroxide as one of the major products. Some known enzyme-substrate examples that produce hydrogen peroxide as one of their major products include uricase-uric acid, alcohol oxidase-ehtanol, cholesterol oxidase-cholesterol, and lactate oxidase-lactate etc.

Example 4

Preparation of Double-Stranded DNA Wrapped SWNTs and Analysis of Their Physical Properties In another aspect of the present invention, HiPco SWNTs can be dispersed into double-stranded DNA aqueous solutions to form stable solutions. The first optical interband transitions of the DNA wrapped semiconducting HiPco SWNTs possess a unique pH dependence, a phenomenon observed in SDS-encased and carboxylate group functionalized SWNTs.

Experimental Example

Figure 31:
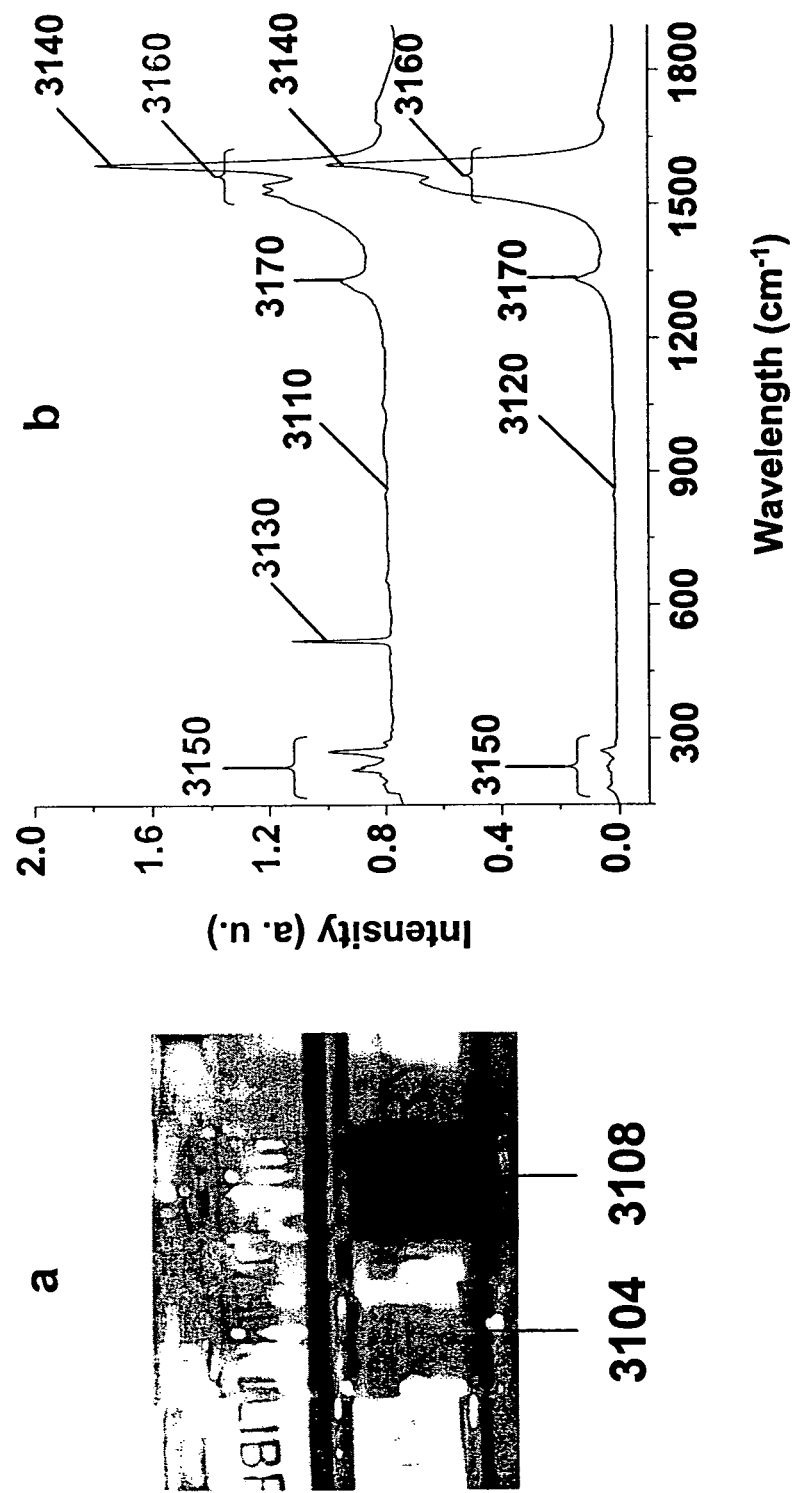
FIG. 31. shows (a) the aqueous solutions of DNA and DNA-SWNTs; (b) Raman spectra of a pristine HiPco mat sample and a DNA-SWNTs sample drop-dried on a Si substrate.

Double-stranded DNA from salmon testes was purchased from Sigma-Aldrich (catalog number D1626). Pristine HiPco SWNTs were purchased from Carbon Nanotechnologies, Inc. The samples were weighed on a microgram-scaled balance in a TGA. The solutions were prepared by a method known to people skilled in the art [27]. About 0.40 mg of DNA was added in 5.0 mL pH 7.0 Tris buffer or 10 mM TE buffer. The DNA was dissolved in the buffer by sitting overnight or by sonicating for approximately 5 minutes in an ultrasonic bath (Branson Model 1510, 42 kHz) at 0° C. A colorless transparent solution 3104 is formed and the picture of the solution is shown in FIG. 31a. 3.40 mg of HiPco nanotubes was then added into the 5 mL DNA solution and the mixture was sonicated for about 1 hour at 0° C. A black stable DNA wrapped HiPco SWNTs (DNA-SWNTs) solution 3108 is formed and the picture of the solution is shown in FIG. 31a. It has been observed that the DNA-SWNTs solution is stable for more than one year in a refrigerator. MicroRaman measurements were conducted on the samples using a ReniShaw MicroRaman 1000 Spectrometer with 532 nm laser excitation from a frequency-doubled Nd:YAG laser [28]. The spectra were calibrated with diamond single crystal and Si standards.

For pH dependence study, a DNA-SWNTs solution was titrated with 0.1 M NaOH from pH 7.0 to pH 10.0 with increments of 0.5. To test the reversibility of the pH dependence of the DNA-SWNTs sample, the pH 10.0 solution was titrated with 0.1 M HCl from pH 10.0 down to 6.0, and then back-titrated to pH 9.0 with 0.1 NaOH. The pH changes during titrations were monitored with an Orion Model 420 pH meter. UV/vis/NIR absorption spectra of the solution at different pHs were measured by using a Perkin-Elmer Lambda 19 UV/vis/NIR spectrometer. A quartz cell of 1 mm path length was used for holding solutions. A DNA solution without HiPco nanotubes was prepared as a reference. The DNA solution was titrated to the same pH as the DNA-S WNTs solution for background subtraction.

Results and Discussions

FIG. 31b illustrates Raman spectra of a pristine HiPco mat sample 3120 and a DNA-SWNTs sample 3110 drop-dried on a Si substrate. The Si substrate has excitation wavelength of 532 nm 3130. The spectra were normalized using the main tangential mode at 1588 $cm^{-1}$ 3140. The Raman spectra of pristine 3120 and DNA-SWNTs 3110 show roughly the same features including the radial breathing mode 3150 (RBM) at about 150-300 $cm^{-1}$, the tangential modes 3160 at 1500-1600 $cm^{-1}$ and the disorder (D) mode 3170 at 1330 $cm^{-1}$ [26, 28]. In comparison with the pristine HiPco sample, the D mode in the DNA-SWNTs sample shows little change in intensity, indicating that in the DNA-SWNTs sample, no significant defects were introduced in the sonication assisted dissolution process.

Figure 32:
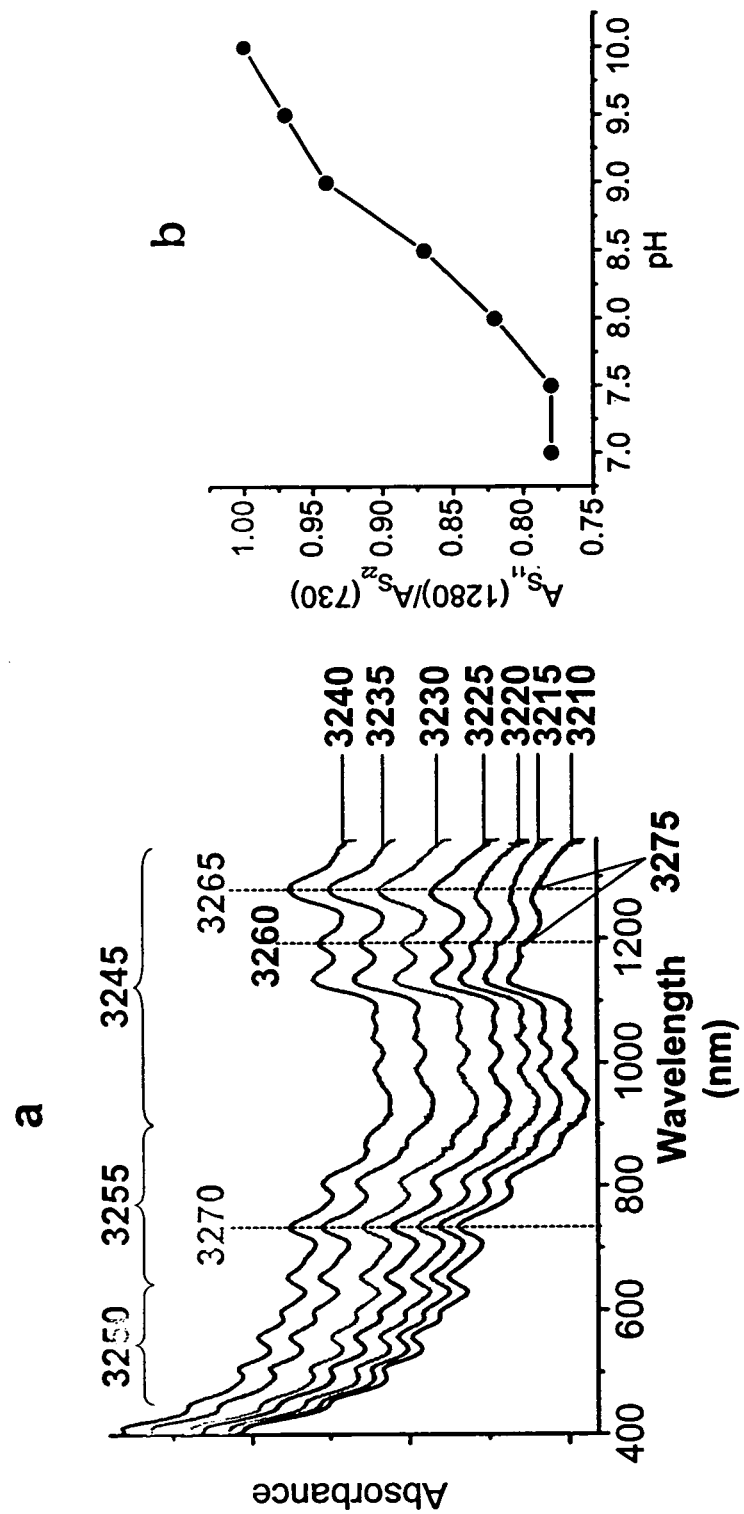
FIG. 32. shows (a) UV/vis/NIR absorption spectra of a DNA-SWNTs solution titrated from pH 7.0 to 10.0; (b) the pH dependence of the absorbance of the (8, 7) nanotube $S_{11}$ band at 1280 nm of a DNA-SWNTs sample normalized by the absorbance of the $S_{22}$ band at 730 nm of the same sample, $A_{s_{11}}(1280)/A_{s_{22}}(730)$.

The optical absorption spectra of individual SWNTs in aqueous solutions have distinct features that provide "fingerprints" for the identification of different nanotubes [23-25]. FIG. 32a shows the absorption spectra of the DNA-SWNTs solution at pH values of 7.0 (spectrum 3210), 7.5 (spectrum 3215), 8.0 (spectrum 3220), 8.5 (spectrum 3225), 9.0 (spectrum 3230), 9.5 (spectrum 3235) and 10.0 (spectrum 3240), respectively. The absorption bands 3245 (>900 nm) come from the first interband transition $S_{11}$ of semiconducting SWNTs of different diameters. The larger diameter nanotubes show bands centered at longer wavelength because the interband transition energy is approximately inversely proportional to the nanotube diameter [29]. The bands <900 nm belong to the interband transitions of the first pair $M_{11}$ of metallic nanotubes at around 440-650 nm (band 3250) and the second pair $S_{22}$ (band 3255) of semiconducting nanotubes [21, 29]. In FIG. 32a, the spectral intensity decreases due to dilution with 0.1 M NaOH. For clarity, the spectra are plotted in the same scale but shifted with equal division for clarity of illustration. When pHs are changed, there are no significant changes in the shape or intensity of the $M_{11}$ and $S_{22}$ bands. However, the $S_{11}$ bands of larger diameter nanotubes at 1190 nm (band 3260) and 1280 nm (band 3265) become more distinguishable and intensify with increasing pH. The band at 1190 nm could be assigned to (11, 3) nanotubes with a diameter of 1.01 nm overlapping with bands of (8, 6) and (12, 1) nanotubes, and the band at 1280 nm could come from (8, 7) nanotubes of 1.03 nm in diameter overlapping with bands of (9, 5), (10, 3) and (10, 5) nanotubes [25, 29]. The intensity of the two bands is suppressed at pH 7.0, but recovers when the pH is raised and the solution becomes more basic.

To investigate the relationship between pH and the intensity of the $S_{11}$ bands, the absorbance of the (8, 7) band at 1280 nm is plotted as a function of pH, as shown in FIG. 32b. To correct for the dilution effect on absorbance, the intensity of the band at 1280 nm, 3265 in FIG. 32a, is normalized to the 730 nm band, 3270 in FIG. 32a, one of the $S_{22}$ bands that are insensitive to pH changes. The normalized absorbance $A_{S_{11}}$ (1280)/$A_{S_{22}}$ (730) increases monotonically with pH in the range between 7.5 and 10.0. This range is wider than that observed by Dekker's group where the authors built an SWNTs based single-molecule electronic device [30]. They observed that when redox enzyme glucose oxidase ($GO_x$) was attached to the nanotube sidewall, the SWNTs device senses pH changes in the studied pH range from 4.0 to 5.5. The observed pH dependent behavior of the DNA-SWNTs samples resemble that observed for SWNTs functionalized with carboxylic groups [14] or encased in SDS [24], thus suggesting that the DNA serves as a pH sensing group. Specifically, the phosphate groups on the DNA deprotonate when pH is increased. The deprotonation of DNA-encased SWNTs may refill the valence band of semiconducting SWNTs with electrons, so the relative interband intensity of the $S_{11}$ bands increases [5a].

Figure 33:
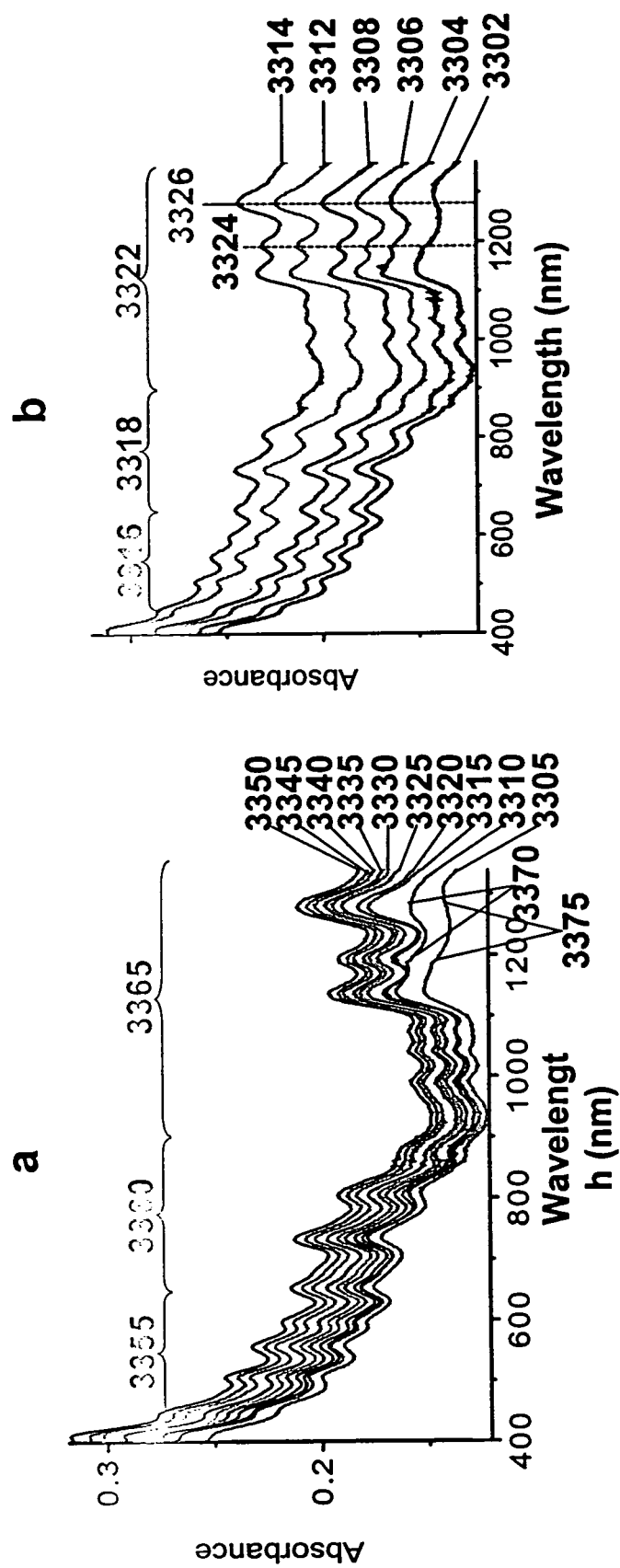
FIG. 33. shows UV/vis/NIR absorption spectra of the DNA-SWNTs solution shown in FIG. 32 titrated (a) from pH 10.0 down to 5.5; (b) from pH 6.0 up to 9.0.

The deprotonation and protonation processes appear to be reversible. To examine whether the pH-dependent optical response is reversible, the pH 10.0 DNA-SWNTs solution was back-titrated with 0.1 M HCl, and the result is shown in FIG. 33a, with spectra 3305, 3310, 3315, 3320, 3325, 3330, 3335, 3340, 3345 and 3350 correspond to pHs 5.5, 6.0, 6.5, 7.0, 7.5, 8.0, 8.5, 9.0, 9.5 and 10.0, respectively. The overall spectral intensity decreases with the decrease of pH due to the dilution from added HCl solution. The interband transitions of the first pair $M_{11}$ of metallic nanotubes at around 440-650 nm (band 3355) and the second pair $S_{22}$ (band 3360) of semiconducting nanotubes appear unchanged. The absorption bands >900 nm come from the first interband transition $S_{11}$ (band 3365) of semiconducting SWNTs. When the pH decreases to 6.0, the bands 3370 at 1190 and 1280 nm are suppressed and become indistinguishable, same for spectrum 3375 at pH 5.5. The observed features at low pHs are very similar to the features observed in the initial solution at pH 7.0 (band 3275) in FIG. 32a. It is noted that the protonation process shown in FIG. 33a does not exactly follow the deprotonation process shown in FIG. 32, i.e. there is some hysteresis during the back titration. To further verify that these two bands are recoverable by deprotonation, a third titration is performed by addition of NaOH solution to titrate from pH 6.0 up to 9.0 and the result is shown in FIG. 33b. The spectra are plotted on the same scale but shifted with equal division for clarity of illustration, with spectra 3302, 3304, 3306, 3308, 3312, and 3314 correspond to pHs 6.0, 6.5, 7.0, 7.5, 8.0 and 9.0, respectively. The overall spectral intensity decreases with the decrease of pH due to the dilution from added HCl solution. The interband transitions of the first pair $M_{11}$ of metallic nanotubes at around 440-650 nm (band 3316) and the second pair $S_{22}$ (band 3318) of semiconducting nanotubes appear unchanged. The absorption bands >900 nm come from the first interband transition $S_{11}$ (band 3322) of semiconducting SWNTs. When pH increases, the suppressed 1190 and 1280 nm features reappear as indicated along dotted lines 3324 and 3326, respectively, indicating their intensities increase with increasing pH for the DNA-SWNTs sample, same as the first deprotonation process shown in FIG. 32a, indicated along dotted lines 3260 and 3265, respectively.

In comparison with the SDS-encased HiPco SWNTs samples, which have a relative narrow pH sensitive range of about 5.0-6.0 [24], the DNA-SWNTs sample shows a pH dependent behavior at pH range above 6.0. The shift in the pH range may depend on the coating materials used whose isoelectric points or equilibrium constants contribute to the difference in pH range for protonation and deprotonation. In addition, it is observed that the charged groups on the coating materials are important for SWNTs based pH sensing, a conclusion also made by Dekker's group [30]. In another embodiment, single stranded DNA can be used to encase SWNTs for chemical compound sensing applications.

While there has been shown several and alternate embodiments of the present invention, it is to be understood that certain changes can be made as would be known to one skilled in the art without departing from the underlying scope of the invention as is discussed and set forth above and below including claims. Furthermore, the embodiments described above and claims set forth below are only intended to illustrate the principles of the present invention and are not intended to limit the scope of the invention to the disclosed elements.

LIST OF REFERENCES

[1] Kong, J.; Franklin, N. R.; Zhou, C.; Chapline, M. G.; Peng, S.; Cho, K.; Dai, H. *Science* 2000, 287, 622-625.

[2] Collins, P. G.; Bradley, K.; Ishigami, M.; Zettl, A. *Science* 2000, 287, 1801-1804.

[3] (a) Chen, R. J.; Zhang, Y.; Wang, D.; Dai, H. *J. Am. Chem. Soc.* 2001, 123, 3838-3839. (b) Shim, M.; Kam, N. W. S.; Chen, R. J.; Li, Y.; Dai, H. *Nano Lett.* 2002, 2, 285-288. (c) Kong, J.; Dai, H. *J. Phys. Chem. B* 2001, 105, 2890-2893. (d) Erlanger, B. F.; Chen, B.; Zhu, M.; Brus, L. *Nano Lett.* 2001, 1, 465-467.

[4] O'Connell, M. J.; Boul, P.; Ericson, L. M.; Huffman, C.; Wang, Y.; Haroz, E.; Kuper, C.; Tour, J.; Ausman, K. D.; Smalley, R. E. *Chem. Phys. Lett.* 2001, 342, 265-271.

[5] (a) Itkis, M. E.; Niyogi, S.; Meng, M. E.; Hamon, M. A.; Hu, H.; Haddon, R. C. *Nano Lett.* 2002, 2, 155-159. (b) Chen, J.; Hamon, M. A.; Hu, H.; Chen, Y.; Rao, A. M.; Eklund, P. C.; Haddon, R. C. *Science* 1998, 282, 95-98. (c) Yang, Y. L.; Zhang, J.; Nan, X. L.; Liu, Z. F. *J. Phys. Chem. B* 2002, 106, 4139-4144.

[6] Cui, Y.; Wei, Q.; Park, H.; Lieber, C. M. *Science* 2001, 293, 1289-1292.

[7] (a) Liu, J.; Rinzler, A. G.; Dai, H.; Hafner, J. H.; Bradley, R. K.; Boul, P. J.; Lu, A.; Iverson, T.; Shelimov, K.; Huffman, C. B.; Rodriguez-Macias, F.; Shon, Y.; Lee, T. R.; Colbert, D. T.; Smalley, R. E. *Science* 1998, 280, 1253-1256. (b) Rinzler, A. G.; Liu, J.; Dai, H.; Nikolaev, P.; Huffman, C. B.; Rodriguez-Macias, F. J.; Boul, P. J.; Lu, A.

[7] H.; Heymann, D.; Colbert, D. T.; Lee, R. S.; Fischer, J. E.; Rao, A. M.; Eklund, P. C.; Smalley, R. E. *Appl. Phys. A* 1998, 67, 29-37.

[8] Chen, J.; Rao, A. M.; Lyuksyutov, S.; Itkis, M. E.; Hamon, M. A.; Hu, H.; Cohn, R. W.; Eklund, P. C.; Colbert, D. T.; Smalley, R. E.; Haddon, R. C. *J. Phys. Chem. B* 2001, 105, 2525-2528.

[9] (a) Mickelson, E. T.; Chiang, I: W.; Zimmerman, J. L.; Boul, P. J.; Lozano, J.; Liu, J.; Smalley, R. E.; Hauge, R. H.; Margrave, J. L. *J. Phys. Chem. B* 1999, 103, 4318-4322. (b) Georgakilas, V.; Kordatos, K.; Prato, M.; Guldi, D. M.; Holzinger, M.; Hirsch, A. *J. Am. Chem. Soc.* 2002, 124, 760-761. (c) Sun, Y.; Wilson, S. R.; Schuster, D. I. *J. Am. Chem. Soc.* 2001, 123, 5348-5349.

[10] (a) Steuerman, D. W.; Star, A.; Narizzano, R.; Choi, H.; Ries, R. S.; Nicolini, C.; Stoddart, J. F.; Heath, J. R. *J. Phys. Chem. B.* 2002, 106, 3124-3130. (b) Star, A.; Steuerman, D. W.; Heath, J. R.; Stoddart, J. F. *Angew. Chem., Int. Ed.* 2002, 41, 2508-2512. (c) Bandyopadhyaya, R.; Nativ-Roth, E.; Regev, O.; Yerushalmi-Rozen, R. *Nano Lett.* 2002, 2, 25-28. (d) Pompeo, F.; Resasco, D. E. *Nano Lett.* 2002, 2, 369-373.

[11] Chiang, I. W.; Brinson, B. E.; Huang, A. Y.; Willis, P. A.; Bronikowski, M. J.; Margrave, J. L.; Smalley, R. E.; Hauge, R. H. *J. Phys. Chem. B* 2001, 105, 8297-8301.

[12] *CRC Handbook of Chemistry and Physics,* 82nd ed.; Lide, D. R., Ed.-in-Chief; CRC Press: New York, 2001-2002; p 8-43.

[13] Shimoda, H.; Gao, B.; Tang, X. P.; Kleinhammes, A.; Fleming, L.; Wu, Y.; Zhou, O. *Phys. Rev. Lett.* 2002, 88, 015502-015505.

[14] Zhao, W.; Song, C.; Pehrsson, P. *J. Am. Chem. Soc.* 2002, 124, 12418-12419.

[15] Chen, R. J.; Bangsaruntip, S.; Drouvalakis, K. A.; Kam, N. W. S.; Shim, M.; Li, Y.; Kim, W.; Utz, P. J.; Dai, H. *Proc. Natl. Acad. Sci. U.S.A.* 2003, 100, 4984.

[16] Qi, P.; Vermesh, O.; Grecu, M.; Javey, A.; Wang, Q.; Dai, H.; Peng, S.; Cho, K. *J. Nano Lett.* 2003, 3, 347.

[17] Chen, R. J.; Choi, H. C.; Bangsaruntip, S.; Yenilmez, E.; Tang, X.; Wang, Q.; Chang, Y.; Dai, H. *J. Am. Chem. Soc.* 2004, 126, 1563.

[18] Zheng, M.; Jagota, A.; Semke, E. D.; Diner, B. A.; Mclean, R. S.; Lustig, S. R.; Richardson, R. E.; Tassi, N. G. *Nature Mater.* 2003, 2, 338.

[19] Zheng, M.; Jagota, A.; Strano, M. S.; Santos, A. P.; Barone, P.; Chou, S. G.; Diner, B. A.; Dresselhaus, M. S.; Mclean, R. S.; Onoa, G. B.; Samsonidze, G. G.; Semke, E. D.; Usrey, M.; Walls, D. J. *Science* 2003, 302, 1545.

[20] Krupke, R.; Hennrich, F.; Lohneysen, H. V.; Kappes, M. M. *Science* 2003, 301, 344-347.

[21] Strano, M. S.; Dyke, C. A.; Usrey, M. L.; Barone, P. W.; Allen, M. J.; Shan, H.; Kittrell, C.; Hauge, R. H.; Tour, J. M.; Smalley, R. E. *Science* 2003, 301, 1519.

[22] Guiseppi-Elie, A.; Lei, C.; Baughman, R. H. *Nanotech.* 2002, 13, 559-564.

[23] O'Connell, M. J.; Bachilo, S. M.; Huffman, C. B.; Moore, V. C.; Strano, M. S.; Haroz, E. H.; Rialon, K. L.; Boul, P. J.; Noon, W. H.; Kittrell, C.; Ma, J.; Hauge, R. H.; Weisman, R. B.; Smalley, R. E. *Science* 2002, 97, 593.

[24] Strano, M. S.; Huffman, C. B.; Moore, V. C.; O'Connell, M. J.; Haroz, E. H.; Hubbard, J.; Miller, M.; Rialon, K.; Kittrell, C.; Ramesh, S.; Hauge, R. H.; Smalley, R. E. *J. Phys. Chem. B* 2003, 107, 6979.

[25] Ostojic, G. N.; Zaric, S.; Kono, J.; Strano, M. S.; Moore, V. C.; Hauge, R. H.; Smalley, R. E. *Phys. Rev. Lett.* 2004, 92, 117402.

[26] Filho, A. G. S.; Jorio, A.; Samsonidze, G. G.; Dresselhaus, G.; Saito, R.; Dresselhaus, M. S. *Nanotechnology* 2003, 14, 1130.

[27] Nakashima, N.; Okuzono, S.; Murakami, H.; Nakai, T.; Yoshikawa, K. *Chem. Lett.* 2003, 32, 456.

[28] Pehrsson, P. E.; Zhao, W.; Baldwin, J. W.; Song, C.; Liu, J.; Zheng, B. *J. Phys. Chem. B* 2003, 107, 5690.

[29] Weisman, R. B.; Bachilo, S. M. *Nano Lett.* 2003, 3, 1235.

[30] Besteman, K.; Lee, J.-O.; Wiertz, F. G. M.; Heering, H. A.; Dekker, C. *Nano Lett.* 2003, 3, 727.

[31] Lin, Y.; Lu, F.; Tu, Y.; Ren, Z.; *Nano Lett.* 2004, 4, 191-195.

[32] Johnson et al *Nature Materials* 2002, 1, 106-110.

[33] Schaller, R. D.; Petruska, M. A.; Klimov, V. I.; *J. Phys. Chem. B* 2003, 107, 13765-13768.

[34] Tong, L.; Gattass, R. R.; Ashcom, J. B.; He, S.; Lou, J.; Shen, M.; Maxwell, I.; Mazur, E. *Nature* 2003, 426, 816-819.

[35] Goldoni, A.; Larciprete, R.; Petaccia, L.; Lizzit, S. *J. Am. Chem. Soc.* 2003, 125, 11329-11333.

[36] Mark, G.; Schuchmann, H. P.; von Sonntag C. *J. Am. Chem. Soc.* 2000, 122, 3781-3782.

[37] Misik, V.; Riesz, P. *J. Phys. Chem.* 1996, 100, 17986-17994.

[38] Hart, E. J.; Fischer, C. H.; Henglein, A. *J. Phys. Chem.* 1986, 90, 5989-5991.

[39] Beuthe, H. *Z Physik. Chem.* 1933, A163, 161-171.

[40] Virtanen, A. I.; Ellfolk, N. *J. Am. Chem. Soc.* 1950, 72, 1046-1047.

[41] Mead, E. L.; Sutherland, R. G.; Verrall, R. E. *Can. J. Chem.* 1976, 54, 1114-1120.

[42] Someya, T.; Small, J.; Kim, P.; Nuckolls, C.; Yardley, J. T. *Nano Lett.* 2003, 3, 877-881.

[43] Bradley, K.; Cumings, J.; Star, A.; Gabriel, J.-C. P.; Gruner, G. *Nano Lett.* 2003, 3, 639-641.

[44] Li, J.; Lu, Y.; Ye, Q.; Cinke, M.; Han, J.; Meyyappan, M. *Nano Lett.* 2003, 3, 929-933.

[45] Kamaras, K.; Itkis, M. E.; Hu, H.; Zhao, B.; Haddon, R. C. *Science* 2003, 301, 1501.

[46] Dekker, C. Phys. Today 1999, 52, 22-28.

[47] Hahm, J.-i.; Lieber, C. M. *Nano Lett.* 2004, 4, 51-54.

[48] Kelley, K.; Pehrsson, P. E.; Ericson, L. M.; Zhao, W. Submitted to J. Nanosci. Nanotech.

[49] Harris, D. C. *Exploring chemical Analysis,* $3^{rd}$ ed.; W. H. Freeman and Company: New York, 2004; Pages 187 and 224.

[50] An, L.; Fu, Q.; Lu, C.; Liu, J. *J. Am. Chem. Soc.* 2004; 126, 10520-10521.

[51] Star, A.; Lu, Y.; Bradley, K.; Gruner, G. *Nano Lett.* 2004, 4, 1587-1591.

[52] Turner, A. P. F.; Karube, I.; Wilson, G. S., Eds. *Biosensors: Fundamentals and Applications*; Oxford Univ. Press: New York, 1987.

[53] Law, M.; Sirbuly, D. J.; Johnson, J. C.; Goldberger, J.; Saykally, R. J.; Yang, P. *Science* 2004, 305, 1269-1273.

[54] Zhao, W.; Song, C.; Zheng, B.; Liu, J.; Viswanathan, T. *J. Phys. Chem. B* 2002, 106, 293-296.

[55] Azamian, B. R.; Davis, J. J.; Coleman, K. S.; Bagshaw, C. B.; Green, M. L. H. *J. Am. Chem. Soc.* 2002, 124, 12664-12665.

[56] Ponganis, K. V.; De Araujo, M. A.; Hodges, H. L. *Inorg. Chem.* 1980, 19, 2704-2709.

[57] Jankovic, I. A.; Cakar, M. M.; Nedeljkovic, J. M. J *Serbian Chem. Soc.* 1999, 64, 359-364

[58] Yurekli, K.; Mitchell, C. A.; Krishnamoorti, R. *J. Am. Chem. Soc.* 2004, 126, 9902-9903.

[59] Prasad, P. N., *Introduction to Biophotonics*, John Wiley: New York, 2003.

[60] Mattu, M. J.; Small, G. W.; Arnold, M. A.; *Anal. Chem.* 1997, 69, 4695-4702.

What is claimed is:

1. A method for measuring hydrogen peroxide concentration in a solution by using single-walled carbon nanotubes coated with a negative charge group, comprising the steps of:
   a. providing the single-walled carbon nanotubes coated with the negative charge group to the solution to be detected;
   b. measuring optical absorption of the solution containing the negative charge group-coated single-walled carbon nanotubes, wherein the optical absorption of the solution containing the negative charge group-coated single-walled carbon nanotubes is correlated with hydrogen peroxide concentration of the solution to be detected; and
   c. subsequently decomposing any hydrogen peroxide in the solution into $H_2O$ and $O_2$, wherein decomposing any hydrogen peroxide in the solution into $H_2O$ and $O_2$ comprises adding catalase or $MnO_2$ to the solution after measuring optical absorption of the solution containing the negative charge group-coated single-walled carbon nanotubes.

2. A method for measuring pH in a solution by using single-walled carbon nanotubes coated with a negative charge group, comprising the steps of:
   a. providing the single-walled carbon nanotubes coated with a negative charge group to the solution to be detected;
   b. adding an amount of hydrogen peroxide to the solution to increase the sensitivity of the negative charge group-coated single-walled carbon nanotubes to pH change in the solution; and
   c. measuring optical absorption of the solution containing the negative charge group-coated single-walled carbon nanotubes,
   wherein the optical absorption of the solution containing the negative charge group-coated single-walled carbon nanotubes is correlated with the pH of the solution to be detected.

3. The method of claim 1, wherein the step of providing further comprises the step of adding an enzyme to the solution containing the negative charge group-coated single-walled carbon nanotubes, wherein the enzyme can catalyze a reaction of a substrate in the solution to produce hydrogen peroxide.

4. The method of claim 1, wherein the negative charge group comprises one of carboxylate, sulfonate, sulfate, phosphate, amines and any combination thereof.

5. The method of claim 1, wherein the negative charge group is selected from a compound comprising one of single-stranded DNA, double-stranded DNA, protein, sodium dodecyl sulfate (SDS), poly(sodium 4-styrenesulfonate) (PSS) and any combination thereof.

6. The method of claim 1, wherein the negative charge group-coated single-walled carbon nanotubes are isolated or aggregated.

7. The method of claim 1, wherein the negative charge group-coated single-walled carbon nanotubes comprise one of semiconducting nanotubes, metallic nanotubes and any combination thereof.

8. The method of claim 3, wherein the substrate concentration in the solution is correlated with the detected hydrogen peroxide concentration in the solution, and the detected hydrogen peroxide concentration is correlated with an amount of hydrogen peroxide produced by the enzyme catalyzed reaction of the substrate in the solution.

9. The method of claim 3, wherein the enzyme is glucose oxidase and the substrate in the solution is glucose.

10. The method of claim 3, wherein the enzyme is alcohol oxidase and the substrate in the solution is alcohol.

11. The method of claim 3, wherein the enzyme is uricase and the substrate in the solution is uric acid.

12. The method of claim 3, wherein the enzyme is cholesterol oxidase and the substrate in the solution is cholesterol.

13. The method of claim 3, wherein the enzyme is lactate oxidase and the substrate in the solution is lactate.

14. The method of claim 2, wherein the optical absorption is measured at a wavelength in a range of from about 700 to about 2000 nm.

15. The method of claim 2, wherein the negative charge group comprises one of carboxylate, sulfonate, sulfate, phosphate, amines and any combination thereof.

16. The method of claim 2, wherein the negative charge group is selected from a compound comprising one of single-stranded DNA, double-stranded DNA, protein, sodium dodecyl sulfate (SDS), poly(sodium 4-styrenesulfonate) (PSS) and any combination thereof.

17. The method of claim 2, wherein the negative charge group-coated single-walled carbon nanotubes are isolated or aggregated.

18. The method of claim 2, wherein the negative charge group-coated single-walled carbon nanotubes comprise one of semiconducting nanotubes, metallic nanotubes and any combination thereof.

* * * * *